US009095592B2

(12) United States Patent
Conklin et al.

(10) Patent No.: US 9,095,592 B2
(45) Date of Patent: Aug. 4, 2015

(54) BRUTON'S TYROSINE KINASE AS ANTI-CANCER DRUG TARGET

(71) Applicant: The Research Foundation Of State University Of New York At Albany, Albany, NY (US)

(72) Inventors: Douglas S. Conklin, Niskayuna, NY (US); Cheryl Eifert, Huntington Station, NY (US); Antonis Kourtidis, Saint Augustine, FL (US); Xianhui Wang, Albany, NY (US); Leila Kokabee, Albany, NY (US)

(73) Assignee: THE RESEARCH FOUNDATION FOR THE STATE UNIVERSITY OF NEW YORK, Albany, NY (US)

( * ) Notice: Subject to any disclaimer, the term of this patent is extended or adjusted under 35 U.S.C. 154(b) by 0 days.

(21) Appl. No.: 13/971,662

(22) Filed: Aug. 20, 2013

(65) Prior Publication Data
US 2014/0073593 A1 Mar. 13, 2014

Related U.S. Application Data

(63) Continuation-in-part of application No. 13/330,062, filed on Dec. 19, 2011, now Pat. No. 8,513,212, which is a continuation of application No. 12/613,937, filed on Nov. 6, 2009, now abandoned.

(60) Provisional application No. 61/112,406, filed on Nov. 7, 2008.

(51) Int. Cl.
| C12N 15/11 | (2006.01) |
|---|---|
| A61K 31/519 | (2006.01) |
| A61K 31/713 | (2006.01) |
| C12N 15/113 | (2010.01) |
| A61K 31/704 | (2006.01) |
| A61K 45/06 | (2006.01) |
| C12N 9/12 | (2006.01) |
| G01N 33/573 | (2006.01) |
| G01N 33/574 | (2006.01) |
| C07K 14/705 | (2006.01) |

(52) U.S. Cl.
CPC ............ *A61K 31/519* (2013.01); *A61K 31/704* (2013.01); *A61K 31/713* (2013.01); *A61K 45/06* (2013.01); *C07K 14/705* (2013.01); *C12N 9/1205* (2013.01); *C12N 15/1137* (2013.01); *C12Y 207/10001* (2013.01); *C12Y 207/10002* (2013.01); *G01N 33/573* (2013.01); *G01N 33/57415* (2013.01); *C12N 2310/14* (2013.01); *G01N 2333/9121* (2013.01)

(58) Field of Classification Search
CPC ............ C12N 15/1137; C12N 9/1205; C12N 2310/14
See application file for complete search history.

(56) References Cited

U.S. PATENT DOCUMENTS

| 4,683,195 | A | 7/1987 | Mullis et al. | 435/6.11 |
|---|---|---|---|---|
| 4,683,202 | A | 7/1987 | Mullis | 435/91.2 |
| 4,965,188 | A | 10/1990 | Mullis et al. | 435/6.12 |
| 7,514,444 | B2 * | 4/2009 | Honigberg et al. | 514/263.22 |
| 8,299,081 | B2 * | 10/2012 | Michelson et al. | 514/253.03 |
| 8,513,212 | B2 * | 8/2013 | Conklin et al. | 514/44 A |
| 2008/0081791 | A1 * | 4/2008 | Huang et al. | 514/44 |
| 2010/0081704 | A1 * | 4/2010 | Lavitrano et al. | 514/44 A |

FOREIGN PATENT DOCUMENTS

| EP | 1473039 A1 * | 3/2004 |
|---|---|---|
| WO | WO2007/124252 A2 * | 11/2007 |
| WO | WO2008110624 A2 * | 9/2008 |

OTHER PUBLICATIONS

Adnane, J. et al. (1991) "BEK and FLG, two receptors to members of the FGF family, are amplified in subsets of human breast cancers," *Oncogene* 6(4), 659-663.
Advani, A. S. et al. (2002) "Bcr—Abl variants: biological and clinical aspects," *Leukemia Research* 26(8), 713-720.
Archey, W. B. et al. (1999) "Methylation of CpGs as a Determinant of Transcriptional Activation at Alternative Promoters for Transforming Growth Factor-β3," *Cancer Research* 59(10), 2292-2296.
Arvanitis, D. et al. (2008) "Eph/ephrin signaling: networks," *Genes & Development* 22(4), 416-429.
Bäckesjö, C.-M. et al. (2002) "Phosphorylation of Bruton's tyrosine kinase by c-Abl," *Biochemical and Biophysical Research Communications* 299(3), 510-515.
Baselga, J. (2006) "Targeting Tyrosine Kinases in Cancer: The Second Wave," *Science* 312(5777), 1175-1178.
Behmoaram, E. et al. (2008) "Focal Adhesion Kinase-Related Proline-Rich Tyrosine Kinase 2 and Focal Adhesion Kinase Are Co-Overexpressed in Early-Stage and Invasive ErbB-2-Positive Breast Cancer and Cooperate for Breast Cancer Cell Tumorigenesis and Invasiveness," *American Journal of Pathology* 173(5), 1540-1550.
Bissell, M. J. et al. (2001) "Putting tumours in context," *Nature Reviews Cancer* 1(1), 46-54.

(Continued)

*Primary Examiner* — Brian Whiteman
(74) *Attorney, Agent, or Firm* — Medlen & Carroll, LLP

(57) ABSTRACT

Receptor protein kinases (RPTKs) transmit extracellular signals across the plasma membrane to cytosolic proteins, stimulating formation of complexes that regulate key cellular functions. Over half of the known tyrosine kinases are implicated in human cancers and are therefore highly promising drug targets. A large-scale loss-of-function analysis of tyrosine kinases using RNA interference in the clinically relevant ErbB2 positive, BT474 breast cancer cell line showed that Bruton's tyrosine kinase (BTK), a cytosolic, non-receptor tyrosine kinase that has been extensively studied for its role in B cell development, is required, in altered form, for BT474 breast cancer survival. This alternative form contains an amino-terminal extension that is also present in tumorigenic breast cells at significantly higher levels than in normal breast cells.

22 Claims, 22 Drawing Sheets

(56) References Cited

OTHER PUBLICATIONS

Figure 1:
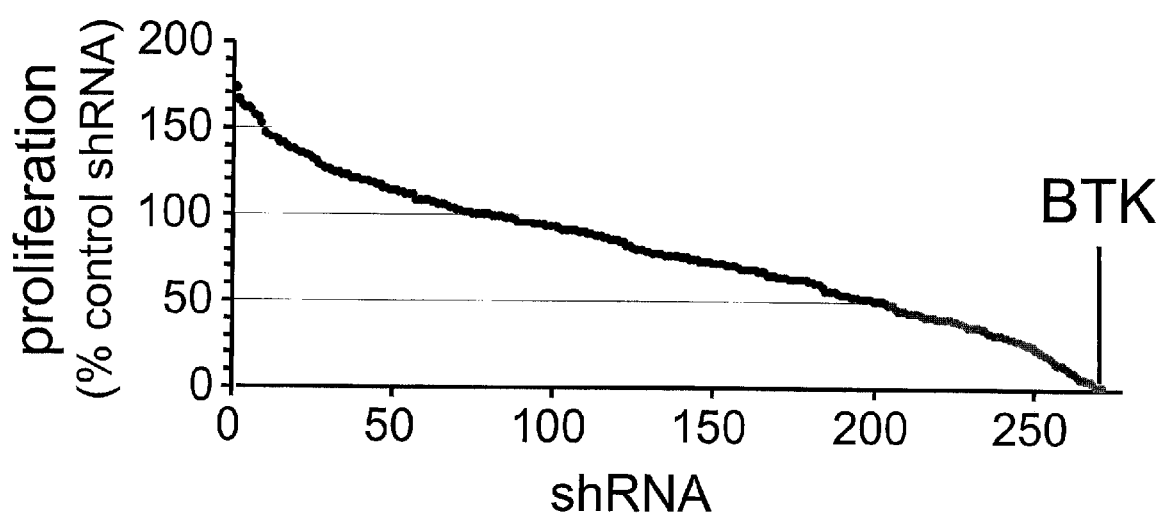

Blume-Jensen, P. et al. (2001) "Oncogenic kinase signalling," *Nature* 411(6835), 355-365.
Brantley-Sieders, D. M. et al. (2005) "Impaired tumor microenvironment in EphA2-deficient mice inhibits tumor angiogenesis and metastatic progression," *FASEB Journal*. pp. 1884-1886.
Call, J. A. et al. (2008) "Targeted manipulation of apoptosis in cancer treatment," *Lancet Oncology* 9(10), 1002-1011.
Cameron, H. L. et al. (2008) "Dieldrin promotes resistance to anoikis in breast cancer cells in vitro," *Reproductive Toxicology* 25(2), 256-262.
Cha, J. Y. et al. (2008) "Involvement of Fibroblast Growth Factor Receptor 2 Isoform Switching in Mammary Oncogenesis," *Molecular Cancer Research* 6(3), 435-445.
Chan, S. et al. (2006) "The Role of the Epidermal Growth Factor Receptor in Breast Cancer," *Journal of Mammary Gland Biology and Neoplasia* 11(1), 3-11.
Chu, D. et al. (2008) "Novel therapies in breast cancer: what is new from ASCO 2008," *Journal of Hematology and Oncology* 1(1), 1-13.
Dai, B. et al. (2006) "Tyrosine Kinase Etk/BMX Is Up-regulated in Human Prostate Cancer and Its Overexpression Induces Prostate Intraepithelial Neoplasia in Mouse," *Cancer Research* 66(16), 8058-8064.
Davuluri, R. V. et al. (2008) "The functional consequences of alternative promoter use in mammalian genomes," *Trends in Genetics* 24(4), 167-177.
Desmedt, C. et al. (2007) "Strong Time Dependence of the 76-Gene Prognostic Signature for Node-Negative Breast Cancer Patients in the TRANSBIG Multicenter Independent Validation Series," *Clinical Cancer Research* 13(11), 3207-3214.
Donjerkovic, D. et al. (2000) "Activation-induced cell death in B lymphocytes," *Cell Research* 10(3), 179-192.
Down, T. A. et al. (2002) "Computational Detection and Location of Transcription Start Sites in Mammalian Genomic DNA," *Genome Research* 12(3), 458-461.
Eckert, L. B. et al. (2004) "Involvement of Ras Activation in Human Breast Cancer Cell Signaling, Invasion, and Anoikis," *Cancer Research* 64(13), 4585-4592.
Farquhar, D. et al. (1991) "Doxorubicin analogs incorporating chemically reactive substituents," *Journal of Medicinal Chemistry* 34(2), 561-564.
Giamas, G. et al. (2010) "Kinases as targets in the treatment of solid tumors," *Cellular Signalling* 22(7), 984-1002.
Gomes, I. M. et al. (2012) "STEAP Proteins: From Structure to Applications in Cancer Therapy," *Molecular Cancer Research* 10(5), 573-587.
Griffiths-Jones, S. (2004) "The microRNA Registry," *Nucleic Acids Research* 32(suppl 1), D109-D111.
Hannon, G. J. et al. (1999) "MaRX: An Approach to Genetics in Mammalian Cells," *Science* 283(5405), 1129-1130.
Harada, N. et al. (1993) "Tissue-specific expression of the human aromatase cytochrome P-450 gene by alternative use of multiple exons 1 and promoters, and switching of tissue-specific exons 1 in carcinogenesis," *Proceedings of the National Academy of Sciences* 90(23), 11312-11316.
Hardwicke, J. et al. (2008) "Epidermal Growth Factor Therapy and Wound Healing—Past, Present and Future Perspectives," *Surgeon (Edinburgh University Press)* 6(3), 172-177.
Hofmann, W.-K. et al. (2002) "Relation between resistance of Philadelphia-chromosome-positive acute lymphoblastic leukaemia to the tyrosine kinase inhibitor STI571 and gene-expression profiles: a gene-expression study," *Lancet* 359(9305), 481-486.
Honigberg, L. A. et al. (2010) "The Bruton tyrosine kinase inhibitor PCI-32765 blocks B-cell activation and is efficacious in models of autoimmune disease and B-cell malignancy," *Proceedings of the National Academy of Sciences* 107(29), 13075-13080.
Hunter, D. J. et al. (2007) "A genome-wide association study identifies alleles in FGFR2 associated with risk of sporadic postmenopausal breast cancer," *Nature Genetics* 39(7), 870-874.
Irish, J. M. et al. (2006) "Altered B-cell receptor signaling kinetics distinguish human follicular lymphoma B cells from tumor-infiltrating nonmalignant B cells," *Blood* 108(9), 3135-3142.
Jiang, X. et al. (2007) "Activation of Nonreceptor Tyrosine Kinase Bmx/Etk Mediated by Phosphoinositide 3-Kinase, Epidermal Growth Factor Receptor, and ErbB3 in Prostate Cancer Cells," *Journal of Biological Chemistry* 282(45), 32689-32698.
Karnoub, A. E. et al. (2007) "Mesenchymal stem cells within tumour stroma promote breast cancer metastasis," *Nature* 449(7162), 557-563.
Kimura, K. et al. (2006) "Diversification of transcriptional modulation: Large-scale identification and characterization of putative alternative promoters of human genes," *Genome Research* 16(1), 55-65.
Klein, R. (2004) "Eph/ephrin signaling in morphogenesis, neural development and plasticity," *Current Opinion in Cell Biology* 16(5), 580-589.
Knudsen, S. (1999) "Promoter2.0: for the recognition of PoIII promoter sequences," *Bioinformatics* 15(5), 356-361.
Kourtidis, A. et al. (2007) "RNAi applications in target validation," *Ernst Schering Foundation Symposium Proceedings*(61), 1-21.
Krause, D. S. et al. (2005) "Tyrosine Kinases as Targets for Cancer Therapy," *New England Journal of Medicine* 353(2), 172-187.
Kris, M. G. et al. (2003) "Efficacy of gefitinib, an inhibitor of the epidermal growth factor receptor tyrosine kinase, in symptomatic patients with non—small cell lung cancer: A randomized trial," *JAMA: The Journal of the American Medical Association* 290(16), 2149-2158.
Kullander, K. et al. (2002) "Mechanisms and functions of eph and ephrin signalling," *Nature Reviews Molecular Cell Biology* 3(7), 475-486.
Kuppers, R. (2005) "Mechanisms of B-cell lymphoma pathogenesis," *Nature Reviews Cancer* 5(4), 251-262.
Levy, S. et al. (2007) "The Diploid Genome Sequence of an Individual Human," *PLoS Biology* 5(10), e254.
Li, T. W.-H. et al. (2006) "Wnt Activation and Alternative Promoter Repression of LEF1 in Colon Cancer," *Molecular and Cellular Biology* 26(14), 5284-5299.
Lin, L. et al. (2009) "Activation Loop Phosphorylation Modulates Bruton's Tyrosine Kinase (Btk) Kinase Domain Activity," *Biochemistry* 48(9), 2021-2032.
Lindvall, J. M. et al. (2005) "Bruton's tyrosine kinase: cell biology, sequence conservation, mutation spectrum, siRNA modifications, and expression profiling," *Immunological Reviews* 203(1), 200-215.
Lo, H.-W. et al. (2006) "EGFR signaling pathway in breast cancers: from traditional signal transduction to direct nuclear translocalization," *Breast Cancer Research and Treatment* 95(3), 211-218.
Mackeigan, J. P. et al. (2005) "Sensitized RNAi screen of human kinases and phosphatases identifies new regulators of apoptosis and chemoresistance," *Nature Cell Biology* 7(6), 591-600.
Matys, V. et al. (2003) "TRANSFAC®: transcriptional regulation, from patterns to profiles," *Nucleic Acids Research* 31(1), 374-378.
Merlos-Suárez, A. et al. (2008) "Eph—ephrin signalling in adult tissues and cancer," *Current Opinion in Cell Biology* 20(2), 194-200.
Mohamed, A. J. et al. (2009) "Bruton's tyrosine kinase (Btk): function, regulation, and transformation with special emphasis on the PH domain," *Immunological Reviews* 228(1), 58-73.
Nahta, R. et al. (2006) "HER2 therapy: Molecular mechanisms of trastuzumab resistance," *Breast Cancer Research* 8(6), 1-8.
Noren, N. K. et al. (2004) "Eph receptor—ephrin bidirectional signals that target Ras and Rho proteins," *Cellular Signalling* 16(6), 655-666.
Ogawa, K. et al. (2000) "The ephrin-A1 ligand and its receptor, EphA2, are expressed during tumor neovascularization," *Oncogene* 19(52), 6043-6052.
Paddison, P. J. et al. (2004) "A resource for large-scale RNA-interference-based screens in mammals," *Nature* 428(6981), 427-431.
Park, C. C. et al. (2000) "The influence of the microenvironment on the malignant phenotype," *Molecular Medicine Today* 6(8), 324-329.
Penault-Llorca, F. et al. (1995) "Expression of FGF and FGF receptor genes in human breast cancer," *International Journal of Cancer* 61(2), 170-176.
Prévost, N. et al. (2002) "Interactions between Eph kinases and ephrins provide a mechanism to support platelet aggregation once

(56) References Cited

OTHER PUBLICATIONS cell-to-cell contact has occurred," *Proceedings of the National Academy of Sciences* 99(14), 9219-9224.

Prevost, N. et al. (2003) "Contact-dependent signaling during the late events of platelet activation," *Journal of Thrombosis and Haemostasis* 1(7), 1613-1627.

Prévost, N. et al. (2005) "Eph kinases and ephrins support thrombus growth and stability by regulating integrin outside-in signaling in platelets," *Proceedings of the National Academy of Sciences of the United States of America* 102(28), 9820-9825.

Prévost, N. et al. (2004) "Signaling by ephrinB1 and Eph kinases in platelets promotes Rap 1 activation, platelet adhesion, and aggregation via effector pathways that do not require phosphorylation of ephrinB1," *Blood* 103(4), 1348-1355.

Qin, D.-n. et al. (2011) "Monoclonal antibody to six transmembrane epithelial antigen of prostate-4 influences insulin sensitivity by attenuating phosphorylation of P13K (P85) and Akt: Possible mitochondrial mechanism," *Journal of Bioenergetics and Biomembranes* 43(3), 247-255.

Qiu, Y. et al. (2000) "Signaling network of the Btk family kinases," *Oncogene* 19(49), 5651-5661.

Radvanyi, L. et al. (2005) "The gene associated with trichorhinophalangeal syndrome in humans is overexpressed in breast cancer," *Proceedings of the National Academy of Sciences of the United States of America* 102(31), 11005-11010.

Ruschel, A. et al. (2004) "Protein tyrosine kinase Syk modulates EGFR signalling in human mammary epithelial cells," *Cellular Signalling* 16(11), 1249-1261.

Sabatier, R. et al. (2011) "Kinome expression profiling and prognosis of basal breast cancers," *Molecular Cancer* 10(1), 86.

Sabbah, M. et al. (2008) "Molecular signature and therapeutic perspective of the epithelial-to-mesenchymal transitions in epithelial cancers," *Drug Resistance Updates* 11(4-5), 123-151.

Serra, V. et al. (2008) "NVP-BEZ235, a Dual PI3K/mTOR Inhibitor, Prevents PI3K Signaling and Inhibits the Growth of Cancer Cells with Activating PI3K Mutations," *Cancer Research* 68(19), 8022-8030.

Shepard, H. M. et al. (2008) "Signal integration: a framework for understanding the efficacy of therapeutics targeting the human EGFR family," *Journal of Clinical Investigation* 118(11), 3574-3581.

Shinohara, M. et al. (2008) "Tyrosine Kinases Btk and Tec Regulate Osteoclast Differentiation by Linking RANK and ITAM Signals," *Cell* 132(5), 794-806.

Silva, J. M. et al. (2005) "Second-generation shRNA libraries covering the mouse and human genomes," *Nature Genetics* 37(11), 1281-1288.

\* cited by examiner

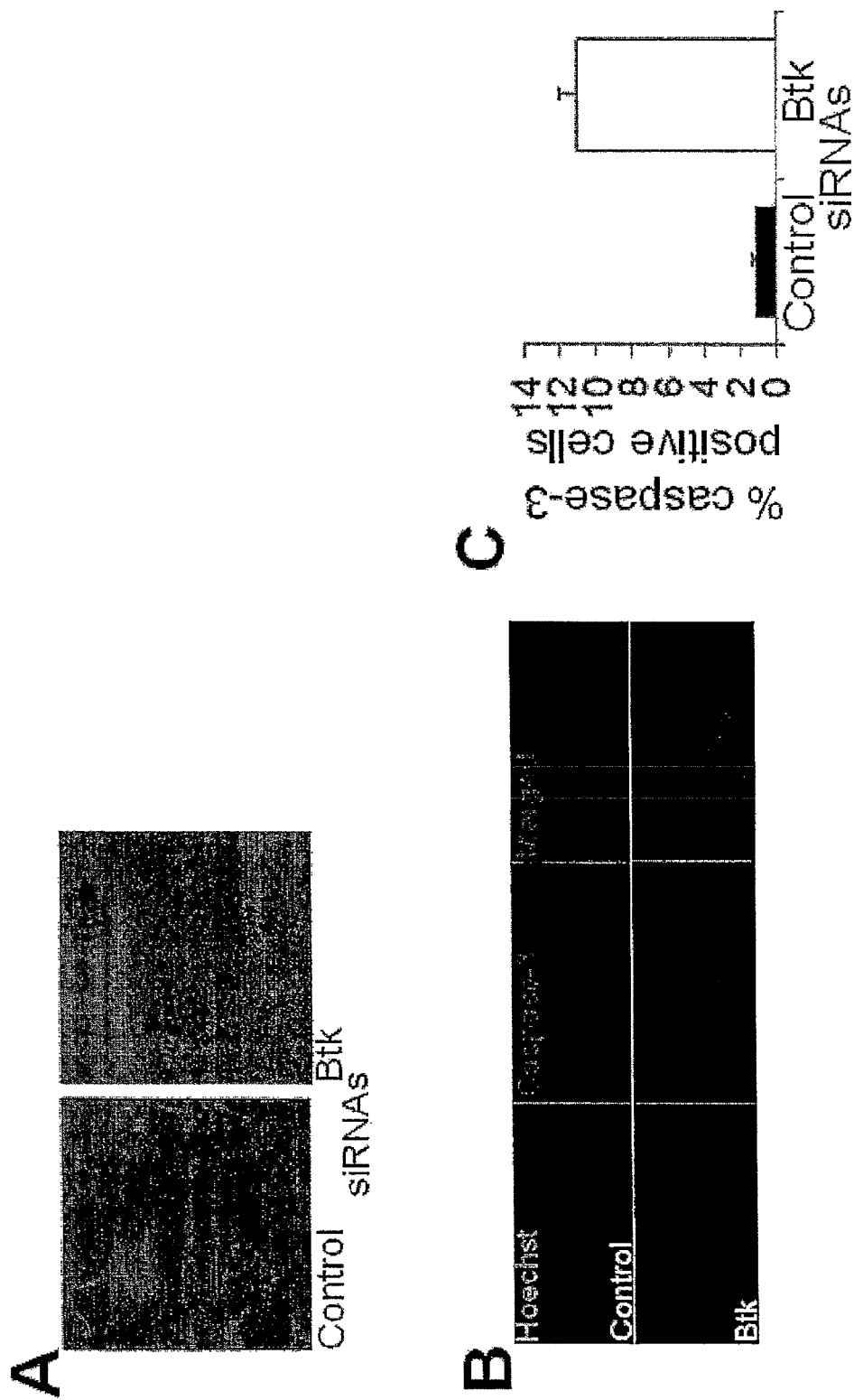
Figure 2 a - c

A

Btk-Cra-A ACTCAAGATAGTAGTGTCAGAGGTCCGAACCAAATGAAGGGCGGGGACAGTTGAGGGGGT 60  SEQ ID NO. 1
Btk-Cra-C -CTTTATCTCTTT-TGCTGGACTCTGCTACGTAGTGGCGTTCAGTGAAGGGAGCAGTGTT 58  SEQ ID NO. 2

Btk-Cra-A GGAATAGGGAC-----GGCAGCAGGGAACCAGATAGCATGCTG--CTGAGAAGAAAAAAG 114
Btk-Cra-C TTTCCAGATGCTCTGTACCTGCCGGTCCCCGAGGGAGCCAGGACTAGGGTCGAATGAAG 118

Btk-Cra-A ACATTGGTTTAGGTCAGAAACCAAAAAAAGGGGAACTGAGTGCTCTGAAAGGGTGGGTT 174
Btk-Cra-C GGGTCCTGCAGGTCCAGGGTTCCATTCCTGTTCCACCTCAAGGTCACTGG-GAACACCTTT 177

Btk-Cra-A TGCT-CAGAGTGTCCTTGCTGTCTGGACTGTAAGGATATGTCTCCAGGGCCAGTGTCTGC 233
Btk-Cra-C GGCAGGCAAACTG--CTAATTCAATGAAGACCTGGAGGGAGCCAATTGTTCCAGTTCATCT 236

Btk-Cra-A TGCG-ATCGAGTGCCACGTTGCAAGTCCTGGCATCTCAATGCATCTGGAAAGCTACCTCC 292
Btk-Cra-C ATCAC▒GCCAGTTGGTCCATTCAACAA▒GTTATTGGATGCCATTATGTGCAGGC 295

BTK-Cra-C  M  A  S  W  I  Q  Q  M  Y  I  G  C  P  L  C  G  R  N  SEQ ID NO. 3
                                                          →

Btk-Cra-A ATTAAGTCAGGACT▒▒▒▒▒▒▒▒▒▒▒▒▒▒▒▒▒▒▒▒▒▒▒▒▒▒▒▒▒▒▒▒▒▒▒▒▒▒▒▒ 352
Btk-Cra-C ACTGTTCCGGGGGA▒▒▒▒▒▒▒▒▒▒▒▒▒▒▒▒▒▒▒▒▒▒▒▒▒▒▒▒▒▒▒▒▒▒▒▒▒▒▒▒ 335

BTK-Cra-C  C  S  Q  G  S  S  T  G  S  L  Q  K  E  A  M  A  A  V  I

Btk-Cra-A ▒▒▒▒▒▒▒▒▒▒▒▒▒▒▒▒▒▒▒▒▒▒▒▒▒▒▒▒▒▒▒▒▒▒▒▒▒▒▒▒▒▒▒▒▒▒▒
Btk-Cra-C ▒▒▒▒▒▒▒▒▒▒▒▒▒▒▒▒▒▒▒▒▒▒▒▒▒▒▒▒▒▒▒▒▒▒▒▒▒▒▒▒▒▒▒▒▒▒▒

BTK-Cra-C  L  E  S  I  P  L  K  R  S  Q  K  K  R

B
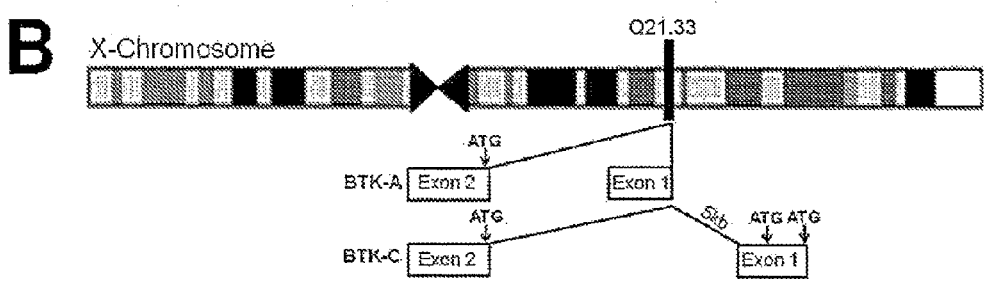

C
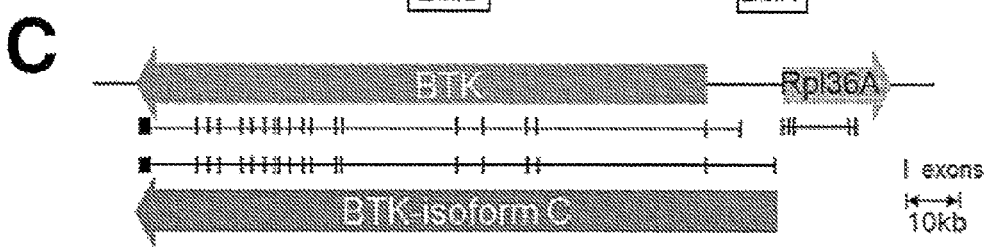

Figure 3a-c

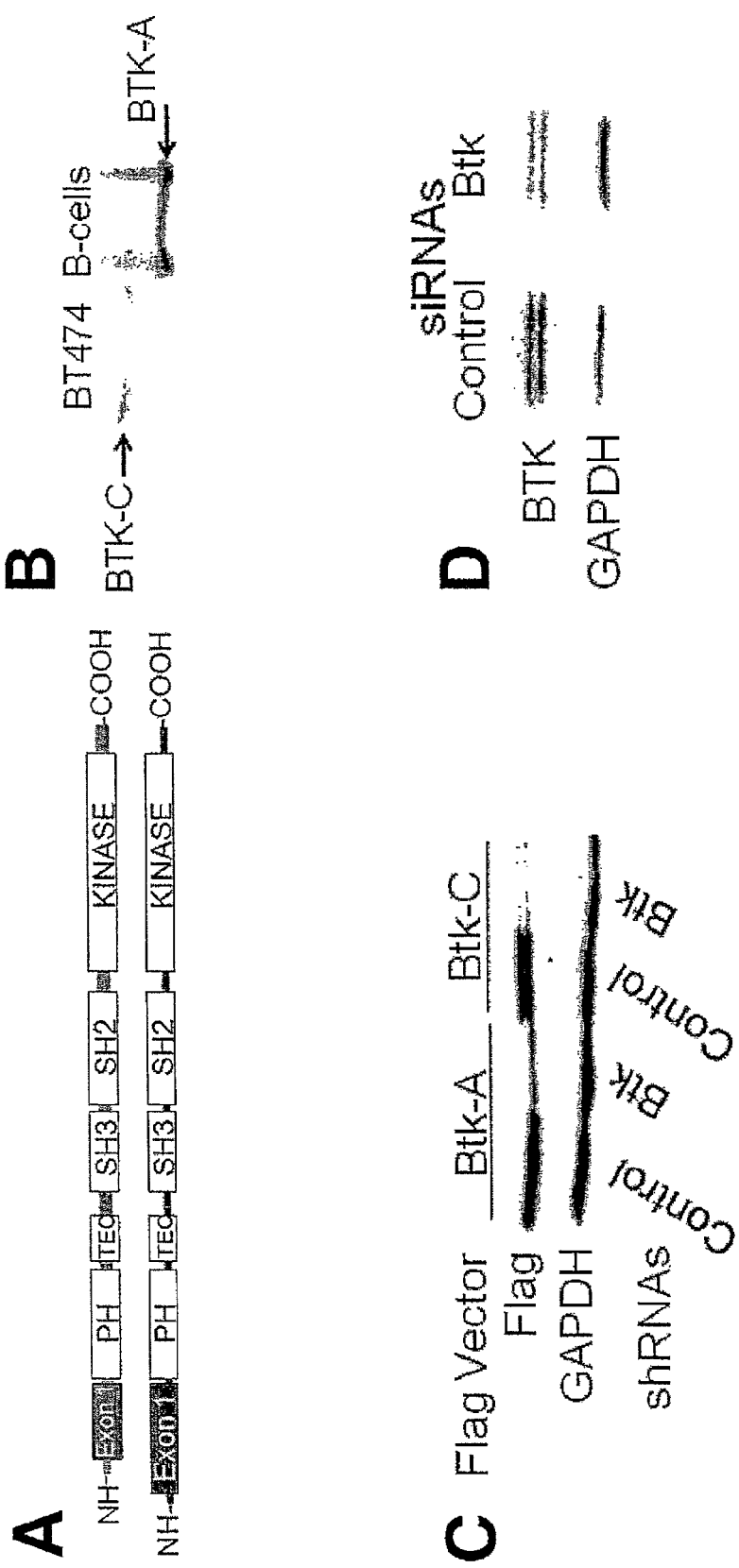
Figure 4 a-d

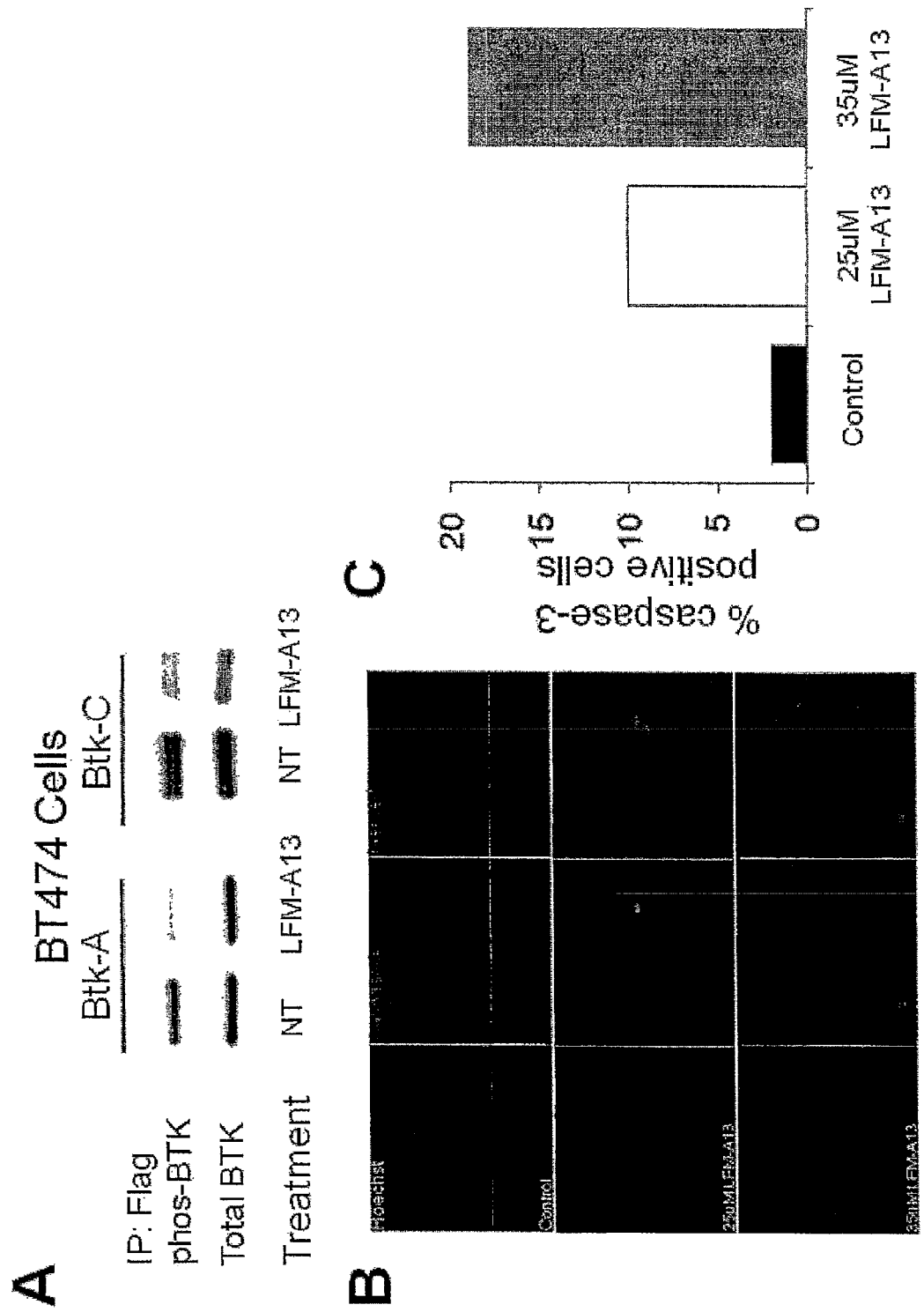
Figure 5 a-c

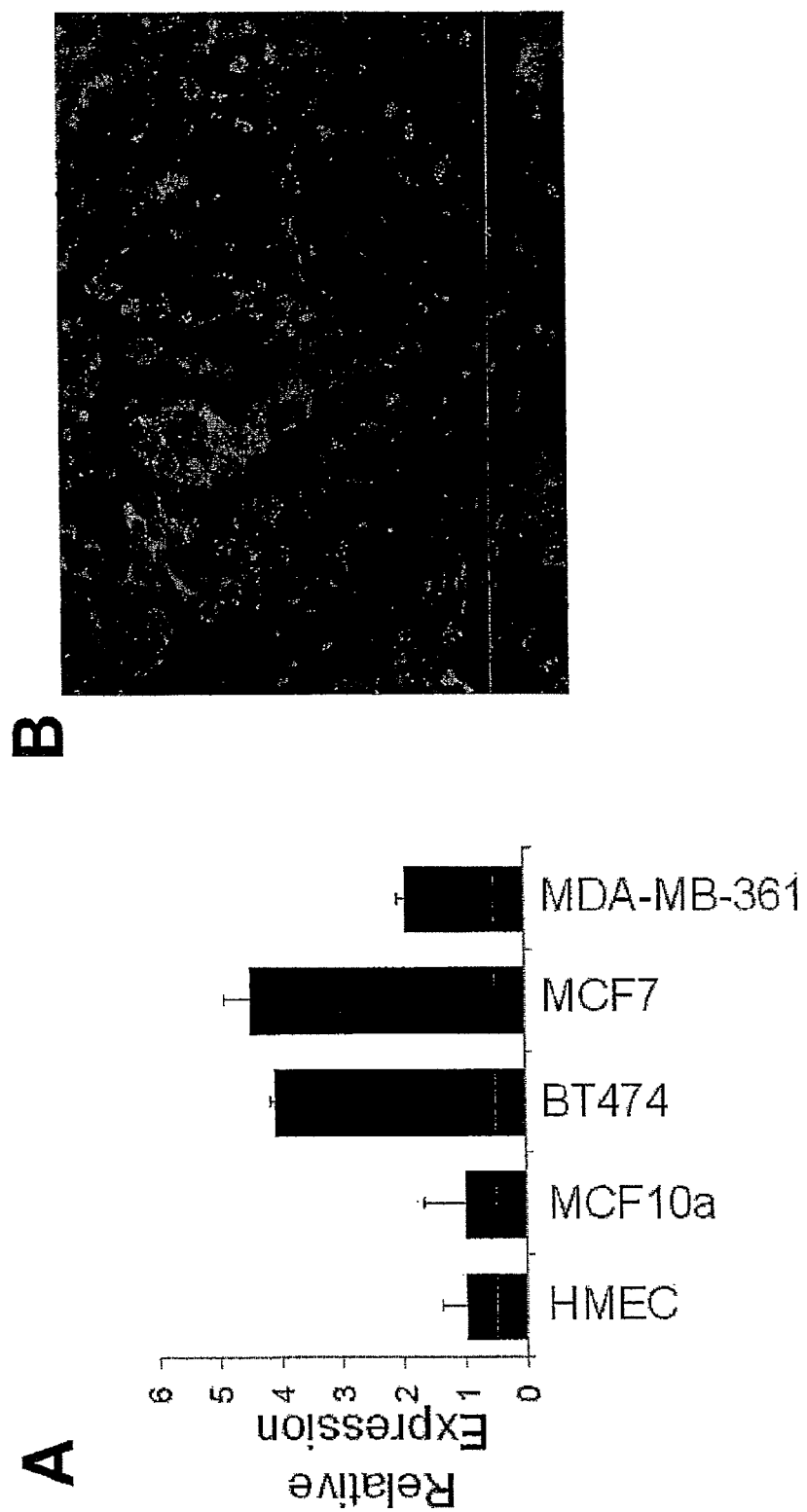
Figure 7 a & b

A

```
Btk-A ACTCAAGATAGTAGTGTCAGAGGTCCCAACCAAATGAAGGGCGGGGACAGTTGAGGGGGT 60    SEQ ID NO: 1
Btk-C -CTTTATCTCTTT-TGGTGGACTCTGCTACGTAGTGGCGTTCAGTGAAGGGAGCAGTGTT 58    SEQ ID NO: 2

Btk-A GGAATAGGGAC----GGCAGCAGGGAACCAGATAGCATGCTG---CTGAGAAGAAAAAAG 114
Btk-C TTTCCCAGATCCTCTGGCCTCCCCGTCCCCGAGGGAAGCCAGGACTAGGGTCGAATGAAG 118

Btk-A ACATTGGTTTAGGTCAGGAACCAAAAAAAGGGAACTGAGTGGCTGTGAAAGGGTGGGGTT 174
Btk-C GGGTCCTCCACCTCCACGTTCCATTCCTGTTCCACCTCAAGGTCACTGG-GAACACCTTT 177

Btk-A TGCT-CAGACTGTCCTTCCTCTCTGGACTGTAAGAATATGTCTCCAGGGCCAGTGTCTGC 233
Btk-C CGCAGCAAACTG--CTAATTCAATGAAGACCTGGAGGGAGCCAATTGTTCCAGTTCATCT 235

Btk-A TGCG-ATCGAGTCCCACCTTCCAAGTCCTGGCATCTCAATGCATCTGGGAAGCTACCTGC 292
Btk-C ATCAC▓▓GCCAGTTGGTCCATTCAACAA▓▓GTTATTGGATGCCCATTATGTGGCAGGC 295

BTK-C          M   A  S  W  S  I  Q  Q  M  V  I  G  C  P  L  C  G  R  H    SEQ ID NO: 3

Btk-A ATTAAGTCAGGACT▓▓▓▓▓▓▓▓▓▓▓▓▓▓▓▓▓▓▓▓▓▓▓▓▓▓▓▓▓▓ 352
Btk-C ACTGTTCCGGGGA▓▓▓▓▓▓▓▓▓▓▓▓▓▓▓▓▓▓▓▓▓▓▓▓▓▓▓▓▓▓▓ 355

BTK-C  C  S  G  G  E  H  T  G  E  L  Q  K  E  E  A  M  A  A  V  I

Btk-A ▓▓▓▓▓▓▓▓▓▓▓▓▓▓▓▓▓▓▓▓▓▓▓▓▓▓▓▓▓▓▓▓▓▓▓
Btk-C ▓▓▓▓▓▓▓▓▓▓▓▓▓▓▓▓▓▓▓▓▓▓▓▓▓▓▓▓▓▓▓▓▓▓▓

BTK-C  L  E  S  I  F  L  K  R  S  Q  Q  K  K  K
```

B

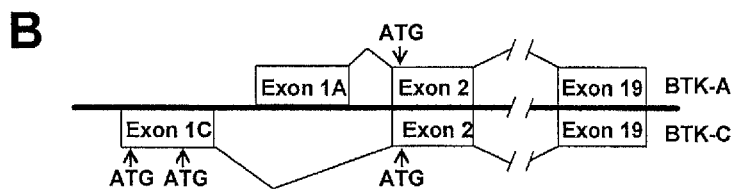

C

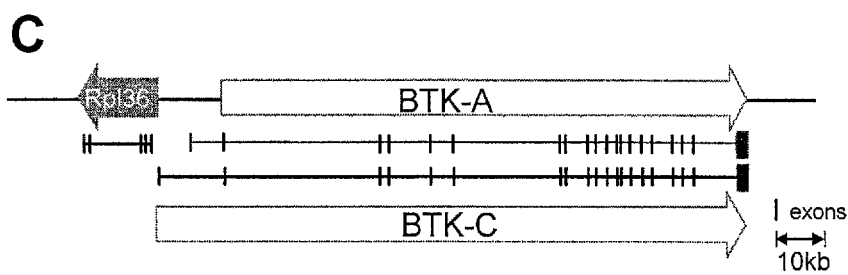

FIG 11

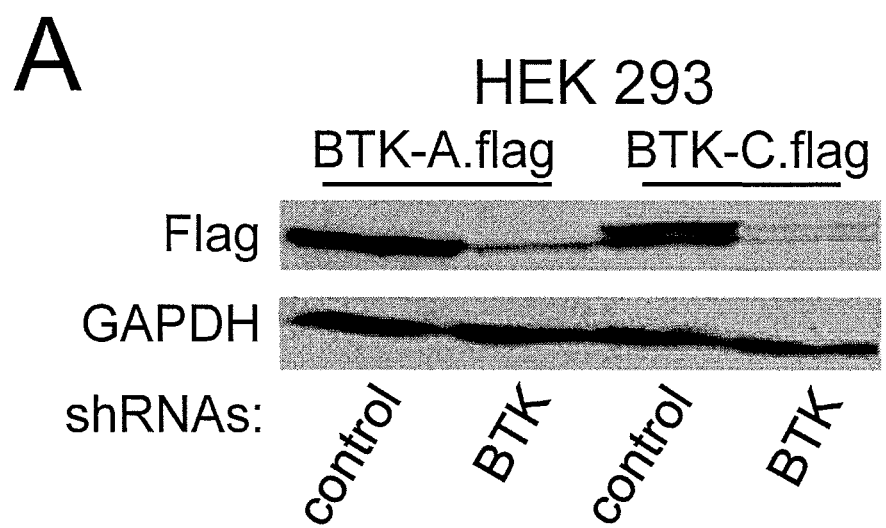
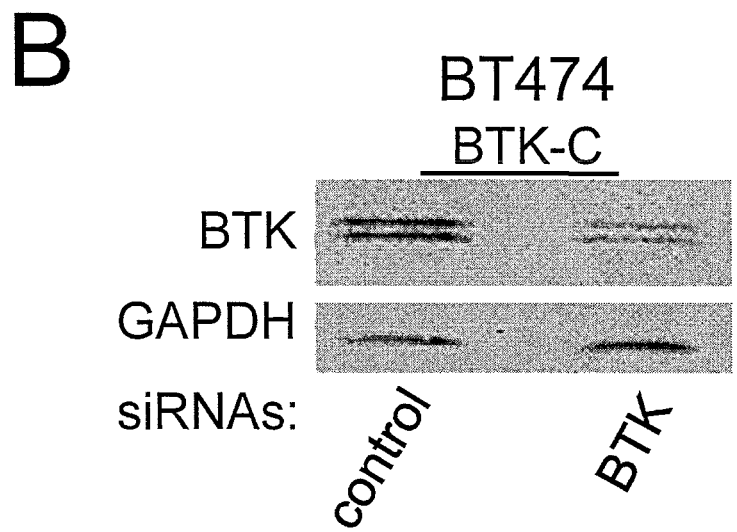
FIG 17

| | | | |
|---|---|---|---|
| SEQ ID NO: 34 | EGFR | 1 | LRILKETEFKKIKVLGSGAFGTVYKGLWIPEGEKVKIPVAIKELREATSPKANKEILDEAYVMASVDNPHVCRLLGICLT 80 |
| SEQ ID NO: 35 | ERBB2 | 1 | ---------RKVKVLGSGAFGTVYKGIWIPDGENVKIPVAIKVLRENTSPKANKEILDEAYVMAGVGSPYVSRLLGICLT 71 |
| SEQ ID NO: 36 | ERBB3 | 1 | ---------RKLKVLGSGVFGTVHKGVWIPEGESIKIPVCIKVIEDKSGRQSFQAVTDHMLAIGSLDHAHIVRLLGLCPG 71 |
| SEQ ID NO: 37 | ERBB4 | 1 | ---------KRVKVLGSGAFGTVYKGIWVPEGETVKIPVAIKILNETTGPKANVEFMDEALIMASMDHPHLVRLLGVCLS 71 |
| SEQ ID NO: 38 | BTK | 1 | ---------TFLKELGTGQFGVVRYGKW-----RGQYDVAIKMIKEGS--MSEDEFIEEAKVMMNLSHEKLVQLYGVCTK 64 |

```
EGFR   81  S-TVQLITQLMPFGCLLDYVREHKDNIGSQYLLNWCQIAKGMNYLEDRRLVHRDLAARNVLVKTPQHVKITDFGLAKLL  159
ERBB2  72  S-TVQLVTQLMPYGCLLDHVRENRGRLGSQDLLNWCMQIAKGMSYLEDVRLVHRDLAARNVLVKSPNHVKITDFGLARLL  150
ERBB3  72  S-SLQLVTQYLPLGSLLDHVRQHRGALGPQLLLNWGVQIAKGMNYLEEHGMVHRNLAARNVLLKSPSQVQVADFGVADLL  150
ERBB4  72  P-TIQLVTQLMPHGCLLEYVHEHKDNIGSQLLLNWCVQIAKGMNYLEERRLVHRDLAARNVLVKSPNHVKITDFGLARLL  150
BTK    65  QRPIFIITEYMANGCLLNYLREMHPRHFQTQQLLEMCKDVCEAMEYLESKQFLHRDLAARNCLVNDQGVVKVSDFGLSRYV 144

EGFR  160  GAEEKEYHAEGGKVPIKWMALESILHRIYTHQSDVWSYGVTVWELMTFGSKPYDGIPASEISSILEKGERLPQPPICTID  239
ERBB2 151  DIDETEYHADGGKVPIKWMALESILRRRFTHQSDVWSYGVTVWELMTFGAKPYDGIPAREIPDLLEKGERLPQPPICTID  230
ERBB3 151  PPDDKQLLYSEARTPIKWMALESIHFGKYTHQSDVWSYGVTVWELMTFGAEPYAGLRLAEVPDLLEKGERLAQPQICTID  230
ERBB4 151  EGDEKEYHADGGKMPIKWMALECIHYRKFTHQSDVWSYGVTIWELMTFGGKPYDGIPTREIPDLLEKGERLPQPPICTID  230
BTK   145  -LDDEYTSSVGSKFPVRWSPPEVLHYSKFSSKSDIWAFGVLMWEIYSLGKMPYERFTNSETAEHIAQGLRLYRPHLASEK  223

EGFR  240  VYMIMVKCWMIDADSRPKFRELIIEFSKMARDPQRYLVIQGDERMHLPSPTDSNFYRALMDEEDMDDVVDADEYLIP    316
ERBB2 231  VYMIMVKCWMIDSECRPRFRELVSEF----------------------------------------------------  256
ERBB3 231  VYHVMVKCWMIDENIRPTFKELANEF----------------------------------------------------  256
ERBB4 231  VYMVMV------------------------------------------------------------------------  236
BTK   224  VYTIMYSCWHEKADERPTFKILLSNI----------------------------------------------------  249
```

The ability of PCI-32765 to block ERRB2 (HER2/neu) activation in breast cancer cells may be due to similarities with the BTK active site. EGFR family members EGFR, ERBB2 and ERRB4 share the PCI-32765-targeted cysteine residue found in BTK (boxed).

| | | | |
|---|---|---|---|
| SEQ ID NO: 39 | PDGFa | 1 | YEIRWRVIESISPDGHEYIYVDPMQLPYDSRWEFPRDGLVLGRVLGSGAFGKVVEGTAYGLSRSQP--VMKVAVKMLKPT 78 |
| SEQ ID NO: 40 | FGFR1 | 1 | ------------------------------------------LVLGKPLGEGCFGQVVLAEAIGLDKDKPNRVTKVAVKMLKSD 42 |
| SEQ ID NO: 41 | SRC | 1 | ------------------------------------------LRLEVKLGQGCFGEVWMGTWNG--------TTRVAIKTLKPG 34 |
| SEQ ID NO: 42 | MET | 1 | ------------------------------------------EVIGRGHFGCVYHGTLL----DNDGKKIHCAVKSLNRI 34 |
| SEQ ID NO: 43 | BTK | 1 | ------------------------------------------TFLKELGTGQFGVVKYGKWRG--------QYDVAIKMIKEG 33 |

```
PDGFa  79  ARSSEKQALMSELKIMTHLGPHLNIVNLLGACTK-SGPIYIITEYCFYGDVNYLHKNRDSFLSHHPEKPKKELDIFGLN  157
FGFR1  43  ATEKDLSDLISEMEMMKMIGKHKNIINLLGACTQ-DGPLYVIVEYASKGNLREYLQARRPPGLEYCYNP----------  110
SRC    35  TMSPE--AFLQEAQVMKKLR-HEKLVQLYAVVSE-E-PIYIVTEYMSKGSLDFLKG-----------------------  86
MET    35  TDIGEVSQFLTEGIIMKDFS-HPNVLSLLGICLRSEGSPLVVLPYMKHGDRNFIR--------NE-------------  91
BTK    34  SMSED--EFIEEAKVMMNLS-HEKLVQLYGVCTK-QRPIFIITEYMANGCLNYLREMR---------------------  88

PDGFa 158  PADESTRSYVILSFENNGDYMDMKQADTTQYVPMLERKEVSKYSDIQRSLYDRPASYKKKSMLDSEVKNLLSDDNSEGLT  237
FGFR1 111  -------------------------------------------------------------------SHNPEEQLS    119
SRC   87  -------------------------------------------------------------------ETGKYLR     93
MET   92  -------------------------------------------------------------------THNP----T   96
BTK   89  -------------------------------------------------------------------HRFQ        92

PDGFa 238  LLDLLSFTYQVARGMEFLASKNCVHRDLAARNVLLAQGKIVKICDFGLARDIMHDSNYVS---KGSTFLPVKWMAPESIF  314
FGFR1 120  SKDLVSCAYQVARGMEYLASKKCIHRDLAARNVLVTEDNVMKIADFGLARDI-HHIDYYK--KTTNGRLPVKWMAPEALF  196
SRC   94   LPQLVDMAAQIASGMAYVERMNYVHRDLRAANILVGENLVCKVADFGLARLI-EDNEYTA---RQGAKFPIKWTAPEAAL  169
MET   97   VKDLIGFGLQVAKGMKYLASKKFVHRDLAARNCMLDEKFTVKVADFGLARDM-YDKEYYSVHNKTGAKLPVKWMALESLQ  175
BTK   93   TQQLLEMCKDVCEAMEYLESKQFLHRDLAARNCLVNDQGVVKVSDFGLSRYV-LDDEYTS---SVGSKFPVRWSPPEVLM  168

PDGFa 315  DNLYTTLSDVWSYGILLWEIFSLGGTPYPGMMVDSTFYNKIKSGYRMAKPDHATSEVYEIMVKCWNSEPEKRPSFYH---  391
FGFR1 197  DRIYTHQSDVWSFGVLLWEIFTLGGSPYPGV-PVEELFKLLKEGHRMDKPSNCTNELYMMMRDCWHAVPSQRPTFKQLVE  275
SRC   170  YGRFTIKSDVWSFGILLTELTTKGRVPYPGM-VNREVLDQVERGYRMPCPPECPESLHDLMCQCWRKEPEERPTFEYLQA  248
MET   176  TQKFTTKSDVWSFGVLLWELMTRGAPPYPDV-NTFDITVYLLQGRRLLQPEYCPDPLYEVMLKCWHPKAEMRPSFSELVS  254
BTK   169  YSKFSSKSDIWAFGVLMWEIYSLGKMPYERF-TNSETAEHIAQGLRLYRPHLASEKVYTIMYSCWHEKADERPTFKILLS  247
```

Several other non TEC family kinases do not share the PCI-32765-targeted cysteine residue (boxed).

FIGURE 21

BRUTON'S TYROSINE KINASE AS ANTI-CANCER DRUG TARGET

This invention was made with government support by U.S. Army Medical Research Acquisition Activity grant DAMD17-02-1-0729 and NCI R01CA136658 to DSC. The government has certain rights in the invention.

FIELD

Embodiments of the invention find application in the field of cancer therapy.

BACKGROUND

Protein tyrosine kinases (PTKs) mediate the reversible process of tyrosine phosphorylation, providing the signals that activate or block signal transduction pathways that govern cell survival decisions and as such are tightly regulated. Genes that regulate extracellular growth, differentiation and developmental signals are commonly mutated in cancers. Perhaps it is not surprising therefore that PTKs comprise the largest group of dominant oncogenes. Thirty of the 58 receptor protein tyrosine kinases (RPTKs) have been implicated in human cancer (Blume-Jensen and Hunter, 2001). Less than half of the cytoplasmic protein tyrosine kinases have been associated with tumorigenesis, due not to a less critical role in signal transduction regulation, however, but from an experimental bias that has focused on viral counterparts to gain insight into potential transforming mechanisms (Blume-Jensen and Hunter, 2001).

In recent years there has been a surge in efforts to discover genes critical to cancer signaling pathways that when inhibited would provide specific anti-cancer therapies (Lu and Chu, 2008) (Sabbah et al., 2008). Trastuzumab, (Herceptin), a humanized monoclonal antibody that specifically inhibits the HER2/neu/ErbB-2 (hereafter referred to as ErbB-2) receptor tyrosine kinase, which is amplified and/or over-expressed in 25-30% of metastatic breast cancers, was the first targeted therapy to be approved by the FDA. As a single-agent monotherapy, however, the primary response rate to trastuzumab is low, (12% to 34%) and the rate of primary resistance high, between 66% to 88% (Nahta and Esteva, 2006). Notably, however, the time to disease progression, response rate and overall survival increase when trastuzumab is used in combination with paclitaxel or docetaxel (Nahta and Esteva, 2006). Indeed, recent successes in targeting molecules integral to survival pathways in combination with traditional chemotherapeutics has led to significant efforts to identify new drug targets that sensitize the breast cancer cell towards cell death (MacKeigan et al., 2005); (Call et al., 2008). Such additional drug targets, specific to or over-expressed in breast cancer cells compared to normal tissues, and known to be functionally relevant, are still needed, as are cancer-specific markers for use in detecting or diagnosing cancer.

SUMMARY

In one embodiment, the instant invention provides a method of treating cancer, comprising: a) providing a subject with cancer (e.g. breast cancer cells) and an inhibitor of a gene encoding a cytoplasmic tyrosine kinase, and b) treating said subject with said inhibitor. In a preferred embodiment, the cytoplasmic tyrosine kinase is a member of the Tec family of cytoplasmic tyrosine kinases and, in a more preferred embodiment, the cytoplasmic tyrosine kinase is Bruton's Tyrosine Kinase. In another embodiment, the cytoplasmic tyrosine kinase is a variant of Bruton's Tyrosine Kinase comprising an amino-terminal extension. The amino acid sequence of the variant is SEQ ID NO. 1. The amino-terminal extension is SEQ ID NO 2. In one embodiment the extension comprises an additional 34 amino acids. In one embodiment, the method of treating cancer comprises treating with an inhibitor that comprises an interfering RNA. Preferably, the treatment with the RNA results in reduced proliferation of the breast cancer cells. In one embodiment, the amino acid sequence of the variant and amino-terminal extension is SEQ ID NO. 3.

In one embodiment, the instant invention provides a method of diagnosing cancer, comprising: a) providing cells suspected to be breast cancer cells and a ligand capable of binding to a variant of Bruton's Tyrosine Kinase, said variant comprising an amino-terminal extension; b) contacting said cells with said ligand under conditions wherein said variant is detected. In one embodiment, the amino-terminal extension of the variant used to diagnose cancer comprises an additional 34 amino acids. In a preferred embodiment the ligand used binds to a portion of the 34 amino acid extension. In one embodiment, the ligand comprises an antibody or a fragment thereof.

In another embodiment, the invention provides a composition comprising a variant of Bruton's Tyrosine Kinase comprising an amino-terminal extension, the extension preferably comprising an additional 34 amino acids.

In another embodiment, the invention provides a ligand-protein complex comprising an antibody bound to the variant of Bruton's Tyrosine Kinase.

In yet another embodiment, the invention provides a kit for diagnosing cancer, the kit comprising a ligand capable of binding to a variant of Bruton's Tyrosine Kinase and instructions for its use.

In one embodiment, the present invention contemplates a composition comprising a purified variant of Bruton's Tyrosine Kinase comprising an amino-terminal extension. In one embodiment, the extension comprises an additional 34 amino acids. In one embodiment, the present invention contemplates a ligand-protein complex comprising antibody bound to the purified variant of Bruton's Tyrosine Kinase comprising an amino-terminal extension. In another embodiment, the variant comprises the amino acid sequence set forth in SEQ ID NO: 3. In yet another embodiment, the variant comprises an amino acid sequence at least 95% identical to SEQ ID NO: 3 that prevents apoptosis in a cancer cell.

In one embodiment, the present invention contemplates an isolated cDNA comprising SEQ ID NO: 2.

In one embodiment, the present invention contemplates an interfering double stranded RNA that is at least partially complementary to SEQ ID NO: 2 that inhibits expression of a protein encoded by SEQ ID NO: 2. In one embodiment, the present invention contemplates an interfering double stranded RNA (siRNA) having a sense strand comprising the nucleotide sequence 5'-GGU UAU UGG AUG CCC AUU AUU-3' (SEQ ID NO: 66). In one embodiment, the present invention contemplates an interfering double stranded RNA having an antisense strand comprising the nucleotide sequence 5'-UAA UGG GCA UCC AAU AAC CUU-3' (SEQ ID NO: 67). In one embodiment, the present invention contemplates an interfering double stranded RNA having a sense strand comprising the nucleotide sequence 5'-CAA CAA AUG GUU AUU GGA UUU-3' (SEQ ID NO: 68). In one embodiment, the present invention contemplates an interfering double stranded RNA having an antisense strand comprising the nucleotide sequence 5'-AUC CAA UAA CCAUUU GUU GUU-3' (SEQ ID NO: 69).

In one embodiment, the present invention contemplates an isolated antibody that specifically binds to the polypeptide of the amino acid sequence set forth in SEQ ID NO: 3. In another embodiment, the present invention contemplates an isolated antibody that specifically binds to the polypeptide of an amino acid sequence at least 95% identical to SEQ ID NO: 3. In yet another embodiment, the present invention contemplates an isolated antibody that specifically binds to a fragment of the amino acid sequence set forth in SEQ ID NO: 3. In a further embodiment, the fragment consists of the C-terminal amino acids of the amino acid sequence set forth in SEQ ID NO: 3. In still further embodiments, the fragment consists of the 34 C-terminal amino acids of the amino acid sequence set forth in SEQ ID NO: 3. In additional embodiments, the antibody is a monoclonal antibody. In yet another embodiment, the antibody is a humanized antibody. In yet another embodiment, the antibody is an antibody fragment. In yet another embodiment, the antibody is labeled.

In one embodiment, the present invention contemplates a method of treating cancer, comprising: a) providing: i) subject with cancer (e.g. breast cancer), ii) a chemotherapeutic agent, and iii) an inhibitor of a gene encoding a cytoplasmic tyrosine kinase; and b) treating said subject with said chemotherapeutic agent and said inhibitor. In one embodiment, the cytoplasmic tyrosine kinase is Bruton's Tyrosine Kinase. In one embodiment, the cytoplasmic tyrosine kinase is a variant of Bruton's Tyrosine Kinase comprising an amino-terminal extension. In another embodiment, the extension comprises an additional 34 amino acids. In one embodiment, the inhibitor comprises an interfering double stranded RNA. In one embodiment, the chemotherapeutic agent comprises Doxorubicin or analogues thereof. In another embodiment, treating with said chemotherapeutic agent and said inhibitor results in reduced proliferation of the breast cancer cells within said subject. In another embodiment, said interfering double stranded RNA comprises a sense strand having the nucleotide sequence of SEQ ID NO: 66. In another embodiment, said interfering double stranded RNA comprises an antisense strand having the nucleotide sequence of SEQ ID NO: 67. In yet another embodiment, said interfering double stranded RNA comprises a sense strand having the nucleotide sequence of SEQ ID NO: 68. In yet another embodiment, the interfering double stranded RNA comprises an antisense strand having the nucleotide sequence of SEQ ID NO: 69. In further embodiments, said inhibitor comprises a mixture of interfering double stranded RNAs comprising a sense strand having the nucleotide sequence of SEQ ID NOs: 66 and 68 and an antisense strand having the nucleotide sequence of SEQ ID NOs: 67 and 69. In additional embodiments, the chemotherapeutic agent includes, but is not limited to, AC (Adriamycin, cyclophosphamide), TAC (taxotere, AC), ABVD (Adriamycin, bleomycin, vinblastine, dacarbazine), BEACOPP (bleomycin, etoposide, Adriamycin, cyclophosphamide, vincristine, procarbazine, prednisone), BEP (bleomycin, etoposide, platinum agent (cisplatin (Platinol)), CAF (cyclophosphamide, Adriamycin, fluorouracil (5-FU)), CAV (cyclophosphamide, Adriamycin, vincristine), CHOP (cyclophosphamide, Adriamycin, vincristine, prednisone), Ch1VPP/EVA (chlorambucil, vincristine, procarbazine, prednisone, etoposide, vinblastine, Adriamycin), CVAD/HyperCVAD (cyclophosphamide, vincristine, Adriamycin, dexamethasone), DT-PACE (dexamethasone, thalidomide, cisplatin or platinol, Adriamycin, cyclophosphamide, etoposide), FAC (5-fluorouracil, Adriamycin, cyclophosphamide), m-BACOD (methotrexate, bleomycin, adriamycin, cyclophosphamide, Oncovin (vincristine), dexamethasone), MACOP-B (methotrexate, leucovorin (folinic acid), adriamycin, cyclophosphamide, Oncovin (vincristine), prednisone, bleomycin), ProMACE-MOPP (methotrexate, Adriamycin, cyclophosphamide, etoposide +MOPP), ProMACE-CytaBOM (prednisone, Adriamycin, cyclophosphamide, etoposide, cytarabine, bleomycin, vincristine, methotrexate, leucovorin), VAD (vincristine, Adriamycin, dexamethasone), Regimen I (vincristine, Adriamycin, etoposide, cyclophosphamide) and VAPEC-B (vincristine, Adriamycin, prednisone, etoposide, cyclophosphamide, bleomycin).

In one embodiment, the present invention contemplates a method of treating cancer, comprising: providing: i) a subject with cancer (e.g. breast cancer), ii) a chemotherapeutic agent, and iii) an inhibitor of a gene encoding a cytoplasmic tyrosine kinase, b) treating said subject with said chemotherapeutic agent, c) identifying resistance of at least some of said breast cancer cells to said chemotherapeutic agent; and d) treating said subject with said inhibitor. In one embodiment, the cytoplasmic tyrosine kinase is Bruton's Tyrosine Kinase. In one embodiment, the cytoplasmic tyrosine kinase is a variant of Bruton's Tyrosine Kinase comprising an amino-terminal extension. In another embodiment, the extension comprises an additional 34 amino acids. In another embodiment, the inhibitor comprises interfering double stranded RNA. In yet another embodiment, the chemotherapeutic agent comprises Doxorubicin or analogues thereof. In yet another embodiment, treating with the chemotherapeutic agent results in reduced proliferation of at least some breast cancer cells within the subject. In one embodiment, the interfering double stranded RNA comprises a sense strand having the nucleotide sequence of SEQ ID NO: 66. In one embodiment, the interfering double stranded RNA comprises an antisense strand having the nucleotide sequence of SEQ ID NO: 67. In one embodiment, the interfering double stranded RNA comprises a sense strand having the nucleotide sequence of SEQ ID NO: 68. In one embodiment, the interfering double stranded RNA comprises an antisense strand having the nucleotide sequence of SEQ ID NO: 69. In one embodiment, the inhibitor comprises a mixture of interfering double stranded RNAs comprising a sense strand having the nucleotide sequence of SEQ ID NOs: 66 and 68 and an antisense strand having the nucleotide sequence of SEQ ID NOs: 67 and 69. In another embodiment, the inhibitor results in reduced proliferation of at least some breast cancer cells within said subject identified as resistant to said chemotherapeutic agent. In yet another embodiment, the chemotherapeutic agent includes, but is not limited to, AC (Adriamycin, cyclophosphamide), TAC (taxotere, AC), ABVD (Adriamycin, bleomycin, vinblastine, dacarbazine), BEACOPP (bleomycin, etoposide, Adriamycin, cyclophosphamide, vincristine, procarbazine, prednisone), BEP (bleomycin, etoposide, platinum agent (cisplatin (Platinol)), CAF (cyclophosphamide, Adriamycin, fluorouracil (5-FU)), CAV (cyclophosphamide, Adriamycin, vincristine), CHOP (cyclophosphamide, Adriamycin, vincristine, prednisone), Ch1VPP/EVA (chlorambucil, vincristine, procarbazine, prednisone, etoposide, vinblastine, Adriamycin), CVAD/H erCVAD (cyclophosphamide, vincristine, Adriamycin, dexamethasone), DT-PACE (dexamethasone, thalidomide, cisplatin or platinol, Adriamycin, cyclophosphamide, etoposide), FAC (5-fluorouracil, Adriamycin, cyclophosphamide), m-BACOD (methotrexate, bleomycin, adriamycin, cyclophosphamide, Oncovin (vincristine), dexamethasone), MACOP-B (methotrexate, leucovorin (folinic acid), adriamycin, cyclophosphamide, Oncovin (vincristine), prednisone, bleomycin), ProMACE-MOPP (methotrexate, Adriamycin, cyclophosphamide, etoposide +MOPP), ProMACE-CytaBOM (prednisone, Adriamycin, cyclophosphamide, etoposide, cytarabine, bleomycin, vincristine, methotrexate, leucovorin), VAD (vincristine, Adriamycin, dexamethasone), Regimen I (vincristine, Adriamycin, etoposide, cyclophosphamide) and VAPEC-B (vincristine, Adriamycin, prednisone, etoposide, cyclophosphamide, bleomycin).

In one embodiment, the present invention contemplates a method of treating cancer, comprising: a) providing: i) a subject with cancer (e.g. breast cancer), ii) a chemotherapeutic agent, and iii) an inhibitor of a gene encoding a cytoplasmic tyrosine kinase, b) treating said subject with said inhibitor; and c) after step b), treating said subject with said chemotherapeutic. In one embodiment, the cytoplasmic tyrosine kinase is Bruton's Tyrosine Kinase. In another embodiment, the cytoplasmic tyrosine kinase is a variant of Bruton's Tyrosine Kinase comprising an amino-terminal extension. In yet another embodiment, the extension comprises an additional 34 amino acids. In still further embodiments, the inhibitor comprises interfering double stranded RNA. In one embodiment, the chemotherapeutic agent comprises Doxorubicin or analogues thereof. In another embodiment, treating with the chemotherapeutic agent results in reduced proliferation of the breast cancer cells within the subject. In one embodiment, the interfering double stranded RNA comprises a sense strand having the nucleotide sequence of SEQ ID NO: 66. In one embodiment, the interfering double stranded RNA comprises an antisense strand having the nucleotide sequence of SEQ ID NO: 67. In one embodiment, the interfering double stranded RNA comprises a sense strand having the nucleotide sequence of SEQ ID NO: 68. In one embodiment, the interfering double stranded RNA comprises an antisense strand having the nucleotide sequence of SEQ ID NO: 69. In another embodiment, the inhibitor comprises a mixture of interfering double stranded RNAs comprising a sense strand having the nucleotide sequence of SEQ ID NOs: 66 and 68 and an antisense strand having the nucleotide sequence of SEQ ID NOs: 67 and 69. In yet another embodiment, the inhibitor results in reduced proliferation of the breast cancer cells within said subject. In yet another embodiment, the chemotherapeutic agent includes, but is not limited to, AC (Adriamycin, cyclophosphamide), TAC (taxotere, AC), ABVD (Adriamycin, bleomycin, vinblastine, dacarbazine), BEACOPP (bleomycin, etoposide, Adriamycin, cyclophosphamide, vincristine, procarbazine, prednisone), BEP (bleomycin, etoposide, platinum agent (cisplatin (Platinol)), CAF (cyclophosphamide, Adriamycin, fluorouracil (5-FU)), CAV (cyclophosphamide, Adriamycin, vincristine), CHOP (cyclophosphamide, Adriamycin, vincristine, prednisone), Ch'VPP/EVA (chlorambucil, vincristine, procarbazine, prednisone, etoposide, vinblastine, Adriamycin), CVAD/HyperCVAD (cyclophosphamide, vincristine, Adriamycin, dexamethasone), DT-PACE (dexamethasone, thalidomide, cisplatin or platinol, Adriamycin, cyclophosphamide, etoposide), FAC (5-fluorouracil, Adriamycin, cyclophosphamide), m-BACOD (methotrexate, bleomycin, adriamycin, cyclophosphamide, Oncovin (vincristine), dexamethasone), MACOP-B (methotrexate, leucovorin (folinic acid), adriamycin, cyclophosphamide, Oncovin (vincristine), prednisone, bleomycin), ProMACE-MOPP (methotrexate, Adriamycin, cyclophosphamide, etoposide +MOPP), ProMACE-CytaBOM (prednisone, Adriamycin, cyclophosphamide, etoposide, cytarabine, bleomycin, vincristine, methotrexate, leucovorin), VAD (vincristine, Adriamycin, dexamethasone), Regimen I (vincristine, Adriamycin, etoposide, cyclophosphamide) and VAPEC-B (vincristine, Adriamycin, prednisone, etoposide, cyclophosphamide, bleomycin).

In one embodiment, the present invention contemplates a method of treating cancer, comprising: a) providing: i) a subject with breast cancer cells, at least some of said breast cancer cells exhibiting resistance to a chemotherapeutic agent, and ii) an inhibitor of a gene encoding a cytoplasmic tyrosine kinase, and b) treating said subject with said inhibitor. In one embodiment, the cytoplasmic tyrosine kinase is Bruton's Tyrosine Kinase. In one embodiment, the cytoplasmic tyrosine kinase is a variant of Bruton's Tyrosine Kinase comprising an amino-terminal extension. In one embodiment, the extension comprises an additional 34 amino acids. In one embodiment the inhibitor comprises interfering double stranded RNA. In another embodiment, treating with the inhibitor results in reduced proliferation of at least some of the breast cancer cells within the subject. In another embodiment, the interfering double stranded RNA comprises a sense strand having the nucleotide sequence of SEQ ID NO: 66. In yet another embodiment, the interfering double stranded RNA comprises an antisense strand having the nucleotide SEQ ID NO: 67. In yet another embodiment, the interfering double stranded RNA comprises a sense strand having the nucleotide sequence of SEQ ID NO: 68. In another embodiment, the interfering double stranded RNA comprises an antisense strand having the nucleotide sequence of SEQ ID NO: 69. In one embodiment, the inhibitor comprises a mixture of interfering double stranded RNAs comprising a sense strand having the nucleotide sequence of SEQ ID NOs: 66 and 68 and an antisense strand having the nucleotide sequence of SEQ ID NOs: 67 and 69. In one embodiment, the inhibitor results in reduced proliferation of at least some breast cancer cells within the subject identified as resistant to the chemotherapeutic agent. In another embodiment, the chemotherapeutic agent is selected from the group consisting of AC (Adriamycin, cyclophosphamide), TAC (taxotere, AC), ABVD (Adriamycin, bleomycin, vinblastine, dacarbazine), BEACOPP (bleomycin, etoposide, Adriamycin, cyclophosphamide, vincristine, procarbazine, prednisone), BEP (bleomycin, etoposide, platinum agent (cisplatin (Platinol)), CAF (cyclophosphamide, Adriamycin, fluorouracil (5-FU)), CAV (cyclophosphamide, Adriamycin, vincristine), CHOP (cyclophosphamide, Adriamycin, vincristine, prednisone), Ch1VPP/EVA (chlorambucil, vincristine, procarbazine, prednisone, etoposide, vinblastine, Adriamycin), CVAD/HyperCVAD (cyclophosphamide, vincristine, Adriamycin, dexamethasone), DT-PACE (dexamethasone, thalidomide, cisplatin or platinol, Adriamycin, cyclophosphamide, etoposide), FAC (5-fluorouracil, Adriamycin, cyclophosphamide), m-BACOD (methotrexate, bleomycin, adriamycin, cyclophosphamide, Oncovin (vincristine), dexamethasone), MACOP-B (methotrexate, leucovorin (folinic acid), adriamycin, cyclophosphamide, Oncovin (vincristine), prednisone, bleomycin), ProMACE-MOPP (methotrexate, Adriamycin, cyclophosphamide, etoposide +MOPP), ProMACE-CytaBOM (prednisone, Adriamycin, cyclophosphamide, etoposide, cytarabine, bleomycin, vincristine, methotrexate, leucovorin), VAD (vincristine, Adriamycin, dexamethasone), Regimen I (vincristine, Adriamycin, etoposide, cyclophosphamide) and VAPEC-B (vincristine, Adriamycin, prednisone, etoposide, cyclophosphamide, bleomycin).

The present invention does not intend to limit the type of cancer being treated to breast cancer. Cancers that may be treated using the compositions and methods of the present invention include, for example, leukemia, carcinoma, lymphoma, astrocytoma, sarcoma, glioma, retinoblastoma, melanoma, Wilm's tumor, bladder cancer, colon cancer, hepatocellular cancer, pancreatic cancer, prostate cancer, lung cancer, liver cancer, stomach cancer, cervical cancer, testicular cancer, renal cell cancer, and brain cancer.

The present invention does not intend to limit the types of RNA used to silence gene expression via RNA interference (RNAi). In one embodiment, the present invention contemplates the use of shRNAs, siRNAs, microRNAs (miRNAs), and single- or double-stranded analogues thereof, for silencing gene expression.

The present invention does not intend to limit the compounds and/or molecules used to silence gene expression to dsRNA molecules, such as shRNAs and siRNAs. In one embodiment, the present invention contemplates that inhibitors of cancer cells (e.g. breast cancer) may include small molecule inhibitors of hematopoietic cancers including, but not limited to, ibrutinib (and analogues thereof).

In one embodiment, the instant invention provides a method of treating cancer, comprising: a) providing a subject with cancer (e.g. breast cancer cells) and inhibitors of a gene encoding a cytoplasmic tyrosine kinase, and b) treating said subject with said inhibitor. In one embodiment, the cytoplasmic tyrosine kinase is Bruton's Tyrosine Kinase. In one embodiment, the cytoplasmic tyrosine kinase is a variant of Bruton's Tyrosine Kinase comprising an amino-terminal extension. In one embodiment, the extension comprises an additional 34 amino acids. In one embodiment, the inhibitor is ibrutinib.

In one embodiment, the instant invention provides a method of treating cancer, comprising: a) providing a subject with cancer (e.g. breast cancer cells) and inhibitors of a gene encoding the encoding an epidermal growth factor, and b) treating said subject with said inhibitor. In one embodiment, the epidermal growth factor is HER2. In one embodiment, the inhibitor is ibrutinib. In one embodiment, ibrutinib inhibits HER2 at a 10-fold lower concentration that lapatinib.

In another embodiment, the compounds of the present invention can be combined with other signal transduction inhibitors. Examples of such agents include, by no way of limitation, antibody therapies such as Herceptin (trastuzumab), Erbitux (cetuximab), Yervoy (ipilimumab) and pertuzumab. Examples of such therapies also include, by no way of limitation, small-molecule kinase inhibitors such as Imatinib (Gleevec), Sunitinib (Sutent), Sorafenib (Nexavar), Erlotinib (Tarceva), Gefitinib (Iressa), Dasatinib (Sprycel), Nilotinib (Tasigna), Lapatinib (Tykerb), Crizotinib (Xalkori), Ruxolitinib (Jakafi), Vemurafenib (Zelboraf), Vandetanib (Caprelsa), Pazopanib (Votrient), afatinib, alisertib, amuvatinib, axitinib, bosutinib, brivanib, canertinib, cabozantinib, cediranib, crenolanib, dabrafenib, dacomitinib, danusertib, dovitinib, foretinib, ganetespib, ibrutinib, iniparib, lenvatinib, linifanib, linsitinib, masitinib, momelotinib, motesanib, neratinib, niraparib, oprozomib, olaparib, pictilisib, ponatinib, quizartinib, regorafenib, rigosertib, rucaparib, saracatinib, saridegib, tandutinib, tasocitinib, telatinib, tivantinib, tivozanib, tofacitinib, trametinib, vatalanib, veliparib, vismodegib, volasertib, BMS-540215, BMS777607, JNJ38877605, TKI258, GDC-0941 (Folkes, et al., J. Med. Chem. 2008, 51, 5522), BZE235, and others.

In one embodiment, the instant invention provides a method of treating cancer, comprising: a) providing a subject with cancer (e.g. breast cancer cells) and an inhibitor of a gene encoding the tyrosine kinase LYN and b) treating said subject with said inhibitor. In one embodiment the inhibitor is an shRNA. In another embodiment, the inhibitor is an siRNA.

In one embodiment, the present invention contemplates a method of treating cancer, comprising: a) providing: i) a subject with breast cancer cells, at least some of said breast cancer cells exhibiting resistance to a chemotherapeutic agent, and ii) an inhibitor of a gene encoding a cytoplasmic tyrosine kinase, and b) treating said subject with said inhibitor. In one embodiment, the cytoplasmic tyrosine kinase is Bruton's Tyrosine Kinase. In one embodiment, the cytoplasmic tyrosine kinase is a variant of Bruton's Tyrosine Kinase comprising an amino-terminal extension. In one embodiment, the extension comprises an additional 34 amino acids. In one embodiment the inhibitor comprises interfering double stranded RNA. In another embodiment, treating with the inhibitor results in reduced proliferation of at least some of the breast cancer cells within the subject. In one embodiment, the inhibitor is LFM-A13. In one embodiment, the inhibitor results in reduced proliferation of at least some breast cancer cells within the subject identified as resistant to the chemotherapeutic agent. In another embodiment, the chemotherapeutic agent is selected from the group consisting of AC (Adriamycin, cyclophosphamide), TAC (taxotere, AC), ABVD (Adriamycin, bleomycin, vinblastine, dacarbazine), BEACOPP (bleomycin, etoposide, Adriamycin, cyclophosphamide, vincristine, procarbazine, prednisone), BEP (bleomycin, etoposide, platinum agent (cisplatin (Platinol)), CAF (cyclophosphamide, Adriamycin, fluorouracil (5-FU)), CAV (cyclophosphamide, Adriamycin, vincristine), CHOP (cyclophosphamide, Adriamycin, vincristine, prednisone), ChIVPP/EVA (chlorambucil, vincristine, procarbazine, prednisone, etoposide, vinblastine, Adriamycin), CVAD/Hyper-CVAD (cyclophosphamide, vincristine, Adriamycin, dexamethasone), DT-PACE (dexamethasone, thalidomide, cisplatin or platinol, Adriamycin, cyclophosphamide, etoposide), FAC (5-fluorouracil, Adriamycin, cyclophosphamide), m-BACOD (methotrexate, bleomycin, adriamycin, cyclophosphamide, Oncovin (vincristine), dexamethasone), MACOP-B (methotrexate, leucovorin (folinic acid), adriamycin, cyclophosphamide, Oncovin (vincristine), prednisone, bleomycin), ProMACE-MOPP (methotrexate, Adriamycin, cyclophosphamide, etoposide+MOPP), ProMACE-CytaB OM (prednisone, Adriamycin, cyclophosphamide, etoposide, cytarabine, bleomycin, vincristine, methotrexate, leucovorin), VAD (vincristine, Adriamycin, dexamethasone), Regimen I (vincristine, Adriamycin, etoposide, cyclophosphamide) and VAPEC-B (vincristine, Adriamycin, prednisone, etoposide, cyclophosphamide, bleomycin).

In one embodiment, the instant invention provides a method of treating cancer, comprising: a) providing a subject with cancer (e.g. breast cancer cells) and inhibitors of a gene encoding the encoding a cytoplasmic tyrosine kinase, and b) treating said subject with said inhibitor. In one embodiment, the cytoplasmic tyrosine kinase is Bruton's Tyrosine Kinase. In one embodiment, the cytoplasmic tyrosine kinase is a variant of Bruton's Tyrosine Kinase comprising an amino-terminal extension. In one embodiment, the extension comprises an additional 34 amino acids. In one embodiment the inhibitors are shRNA. In one embodiment, the inhibtors are siRNA. In one embodiment, the present invention contemplates a combination of shRNA and siRNA. In one embodiment, the shRNA targets an internal exon of BTK. In another embodiment, the siRNA targets BTK-C.

In one embodiment, the instant invention provides a method of treating cancer, comprising: a) providing a subject with a cancer (e.g. breast cancer cells) with an acquired resistance to at least one chemotherapeutic agent, and inhibitors of a gene encoding the encoding a cytoplasmic tyrosine kinase, and b) treating said subject with said inhibitor. In one embodiment, the cytoplasmic tyrosine kinase is Bruton's Tyrosine Kinase. In one embodiment, the cytoplasmic tyrosine kinase is a variant of Bruton's Tyrosine Kinase comprising an amino-terminal extension. In one embodiment, the extension comprises an additional 34 amino acids. In one embodiment, the acquired resistance of said cancer cells is to imatinib.

FIGURE LEGENDS

FIG. 1. An RNAi screen targeting tyrosine kinase genes in an ERBB2 (HER2/neu) positive breast cancer. BT474 breast cancer cells were transfected with 234 shRNA constructs targeting 83 protein tyrosine kinase genes. Three transfection mixes were produced for each shRNA and each was transfected into triplicate wells of BT474 cells for 96 hours. AlamarBlue was used to monitor cell proliferation and viability. The averages of the nine parallel cultures were calculated for each shRNA, normalized to transfection efficiency, presented as % of the control shRNA and sorted on the basis of effect. z-scores were calculated using the following formula: (normalized sample value−normalized data set mean)/data set standard deviation. shRNAs that produced z-scores less than −1.1 are presented in a list (Table 2).

FIG. 2. Btk knockdown in BT474 cells leads to increased apoptosis. (a) Brightfield image after 96 hr of siRNA knockdown of Btk in BT474 cells. (b-c) siRNA knockdown of Btk in BT474 cells (48 hr) results in increased cleaved caspase-3 (CC3) compared to a scrambled siRNA. (b) Apoptotic cells were calculated as a percentage of the total cellular population.

FIG. 3. An alternative form of the Btk transcript is present in BT474 breast cancer cells. (a) Nucleotide sequence 1-395 by from the published Btk sequence (accession # U13399) was aligned to the nucleotide sequence obtained from BT474 cells using 5'RACE. Identical sequence is highlighted in grey. The BT474 sequence obtained using 5'RACE translates into an additional 47 amino acid open reading frame (ORF) and contains two additional methionine codons, highlighted in green, that are in frame with the methionine start codon of the published Btk gene (highlighted in green and with an arrow). (b) Schematic representation showing the location of the Btk gene on the X-chromosome (b & c) and schematic representations comparing the location of the Btk-A and Btk-C exon 1.

FIG. 4. BTK-C yields an 80 kD BTK specific product. (a) A schematic representation showing the conserved domains of the BTK-A protein is compared to a schematic of the predicted BTKC protein. (b) Total lysate from BT474 cells and a malignant B-cell line positive for Btk-A (Namalwa) were subjected to immunoblotting with the BTK antibody. (c) 293FT cells were co-transfected with a BTK-A or BTK-C flag tag over-expression vector as well as a Btk shRNA or a control shRNA targeting the firefly luciferase gene. (d) siRNAs targeting, stably, over-expressed BTK-C in BT474 cells leads to efficient knockdown. BT474 cells were transfected with siRNAs and total lysate was used for immunoblotting with the BTK antibody.

FIG. 5. BTK-C is activated in BT474 cells. (a) In BT474 cells both forms of the over-expressed Btk-C proteins are phosphorylated on tyrosine residue 223, which becomes auto-phosphorylated after activation. Total lysate was prepared from BT474 cells containing the stably integrated Btk-A or Btk-C flag tag MarxIV vectors. Controls cells contain a stably integrated MarxIV flag tag vector encoding the beta-galactosidase gene (-gal) which retains its stop codon. Tyrosine phosphorylated BTK was assessed by immunoprecipitation (IP) using anti-Flag and Western blot (WB) analysis using anti-BTK Phospho (pY223) and anti-BTK. (a) The specific BTK inhibitor LFM-A13 reduces phosphorylation of BTK. BT474 cells containing the stably integrated Btk-A or Btk-C flag tag MarxIV vectors were incubated with 100 [μM LFM-A13 for 45 mins. Tyrosine-phosphorylated BTK was assessed by immunoprecipitation (IP) using anti-Flag and Western blot (WB) analysis using anti-BTK Phospho (pY223) and anti-BTK. (b & c) Inhibition of BTK autophosphorylation using LFM-A13 results in increased apoptosis. BT474 cells incubated with either 25 uM or 35 uM LFM-A13 results in increased cleaved caspase-3 (CC3) compared to control cells treated with DMSO. (c) Apoptotic cells were calculated as a percentage of the total cellular population.

FIG. 6. BTK protein is present in BT474 cellular cytoplasm. (a) Confocal immunofluorescence images of BTK in BT474 cells. Left column: Alexa 568 secondary ab (no primary ab); middle column. BTK ab; right column: Flag Tag ab. (b) BT474 cells containing the stably integrated (left panels) control vector, (middle panels) BTK-A-flag vector, (right panels) BT-C-flag vector. Left panels: nuclei visualized with Hoechst; right panels: primary antibody (Btk or Flag) bound to secondary HRP conjugated antibody tagged with Alexa 568 tag.

FIG. 7. Btk-C is more abundant in breast cancer cells than in non-tumorigenic breast cells or a malignant B-cell line. (a) qPCR primers were designed to specifically target the Btk-C message and cDNA from the breast cancer cell lines BT474, MCF7, and MDA-MB-361, the non-tumorigenic breast cell lines MCF10a and HMEC, as well as, a malignant B-cell line was amplified using SYBR Green. The breast cancer cell lines BT474 and MCF7 had at least 4-fold more transcript compared to the non-tumorigenic breast cell lines MCF10a and HMEC and the malignant B-cell line Namalwa. Fold change was calculated using the delta, delta Ct method.

Figure 8:
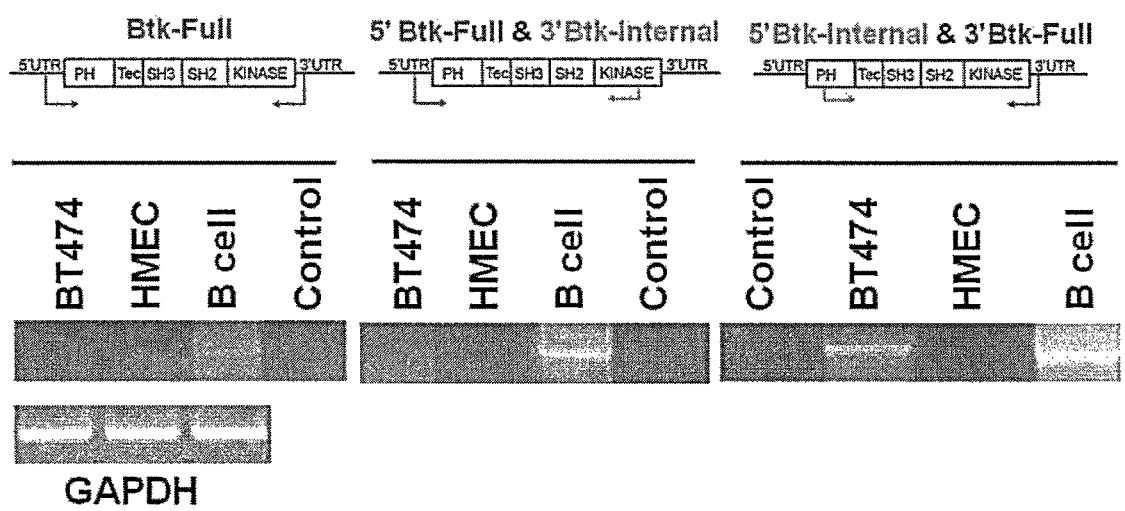

FIG. 8. Reverse Transcriptase Polymerase Chain Reaction (RT-PCR). tRNA was isolated from the BT474 breast cancer cell line, a normal breast epithelial cell line (HMEC) and a Btk positive control cell line (Namalwa B-cells) and cDNA was amplified from the breast cancer cells line BT474, a normal breast epithelial cell line (HMEC) and a positive control cell line for BTK-A expression (B-cells) using three different primer pair combinations. Two distinct primer pairs were generated to target the Btk transcript at different regions of the mRNA (5'UTR and Btk internal) and cDNA from each cell type was used as substrate in a polymerase chain reaction (PCR). (a) PCR products were amplified from cDNAs isolated from B-cells for all primer pair combinations used. A product was amplified from BT474 cDNA using the Btk internal forward primer but not when the 5'UTR forward primer was used. Differences in product size between BT474 and B cells in the rightmost panel are likely an artifact of electrophoresis or may represent the presence of internal splice variants in the Namalwa transcriptome. Data are representative of three replicated experiments.

Figure 9:
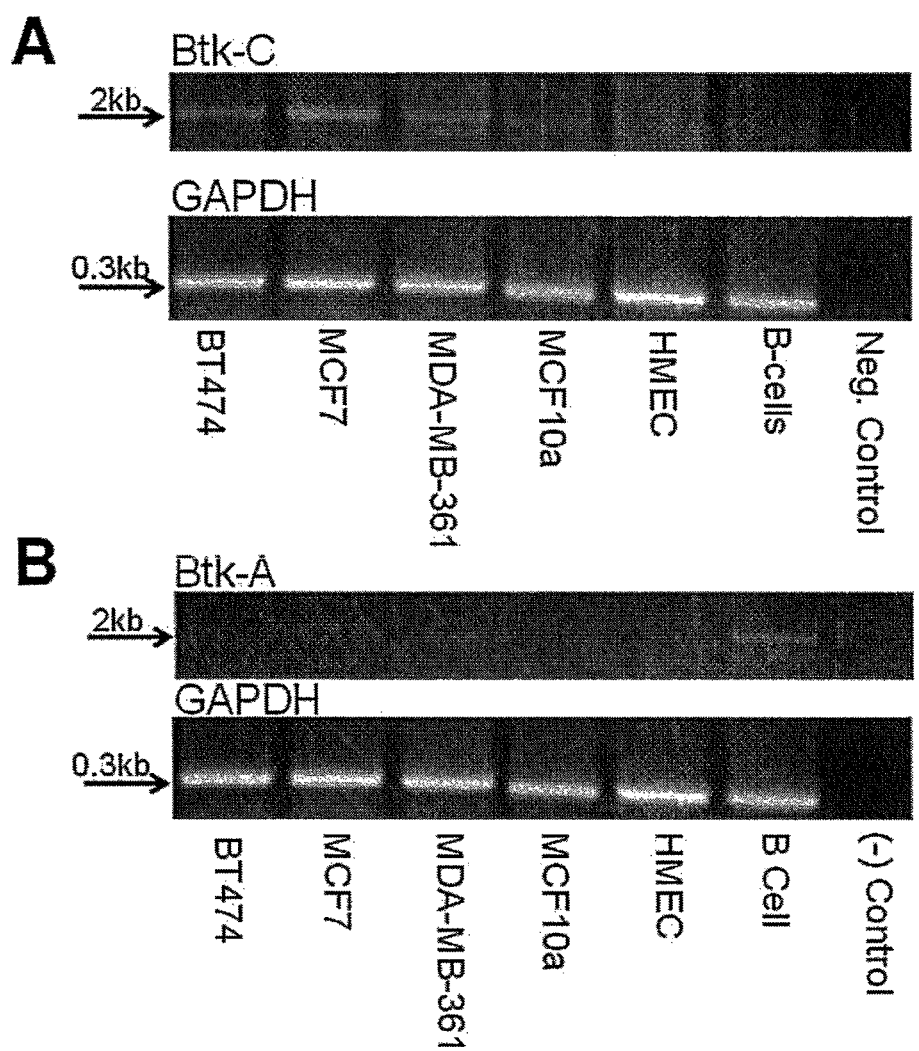

FIG. 9. BTK-C but not BTK-A is expressed in breast cell lines. Reverse Transcriptase Polymerase Chain Reaction (RT-PCR). tRNA was isolated from several breast cancer cell lines (BT474, MCF7, MDA-MB-361), and two normal cell lines, HMEC and MCF10a and cDNA was amplified from each. Primer pairs were designed to specifically target the Btk-A or BTK-C mRNA sequence and cDNA from each cell type was used as substrate in a polymerase chain reaction (PCR). (a) A PCR product was amplified from cDNA isolated from the B-cell line using the Btk-A specific primers but no product was amplified for any of the breast cell lines tested, whereas the BTK-C specific product was expressed preferentially in the breast cancer cell lines. Data is representative of three replicated experiments.

FIG. 10. (a) siRNA knockdown of BTK in BT474 cells (48 hr) results in increased cleaved caspase-3 (Caspase-3) staining indicative of apoptosis. (b) Degree of apoptosis due to BTK knockdown in BT474 and MCF-7 cells was calculated as a percentage of the total cellular population. The data were expressed as the mean of triplicate of the samples transfected with the BTK siRNA relative to scrambled siRNA control samples. Error bars represent standard deviation from the average of 3 replicates. Statistical significance between samples was calculated using the student's t test, where (*) indicates a P value of <0.0001. FIG. 11. An alternative form of the BTK transcript is present in BT474 breast cancer cells. (a) Nucleotide sequence 1-395 bp from the published BTK sequence (accession # U13399) was aligned to the nucleotide sequence obtained from BT474 cells using 5'RACE. Identical sequence is highlighted in grey. The BT474 sequence obtained using 5'RACE encodes an additional 34 amino acid open reading frame (ORF) and contains two additional methionine codons, highlighted in green, that are in frame with the methionine start codon from the published BTK gene (highlighted in green and with an arrow). (b) Schematic representation showing alternate splicing of alternative first exons from both isoforms inferred from sequence analysis. Sequences are identical from exons 2 through 19. (c) Map of BTK on the X-chromosome. BTKC exon 1 transcription initiates divergently 255 by from the start site of the ribosomal protein L36a gene.

Figure 12:
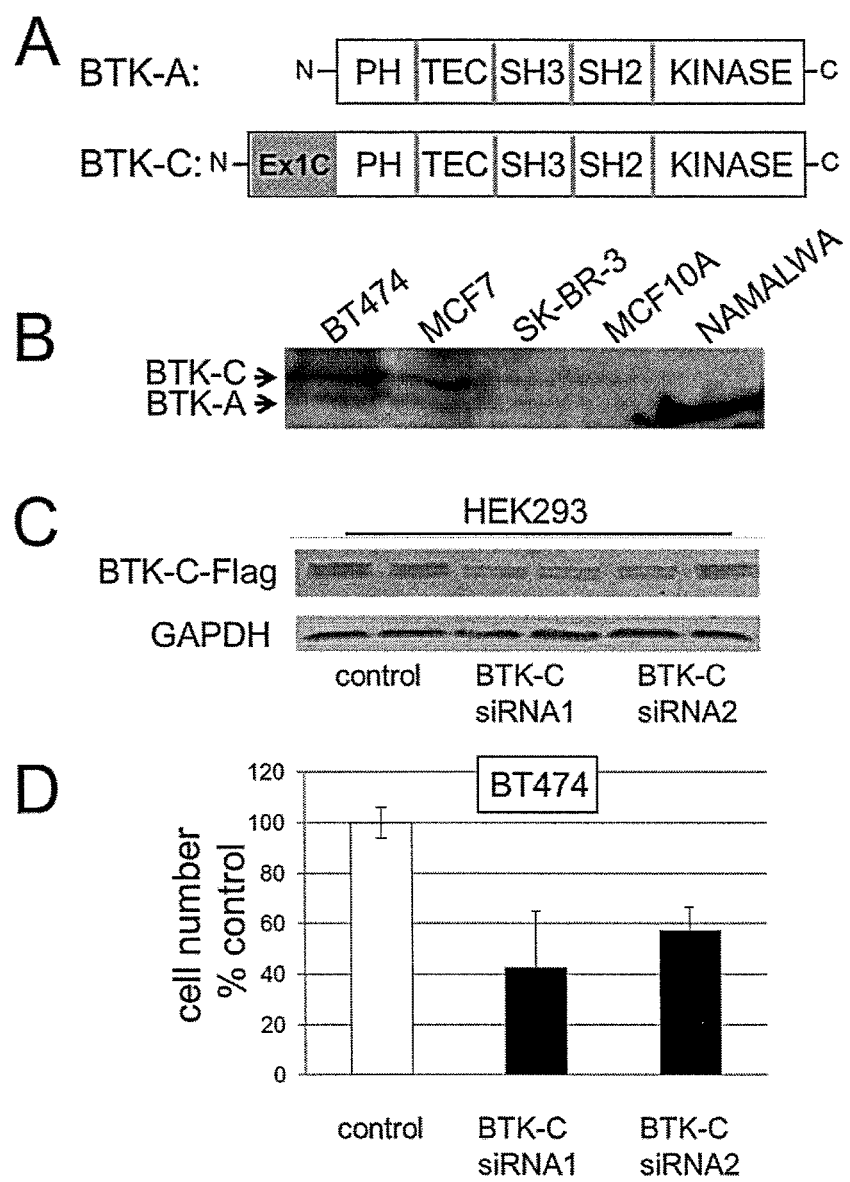

FIG. 12. The BTK-C gene produces an 80 kD product. (a) A schematic representation showing the domains of the BTK-A and predicted BTK-C protein. (b) Total lysate from breast lines and Namalwa B-cells subjected to immunoblotting and probed with an anti-BTK antibody (BD Transduction Laboratory, 611116). (c) HEK293 cells co-transfected with a BTK-C flag vector and either BTK-C siRNAs or Non-Target siRNA. Total lysate was prepared 96 hrs post transfection and was used for immunoblotting with anti-Flag antibody. (d) BT474 cells were transfected with two BTK-C specific siRNAs, non-target siRNA as a control and co-transfected with GFP to mark transfected cells. Transfected cells were counted at 24 h and 96 h and the 96 hr to 24 hr ratio was calculated and expressed as % of the control.

Figure 13:
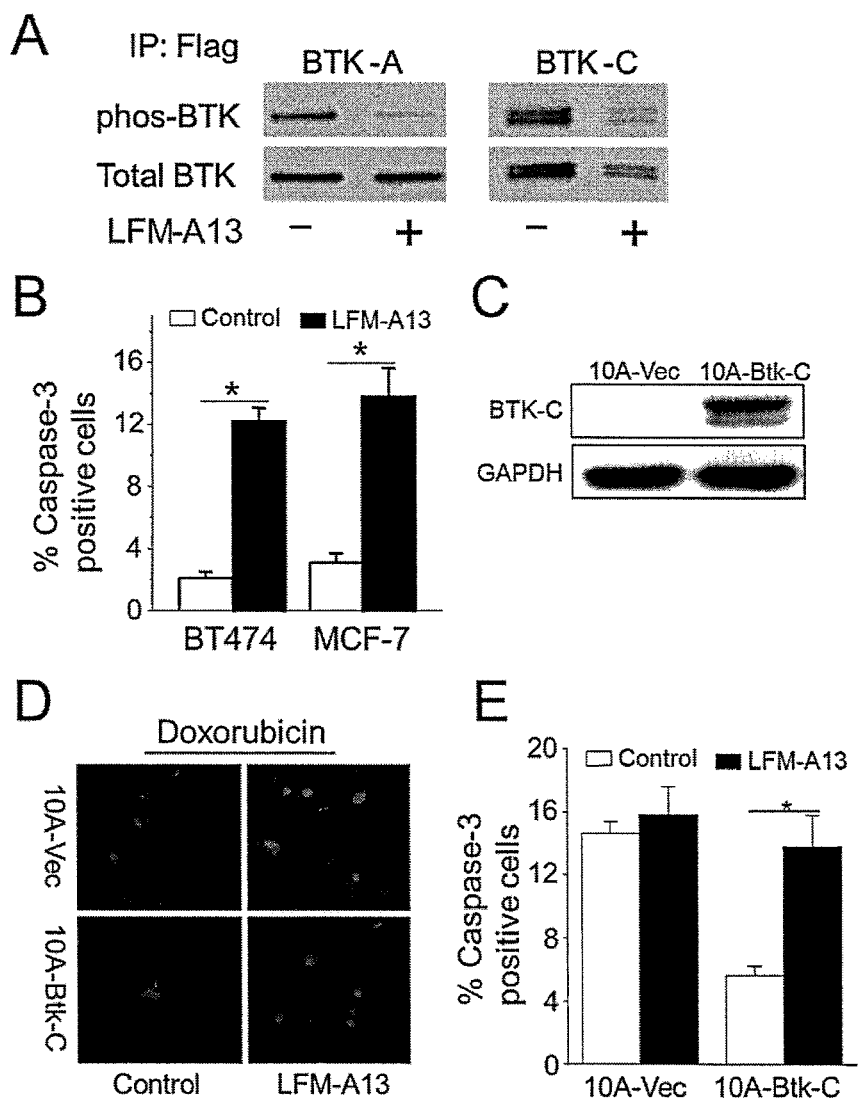

FIG. 13. BTK-C is activated in BT474 cells. In BT474 cells both forms of the over-expressed BTK-C proteins are phosphorylated on tyrosine residue 223, which becomes autophosphorylated after activation. (a) BT474 cells containing the stably integrated BTK-A-flag, the BTK-C-flag or control flag vector were treated with 100 μM LFM-A13 for 45 mins Tyrosine-phosphorylated BTK was assessed by immunoprecipitation (IP) using anti-Flag (Stratagene) and immunoblot analysis using anti-BTK Phospho (pY223) and anti-BTK antibody (BTK-E9 Santa Cruz). (b) Inhibition of BTK autophosphorylation using LFM-A13 results in increased apoptosis. BT474 cells incubated with 35 μM LFM-A13 for 48 h results in increased cleaved caspase-3 (Caspase-3) compared to control cells treated with DMSO. Apoptotic cells were calculated as a percentage of the total cellular population as in FIG. 10B. (c) BTK-C inhibits apoptosis induced by Doxorubicin in MCF-10A cells. BTK-C expression in vector control (10A-Vec) and MCF-10A-BTK-C (10A-BtkC) cells using anti-Flag antibody. GAPDH is used as a loading control. (d) BTK-C expression reduces Doxorubicin-induced apoptosis as monitored by Cleaved caspase-3 signal. 10A-Vec or 10A-BTK-C cells were either treated with DMSO (Con) or with 35 uM LFM-A13 for 24 hours, after that the cells were washed with PBS for 3 times and added fresh medium with Doxorubicin (1 uM) for 24 hours. Immunofluorescence was performed for cleaved caspased-3 signal; cell nuclei were stained with Hoechst 33342. (e) Apoptotic cells were calculated as a percentage of the total cellular population, as indicated B. Error bars indicate the standard deviation from three individual experiments, *P<0.01.

Figure 14:
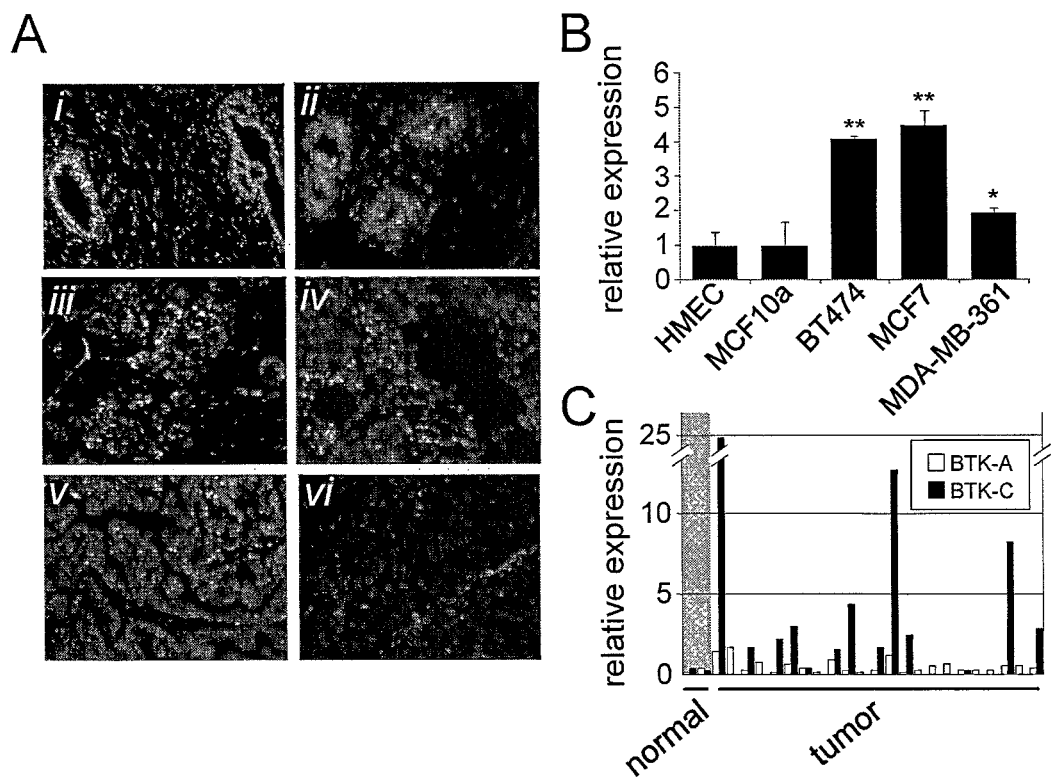

FIG. 14. BTK is more abundant in breast cancer cells compared to non-tumorigenic breast cells. (a) BTK protein levels were examined in normal, matched breast tissues and breast carcinoma tissue in tissue microarrays using immunofluorescence microscopy. DAPI staining of nuclei is shown in cyan false color; anti-BTK (ProSci) staining is red. Tissue samples and BTK classifications were (i) Normal-low level; (ii) benign hyperplasia-low level; (iii) Cancer-low-moderate/heterogenous; (iv) Cancer-heterogenous with strong positives; (v) Cancer-homogenous moderate with nuclear; (vi) Cancer-negative. (b) BTK-C message is more abundant than the BTK-A isoform in cancer cell lines. qPCR primers designed to specifically target the BTK-C message and cDNA from the breast cancer cell lines BT474, MCF7, MDA-MB-361 and two non-tumorigenic breast cell lines, HMEC and MCF 10a were amplified using SYBR Green. Fold change was calculated using the delta, delta Ct method. Error bars represent standard deviation from the average of 4 replicates. Statistical significance between samples was calculated using the student's t test, where (*) indicates a P value of <0.005 and (**) indicates a value of <0.0005. (c) BTK-C message is more abundant than the BTK-A isoform in breast tumors. cDNA prepared from RNA isolated from human breast tissue was subjected to qPCR using primers specific for BTK-A and BTK-C isoforms. The same set of samples in another plate was used for detection of actin mRNA. The data represent relative mRNA levels of each BTK isoform normalized to actin.

Figure 15:
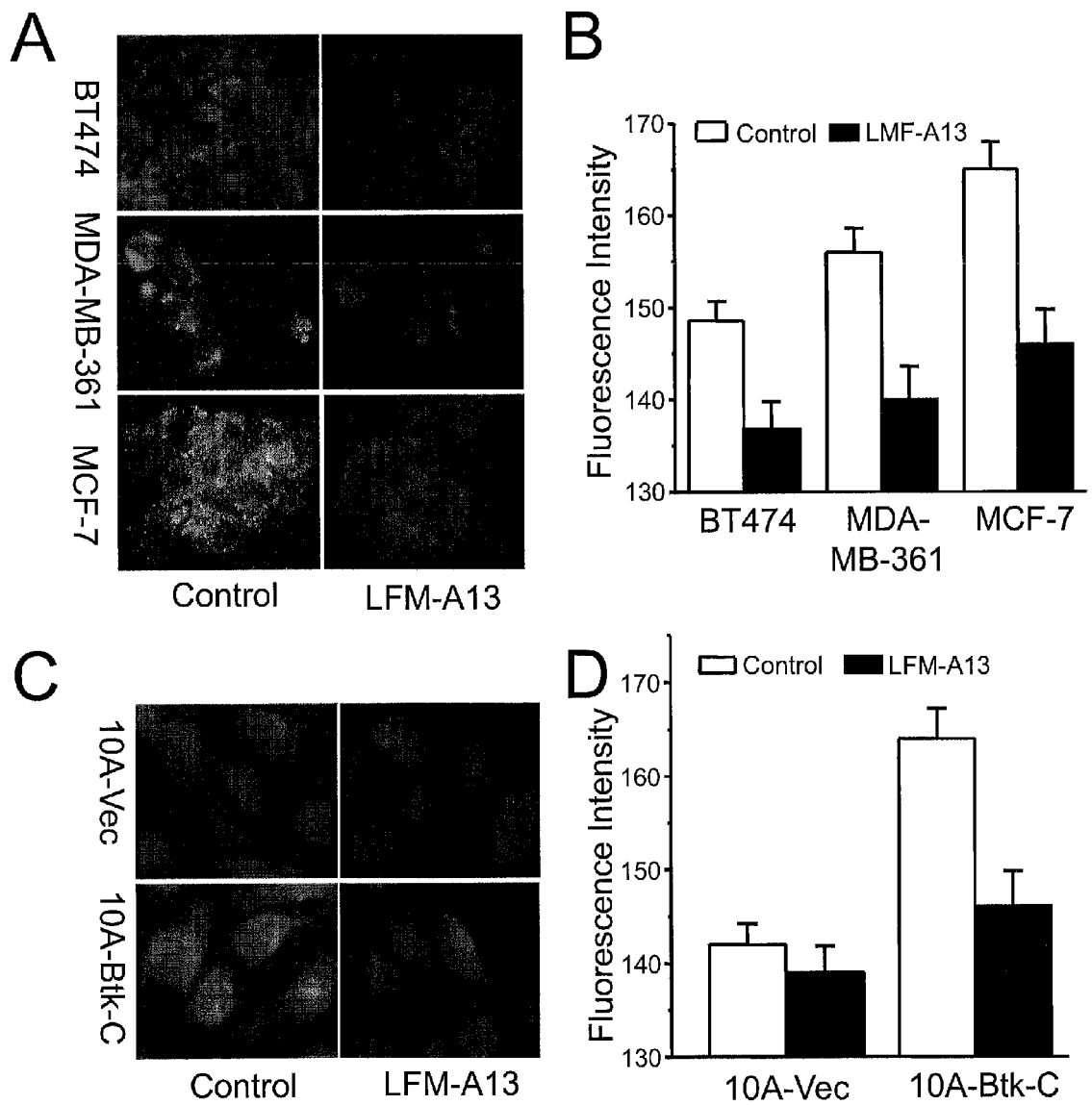

FIG. 15. BTK-C promotes glucose uptake. (c) LFM-A13 inhibits glucose uptake in 10A-BTK-C cells. 10A-Vec and 10A-BTK-C cells were either treated with DMSO (Control) or with 35 μM LFM-A13 for 24 hours, after that the cells were washed with PBS for 3 times and added 100 μm 2-NBDG for 15 min. Immunofluorescence pictures were taken in INCELL-1000; (d) Fluorescence intensity was quantified in right. Error bars indicate the standard deviation from three individual experiments, *P<0.01. (a) The effect of BTK-C on glucose uptake in breast cancer cell lines. MCF-7 and MDA-MB-361 cell lines were treated as in (c). (b) Fluorescence intensity shown at right panel, *p<0.01.

Figure 16:
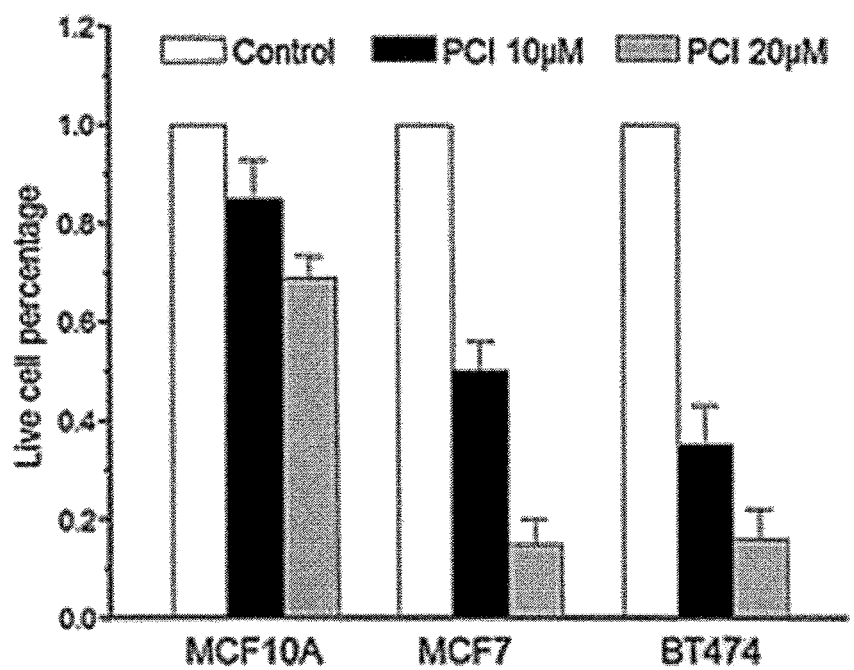

FIG. 16. BTK inhibition results in breast cancer cell death. Cell counts of MCF10A, MCF7 and BT474 cells treated with vehicle, 10 and 20 μmol/l. of the BTK kinase inhibitor PCI-32765 (ibrutinib) for 48 hours. Results are presented as percentage of control. Error bars indicate the standard deviation for three individual experiments. MCF10A serves as a normal (i.e. non-cancerous cell) control. MCF7 and BT474 are cancer cell lines.

FIG. 17. The BTK-C gene produces an 80 kD product. (a) 293FT cells co-transfected with a BTK-A or BTK-C flag over-expression vector and either BTK shRNA or control shRNA. Total lysates were prepared 48 hours post transfection and used for immunoblotting with anti-Flag antibody (Stratagene). (b) BT474 cells stably over-expressing BTK-C (MarxIV) transfected with siRNAs targeting BTK (48 hours) leads to efficient BTK knockdown compared to cells transfected with a control siRNA. Total lysates were used for immunoblotting with an anti-BTK antibody (ProSci).

Figure 18:
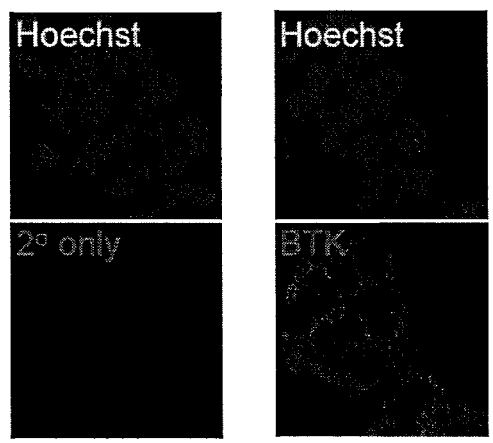

FIG. 18. BTK is predominantly found in the cytoplasm of BT474 breast cancer cells. Confocal immunofluorescence images of BTK in BT474 cells. Left column: Alexa568 conjugated to secondary antibody (no primary antibody); right column: anti-BTK antibody (ProSci); right column: anti-Flag antibody (Stratagene). Nuclei visualized with Hoechst; anti-BTK (ProSci) bound to secondary HRP conjugated antibody tagged with Alexa 568 tag.

Figure 19:
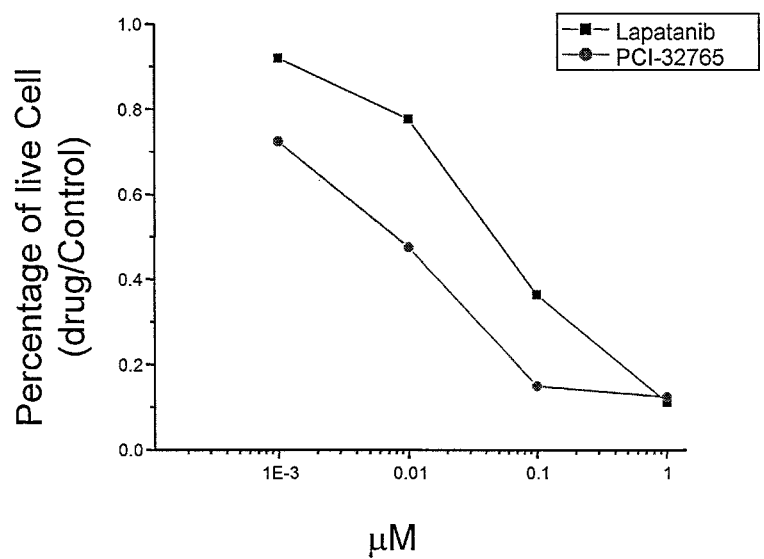

FIG. 19. Ibrutinib (PCI-32765) is effective at lower concentrations than Lapatinib in killing SK-Br-3 Her2/neu positive breast cancer cells. SKBR3 cells were treated with (or without) 50 ng/ml EGF and concomitantly exposed to different concentrations of Lapatinib. After 72 hours, cells were fixed with 4% formaldehyde, stained with Hoechst and cell number determined.

Figure 20:
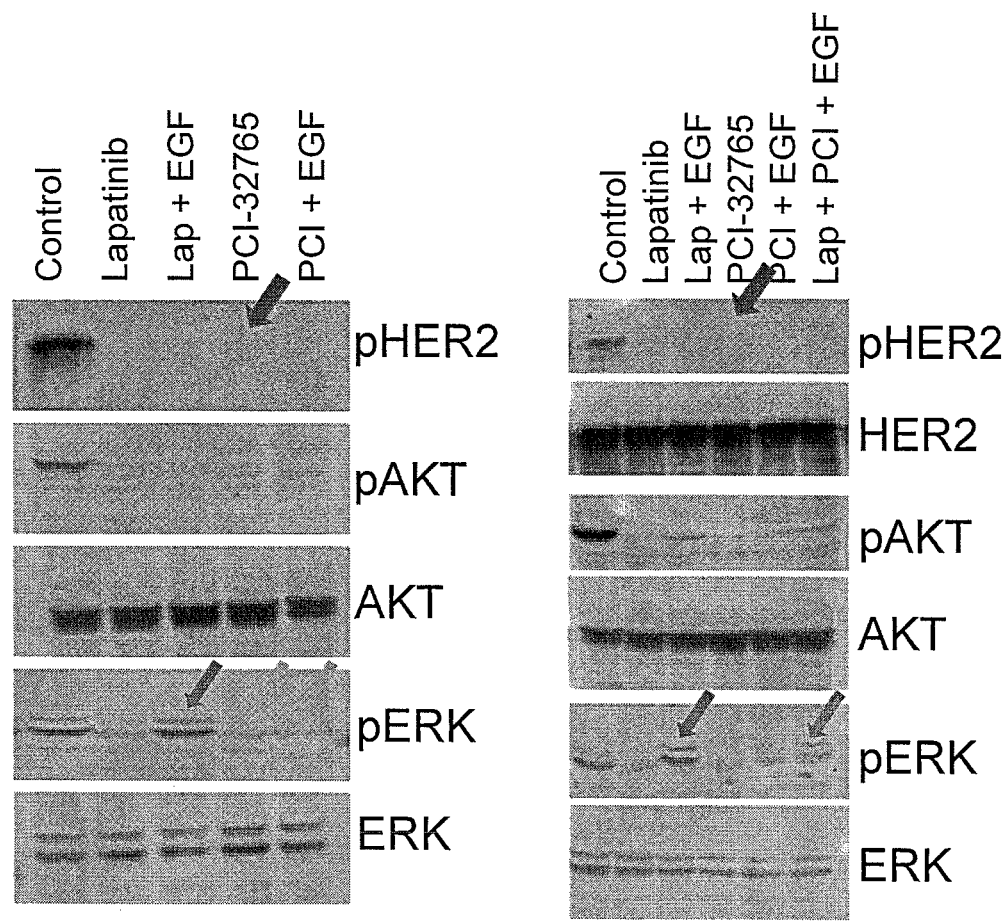

FIG. 20. PCI-32765 blocks ERRB2 (HER2/neu) activation in breast cancer cells (red arrows). EGF treatment has been shown to activate a pro-survival pathway whose reactivation correlates with EGF-stimulated ERK activation in tyrosine kinase inhibitor treated cells. EGF counteracts lapatinib's effect, causing ERK re-activation which correlates with potential decreased efficacy and drug resistance (green arrows). EGF treatment does not bypass the effects of PCI-32765 on inhibiting ERK activation (orange arrows) and prevents ERK reactivation in the presence of lapatinib (blue arrow). SKbr3 cells were treated with lapatinib (1 µM) with EGF (50 ng/ml), PCI-32765 (1 µM) or PCI-32765 (1 µM) with EGF (50 ng/ml). After 3 hours, cells were lysed. Immunoblots showing effect of kinase inhibition with or without EGF on HER2, AKT and ERK phosphorylation. Anti-pHER2 (1221), pAKT (437) and pERK (202/204).

FIG. 21. Sequence alignment. The ability of PCI-32765 to block ERRB2 (HER2/neu) activation in breast cancer cells may be due to similarities with the BTK active site. (a) EGFR family members EGFR, ERBB2 and ERRB4 share the PCI-32765-targeted cysteine residue found in BTK (red box). (b) Several other non-TEC family kinases do not share the PCI-32765-targeted cysteine residue (red box).

Figure 22:
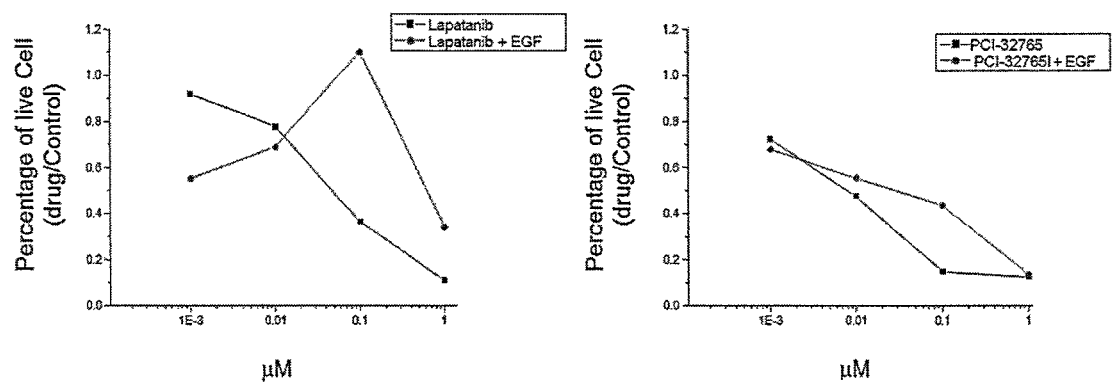

FIG. 22. EGF treatment counteracts lapatinib to a much larger degree than PCI-32765. SKBR3 cells were treated with (or without) 50 ng/ml EGF and concomitantly exposed to different concentrations of lapatinib or PCI-32765. After 72 hours, cell number was determined.

DEFINITIONS

To facilitate the understanding of this invention a number of terms (set off in quotation marks in this Definitions section) are defined below. Terms defined herein (unless otherwise specified) have meanings as commonly understood by a person of ordinary skill in the areas relevant to the present invention. As used in this specification and its appended claims, terms such as "a", "an" and "the" are not intended to refer to only a singular entity, but include the general class of which a specific example may be used for illustration, unless the context dictates otherwise. The terminology herein is used to describe specific embodiments of the invention, but their usage does not delimit the invention, except as outlined in the claims.

The phrase "chosen from A, B, and C" as used herein, means selecting one or more of A, B, C.

As used herein, absent an express indication to the contrary, the term "or" when used in the expression "A or B," where A and B refer to a composition, disease, product, etc., means one or the other, or both. As used herein, the term "comprising" when placed before the recitation of steps in a method means that the method encompasses one or more steps that are additional to those expressly recited, and that the additional one or more steps may be performed before, between, and/or after the recited steps. For example, a method comprising steps a, b, and c encompasses a method of steps a, b, x, and c, a method of steps a, b, c, and x, as well as a method of steps x, a, b, and c. Furthermore, the term "comprising" when placed before the recitation of steps in a method does not (although it may) require sequential performance of the listed steps, unless the context clearly dictates otherwise. For example, a method comprising steps a, b, and c encompasses, for example, a method of performing steps in the order of steps a, c, and b, the order of steps c, b, and a, and the order of steps c, a, and b, etc.

Unless otherwise indicated, all numbers expressing quantities of ingredients, properties such as molecular weights, reaction conditions, and so forth as used in the specification and claims are to be understood as being modified in all instances by the term "about." Accordingly, unless indicated to the contrary, the numerical parameters in the specification and claims are approximations that may vary depending upon the desired properties sought to be obtained by the present invention. At the very least, and without limiting the application of the doctrine of equivalents to the scope of the claims, each numerical parameter should at least be construed in light of the number of reported significant digits and by applying ordinary rounding techniques. Notwithstanding that the numerical ranges and parameters describing the broad scope of the invention are approximations, the numerical values in the specific examples are reported as precisely as possible. Any numerical value, however, inherently contains standard deviations that necessarily result from the errors found in the numerical value's testing measurements.

The term "not" when preceding, and made in reference to, any particularly named molecule (mRNA, etc.) or phenomenon (such as biological activity, biochemical activity, etc.) means that only the particularly named molecule or phenomenon is excluded.

The term "altering" and grammatical equivalents as used herein in reference to the level of any substance and/or phenomenon refers to an increase and/or decrease in the quantity of the substance and/or phenomenon, regardless of whether the quantity is determined objectively, and/or subjectively.

The terms "increase," "elevate," "raise," and grammatical equivalents when used in reference to the level of a substance and/or phenomenon in a first sample relative to a second sample, mean that the quantity of the substance and/or phenomenon in the first sample is higher than in the second sample by any amount that is statistically significant using any art-accepted statistical method of analysis. In one embodiment, the increase may be determined subjectively, for example when a patient refers to their subjective perception of disease symptoms, such as pain, clarity of vision, etc. In another embodiment, the quantity of the substance and/or phenomenon in the first sample is at least 10% greater than the quantity of the same substance and/or phenomenon in a second sample. In another embodiment, the quantity of the substance and/or phenomenon in the first sample is at least 25% greater than the quantity of the same substance and/or phenomenon in a second sample. In yet another embodiment, the quantity of the substance and/or phenomenon in the first sample is at least 50% greater than the quantity of the same substance and/or phenomenon in a second sample. In a further embodiment, the quantity of the substance and/or phenomenon in the first sample is at least 75% greater than the quantity of the same substance and/or phenomenon in a second sample. In yet another embodiment, the quantity of the substance and/or phenomenon in the first sample is at least 90% greater than the quantity of the same substance and/or phenomenon in a second sample. Alternatively, a difference may be expressed as an "n-fold" difference.

The terms "reduce," "inhibit," "diminish," "suppress," "decrease," and grammatical equivalents when used in reference to the level of a substance and/or phenomenon in a first sample relative to a second sample, mean that the quantity of substance and/or phenomenon in the first sample is lower than in the second sample by any amount that is statistically significant using any art-accepted statistical method of analysis. In one embodiment, the reduction may be determined subjectively, for example when a patient refers to their subjective perception of disease symptoms, such as pain, clarity of vision, etc. In another embodiment, the quantity of substance and/or phenomenon in the first sample is at least 10% lower than the quantity of the same substance and/or phenomenon in a second sample. In another embodiment, the quantity of the substance and/or phenomenon in the first sample is at least 25% lower than the quantity of the same substance and/or phenomenon in a second sample. In yet another embodiment, the quantity of the substance and/or phenomenon in the first sample is at least 50% lower than the quantity of the same substance and/or phenomenon in a second sample. In a further embodiment, the quantity of the substance and/or phenomenon in the first sample is at least 75% lower than the quantity of the same substance and/or phenomenon in a second sample. In yet another embodiment, the quantity of the substance and/or phenomenon in the first sample is at least 90% lower than the quantity of the same substance and/or phenomenon in a second sample. Alternatively, a difference may be expressed as an "n-fold" difference.

A number of terms herein relate to cancer. "Cancer" is intended herein to encompass all forms of abnormal or improperly regulated reproduction of cells in a subject. "Subject" and "patient" are used herein interchangeably, and a subject may be any mammal but is preferably a human. A "reference subject" herein refers to an individual who does not have cancer. The "reference subject" thereby provides a basis to which another cell (for example a cancer cell) can be compared.

The growth of cancer cells ("growth" herein referring generally to cell division but also to the growth in size of masses of cells) is characteristically uncontrolled or inadequately controlled, as is the death ("apoptosis") of such cells. Local accumulations of such cells result in a tumor. More broadly, and still denoting "tumors" herein are accumulations ranging from a cluster of lymphocytes at a site of infection to vascularized overgrowths, both benign and malignant. A "malignant" tumor (as opposed to a "benign" tumor) herein comprises cells that tend to migrate to nearby tissues, including cells that may travel through the circulatory system to invade or colonize tissues or organs at considerable remove from their site of origin in the "primary tumor," so-called herein. Metastatic cells are adapted to penetrate blood vessel wells to enter ("intravasate") and exit ("extravasate") blood vessels. Tumors capable of releasing such cells are also referred to herein as "metastatic." The term is used herein also to denote any cell in such a tumor that is capable of such travel, or that is en route, or that has established a foothold in a target tissue. For example, a metastatic breast cancer cell that has taken root in the lung is referred to herein as a "lung metastasis." Metastatic cells may be identified herein by their respective sites of origin and destination, such as "breast-to-bone metastatic." In the target tissue, a colony of metastatic cells can grow into a "secondary tumor," so called herein. Primary tumors are thought to derive from a benign or normal cell through a process referred to herein as "cancer progression." According to this view, the transformation of a normal cell to a cancer cell requires changes (usually many of them) in the cell's biochemistry. The changes are reflected clinically as the disease progresses through stages. Even if a tumor is "clonogenic" (as used herein, an accumulation of the direct descendants of a parent cell), the biochemistry of the accumulating cells changes in successive generations, both because the expression of the genes (controlled by so-called "epigenetic" systems) of these cells becomes unstable and because the genomes themselves change. In normal somatic cells, the genome (that is, all the genes of an individual) is stored in the chromosomes of each cell (setting aside the mitochondrial genome). The number of copies of any particular gene is largely invariant from cell to cell. By contrast, "genomic instability" is characteristic of cancer progression. A genome in a cancer cell can gain ("genomic gain") or lose ("genomic loss") genes, typically because an extra copy of an entire chromosome appears ("trisomy") or a region of a chromosome replicates itself ("genomic gain" or, in some cases, "genomic amplification") or drops out when the cell divides. Thus, the "copy number" of a gene or a set of genes, largely invariant among normal cells, is likely to change in cancer cells (referred to herein as a "genomic event"), which affects the total expression of the gene or gene set and the biological behavior ("phenotype") of descendent cells. Thus, in cancer cells, "gene activity" herein is determined not only by the multiple "layers" of epigenetic control systems and signals that call forth expression of the gene but by the number of times that gene appears in the genome. The term "epigenetic" herein refers to any process in an individual that, in operation, affects the expression of a gene or a set of genes in that individual, and stands in contrast to the "genetic" processes that govern the inheritance of genes in successive generations of cells or individuals.

Certain regions of chromosomes, depending upon the specific type of cancer, have proven to be hot spots for genomic gain inasmuch as increases in copy number in the genomes of cells from multiple donors tend to occur in one or a few specific regions of a specific chromosome. Such hot spots are referred to herein as sites of "recurrent genomic gain." The term is to be distinguished from "recurrent cancer," which refers to types of cancer that are likely to recur after an initial course of therapy, resulting in a "relapse." A number of terms herein relate to methods that enable the practitioner to examine many distinct genes at once. By these methods, sets of genes ("gene sets") have been identified wherein each set has biologically relevant and distinctive properties as a set. Devices (which may be referred to herein as "platforms") in which each gene in a significant part of an entire genome is isolated and arranged in an array of spots, each spot having its own "address," enable one to detect, quantitatively, many thousands of the genes in a cell. More precisely, these "microarrays" typically detect expressed genes (an "expressed" gene is one that is actively transmitting its unique biochemical signal to the cell in which the gene resides). Microarray data, inasmuch as they display the expression of many genes at once, permit the practitioner to view "gene expression profiles" in a cell and to compare those profiles cell-to-cell to perform so-called "comparative analyses of expression profiles." Such microarray-based "expression data" are capable of identifying genes that are "over-expressed" (or under-expressed) in, for example, a disease condition. An over-expressed gene may be referred to herein as having a high "expression score."

The aforementioned methods for examining gene sets employ a number of well-known methods in molecular biology, to which references are made herein. A gene is a heritable chemical code resident in, for example, a cell, virus, or bacteriophage that an organism reads (decodes, decrypts, transcribes) as a template for ordering the structures of biomolecules that an organism synthesizes to impart regulated function to the organism. Chemically, a gene is a heteropolymer comprised of subunits ("nucleotides") arranged in a specific sequence. In cells, such heteropolymers are deoxynucleic acids ("DNA") or ribonucleic acids ("RNA"). DNA forms long strands. Characteristically, these strands occur in pairs. The first member of a pair is not identical in nucleotide sequence to the second strand, but complementary. The tendency of a first strand to bind in this way to a complementary second strand (the two strands are said to "anneal" or "hybridize"), together with the tendency of individual nucleotides to line up against a single strand in a complementarily ordered manner accounts for the replication of DNA.

Experimentally, nucleotide sequences selected for their complementarity can be made to anneal to a strand of DNA containing one or more genes. A single such sequence can be employed to identify the presence of a particular gene by attaching itself to the gene. This so called "probe" sequence is adapted to carry with it a "marker" that the investigator can readily detect as evidence that the probe struck a target. As used herein, the term "marker" relates to any surrogate the artisan may use to "observe" an event or condition that is difficult or impossible to detect directly. In some contexts herein, the marker is said to "target" the condition or event. In other contexts, the condition or event is referred to as the target for the marker. Sequences used as probes may be quite small (e.g., "oligonucleotides" of <20 nucleotides) or quite large (e.g., a sequence of 100,000 nucleotides in DNA from a "bacterial artificial chromosome" or "BAC"). A BAC is a bacterial chromosome (or a portion thereof) with a "foreign" (typically, human) DNA fragment inserted in it. BACs are employed in a technique referred to herein as "fluorescence in situ hybridization" or "FISH." A BAC or a portion of a BAC is constructed that has (1) a sequence complementary to a region of interest on a chromosome and (2) a marker whose presence is discernible by fluorescence. The chromosomes of a cell or a tissue are isolated (on a glass slide, for example) and treated with the BAC construct. Excess construct is washed away and the chromosomes examined microscopically to find chromosomes or, more particularly, identifiable regions of chromosomes that fluoresce.

Alternatively, such sequences can be delivered in pairs selected to hybridize with two specific sequences that bracket a gene sequence. A complementary strand of DNA then forms between the "primer pair." In one well-known method, the "polymerase chain reaction" or "PCR," the formation of complementary strands can be made to occur repeatedly in an exponential amplification. A specific nucleotide sequence so amplified is referred to herein as the "amplicon" of that sequence. "Quantitative PCR" or "qPCR" herein refers to a version of the method that allows the artisan not only to detect the presence of a specific nucleic acid sequence but also to quantify how many copies of the sequence are present in a sample, at least relative to a control. As used herein, "qRT-PCR" may refer to "quantitative real-time PCR," used interchangeably with "qPCR" as a technique for quantifying the amount of a specific DNA sequence in a sample. However, if the context so admits, the same abbreviation may refer to "quantitative reverse transcriptase PCR," a method for determining the amount of messenger RNA present in a sample. Since the presence of a particular messenger RNA in a cell indicates that a specific gene is currently active (being expressed) in the cell, this quantitative technique finds use, for example, in gauging the level of expression of a gene.

Collectively, the genes of an organism constitute its genome. The term "genomic DNA" may refer herein to the entirety of an organism's DNA or to the entirety of the nucleotides comprising a single gene in an organism. A gene typically contains sequences of nucleotides devoted to coding ("exons"), and non-coding sequences that contribute in one way or another to the decoding process ("introns").

The term "gene" refers to a nucleic acid (e.g., DNA) comprising covalently linked nucleotide monomers arranged in a particular sequence that comprises a coding sequence necessary for the production of a polypeptide or precursor or RNA (e.g., tRNA, siRNA, rRNA, etc.). The polypeptide can be encoded by a full-length coding sequence or by any portion of the coding sequence so long as the desired activities or functional properties (e.g., enzymatic activity, ligand binding, signal transduction, etc.) of the full-length or fragment are retained. The term also encompasses the coding region together with the sequences located adjacent to the coding region on both the 5' and 3' ends, such that the gene corresponds to the length of the full-length mRNA (also referred to as "pre-mRNA," "nuclear RNA," or "primary transcript RNA") transcribed from it. The sequences that are located 5' of the coding region and are present on the mRNA are referred to as 5' untranslated sequences. The sequences that are located 3' or downstream of the coding region and that are present on the mRNA are referred to as 3' untranslated sequences. The term "gene" encompasses both cDNA (the coding region(s) only) and genomic forms of a gene. A genomic form or clone of a gene contains the coding region, which may be interrupted with non-coding sequences termed "introns" or "intervening regions" or "intervening sequences." Introns are removed or "spliced out" from the nuclear or primary transcript, and are therefore absent in the messenger RNA (mRNA) transcript. The mRNA functions during translation to specify the sequence or order of amino acids in a nascent polypeptide.

Encoding in DNA (and messenger RNA) is accomplished by 3-membered nucleotide sequences called "codons." Each codon encrypts an amino acid, and the sequence of codons encrypts the sequence of amino acids that identifies a particular protein. The code for a given gene is embedded in a (usually) much longer nucleotide sequence and is distinguishable to the cell's decoding system from the longer sequence by a "start codon" and a "stop" codon. The decoding system reads the sequence framed by these two codons (the so-called "open reading frame"). The readable code is transcribed into messenger RNA which itself comprises sites that ensure coherent translation of the code from nucleic acid to protein. In particular, the open reading frame is delimited by a so-called "translation initiation" codon and "translation termination" codon.

The term "plasmid" as used herein, refers to a small, independently replicating, piece of DNA Similarly, the term "naked plasmid" refers to plasmid DNA devoid of extraneous material typically used to effect transfection. As used herein, a "naked plasmid" refers to a plasmid substantially free of calcium-phosphate, DEAE-dextran, liposomes, and/or polyamines. As used herein, the term "purified" refers to molecules (polynucleotides or polypeptides) that are removed from their natural environment, isolated or separated. "Purified" molecules are at least 50% free, preferably at least 75% free, and more preferably at least 90% free from other components with which they are naturally associated.

The term "recombinant DNA" refers to a DNA molecule that is comprised of segments of DNA joined together by means of molecular biology techniques. Similarly, the term "recombinant protein" refers to a protein molecule that is expressed from recombinant DNA.

The term "fusion protein" as used herein refers to a protein formed by expression of a hybrid gene made by combining two gene sequences. Typically this is accomplished by cloning a cDNA into an expression vector in frame (i.e., in an arrangement that the cell can transcribe as a single mRNA molecule) with an existing gene. The fusion partner may act as a reporter (e.g., (βgal) or may provide a tool for isolation purposes (e.g., GST).

Where an amino acid sequence is recited herein to refer to an amino acid sequence of a protein molecule, "amino acid sequence" and like terms, such as "polypeptide" or "protein" are not meant to limit the amino acid sequence to the complete, native amino acid sequence associated with the recited protein molecule. Rather the terms "amino acid sequence" and "protein" encompass partial sequences, and modified sequences.

The term "wild type" refers to a gene or gene product that has the characteristics of that gene or gene product when isolated from a naturally occurring source. A wild type gene is the variant most frequently observed in a population and is thus arbitrarily designed the "normal" or "wild-type" form of the gene.

In contrast, the terms "modified," "mutant," and "variant" (when the context so admits) refer to a gene or gene product that displays modifications in sequence and or functional properties (i.e., altered characteristics) when compared to the wild-type gene or gene product. In some embodiments, the modification comprises at least one nucleotide insertion, deletion, or substitution.

The term "homology" refers to a degree of complementarity. There may be partial homology or complete homology (i.e., identity). A partially complementary sequence is one that at least partially inhibits a completely complementary sequence from hybridizing to a target nucleic acid and is referred to using the functional term "substantially homologous." The term "inhibition of binding," when used in reference to nucleic acid binding, refers to reduction in binding caused by competition of homologous sequences for binding to a target sequence. The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous sequence to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target that lacks even a partial degree of complementarity (e.g., less than about 30% identity); in the absence of non-specific binding the probe will not hybridize to the second non-complementary target. When used in reference to a single-stranded nucleic acid sequence, the term "substantially homologous" refers to any probe that can hybridize (i.e., it is the complement of) the single-stranded nucleic acid sequence under conditions of low stringency as described above.

As used herein, the term "competes for binding" when used in reference to a first and a second polypeptide means that the first polypeptide with an activity binds to the same substrate as does the second polypeptide with an activity. In one embodiment, the second polypeptide is a variant of the first polypeptide (e.g., encoded by a different allele) or a related (e.g., encoded by a homolog) or dissimilar (e.g., encoded by a second gene having no apparent relationship to the first gene) polypeptide. The efficiency (e.g., kinetics or thermodynamics) of binding by the first polypeptide may be the same as or greater than or less than the efficiency of substrate binding by the second polypeptide. For example, the equilibrium binding constant ($K_D$) for binding to the substrate may be different for the two polypeptides.

As used herein, the term "hybridization" refers to the pairing of complementary nucleic acids. Hybridization and the strength of hybridization (i.e., the strength of the association between the nucleic acids) is impacted by such factors as the degree of complementarity between the nucleic acids, stringency of the conditions involved, the $T_m$ of the formed hybrid, and the G:C ratio within the nucleic acids.

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41(\% \text{ G}+\text{C})$, when a nucleic acid is in aqueous solution at 1 M NaCl (See e.g., Anderson and Young, Quantitative Filter Hybridization, in Nucleic Acid Hybridization [1985]). Other references include more sophisticated computations that take structural as well as sequence characteristics into account for the calculation of $T_m$.

As used herein the term "stringency" is used in reference to the conditions of temperature, ionic strength, and the presence of other compounds such as organic solvents, under which nucleic acid hybridizations are conducted. Those skilled in the art will recognize that "stringency" conditions may be altered by varying the parameters just described either individually or in concert. With "high stringency" conditions, nucleic acid base pairing will occur only between nucleic acid fragments that have a high frequency of complementary base sequences (e.g., hybridization under "high stringency" conditions may occur between homologs with 85-100% identity, preferably 70-100% identity). With medium stringency conditions, nucleic acid base pairing will occur between nucleic acids with an intermediate frequency of complementary base sequences (e.g., hybridization under "medium stringency" conditions may occur between homologs with 50-70% identity). Thus, conditions of "weak" or "low" stringency are often required with nucleic acids that are derived from organisms that are genetically diverse, as the frequency of complementary sequences is usually less.

"High stringency conditions" when used in reference to nucleic acid hybridization comprise conditions equivalent to binding or hybridization at 42° C. in a solution comprising 5×SSPE (43.8 g/l NaCl, 6.9 g/l NaH$_2$PO$_4$H$_2$O and 1.85 g/l EDTA, pH adjusted to 7.4 with NaOH), 0.5% SDS, 5×Denhardt's reagent and 100 µg/ml denatured salmon sperm DNA followed by washing in a solution comprising 0.1×SSPE, 1.0% SDS at 42° C. when a probe of about 100 to about 1000 nucleotides in length is employed.

"Medium stringency conditions" when used in reference to nucleic acid hybridization comprise conditions equivalent to binding or hybridization at 42° C. in a solution comprising 5×SSPE (43.8 g/l NaCl, 6.9 g/l NaH$_2$PO$_4$H$_2$O and 1.85 g/l EDTA, pH adjusted to 7.4 with NaOH), 0.5% SDS, 5×Denhardt's reagent and 100 µg/ml denatured salmon sperm DNA followed by washing in a solution comprising 1.0×SSPE, 1.0% SDS at 42° C. when a probe of about 100 to about 1000 nucleotides in length is employed.

"Low stringency conditions" comprise conditions equivalent to binding or hybridization at 42° C. in a solution comprising 5×SSPE (43.8 g/l NaCl, 6.9 g/l NaH$_2$PO$_4$H$_2$O and 1.85 g/l EDTA, pH adjusted to 7.4 with NaOH), 0.1% SDS, 5×Denhardt's reagent [50×Denhardt's contains per 500 ml: 5 g Ficoll (Type 400, Pharamcia), 5 g BSA (Fraction V; Sigma)] and 100 g/ml denatured salmon sperm DNA followed by washing in a solution comprising 5×SSPE, 0.1% SDS at 42° C. when a probe of about 100 to about 1000 nucleotides in length is employed.

The term "equivalent" when made in reference to a hybridization condition as it relates to a hybridization condition of interest means that the hybridization condition and the hybridization condition of interest result in hybridization of nucleic acid sequences which have the same range of percent (%) homology. For example, if a hybridization condition of interest results in hybridization of a first nucleic acid sequence with other nucleic acid sequences that have from 85% to 95% homology to the first nucleic acid sequence, then another hybridization condition is said to be equivalent to the hybridization condition of interest if this other hybridization condition also results in hybridization of the first nucleic acid sequence with the other nucleic acid sequences that have from 85% to 95% homology to the first nucleic acid sequence.

The following terms are used to describe the sequence relationships between two or more polynucleotides: "reference sequence", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA sequence given in a sequence listing or may comprise a complete gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window", as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman (Smith and Waterman, Adv. Appl. Math., 2: 482, 1981) by the homology alignment algorithm of Needleman and Wunsch (Needleman and Wunsch, I Mol. Biol. 48:443, 1970), by the search for similarity method of Pearson and Lipman (Pearson and Lipman, Proc. Natl. Acad. Sci., U.S.A., 85:2444, 1988), by computerized implementations of these algorithms (GAP, BESTFIT, FASTA, and TFASTA in the Wisconsin Genetics Software Package Release 7.0, Genetics Computer Group, Madison, Wis.), or by inspection, and the best alignment (i.e., resulting in the highest percentage of homology over the comparison window) generated by the various methods is selected. The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 25-50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence, for example, as a segment of the full-length sequences of the compositions claimed in the present invention.

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (e.g., 99 percent sequence identity). Preferably, residue positions which are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic hydroxyl side chains is serine and threonine; a group of amino acids having amide-containing side chains is asparagine and glutamine; a group of amino acids having aromatic side chains is phenylalanine, tyrosine, and tryptophan; a group of amino acids having acidic side chains is glutamic acid and aspartic acid; a group of amino acids having basic side chains is lysine, arginine, and histidine; and a group of amino acids having sulfur-containing side chains is cysteine and methionine Preferred conservative amino acids substitution groups are: valine-leucine-isoleucine, phenylalanine-tyrosine, lysine-arginine, alanine-valine, and asparagine-glutamine.

"Amplification" is used herein in two different ways. A given gene typically appears in a genome once, on one chromosome. Since chromosomes in somatic cells of eukaryotes are in general paired, two copies or alleles of each gene are found. In some conditions, such as cancer, replication of chromosome pairs during cell division is disturbed so that multiple copies of a gene or chromosome accrue over successive generations. The phenomenon is referred to generally (and herein) as "amplification."

In the context of molecular biological experimentation, the term is used differently. Experimentally, "amplification" is used in relation to a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid Amplification techniques have been designed primarily for this sorting out.

Template specificity is achieved in most amplification techniques by the choice of enzyme. Amplification enzymes are enzymes that, under the conditions in which they are used, will process only specific sequences of nucleic acids in a heterogeneous mixture of nucleic acids. In particular, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences.

As used herein, the term "sample template" refers to nucleic acid originating from a sample that is analyzed for the presence of "target" (defined below). In contrast, "background template" is used in reference to nucleic acid other than sample template that may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, that is capable of hybridizing to another oligonucleotide of interest. A probe may be single-stranded or double-stranded. Probes are useful in the detection, identification and isolation of particular sequences. It is contemplated that any probe used in the present invention will be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein, the term "target," when used in reference to the polymerase chain reaction, refers to the region of nucleic acid bounded by the primers used for polymerase chain reaction. Thus, the "target" is sought to be sorted out from other nucleic acid sequences. A "segment" is defined as a region of nucleic acid within the target sequence.

As used herein, the term "polymerase chain reaction" ("PCR") refers to the method of Mullis (U.S. Pat. Nos. 4,683,195, 4,683,202, and 4,965,188, hereby incorporated by reference), that describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing, and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified."

As used herein, the terms "restriction endonucleases" and "restriction enzymes" refer to bacterial enzymes, each of which cut double-stranded DNA at or near a specific nucleotide sequence.

The term "isolated" when used in relation to a nucleic acid, as in "an isolated oligonucleotide" or "isolated polynucleotide" refers to a nucleic acid sequence that is identified and separated from at least one contaminant nucleic acid with which it is ordinarily associated in its natural source. Isolated nucleic acid is present in a form or setting that is different from that in which it is found in nature. In contrast, non-isolated nucleic acids are nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding gene includes, by way of example, such nucleic acid in cells ordinarily expressing gene where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may single-stranded), but may contain both the sense and anti-sense strands (i.e., the oligonucleotide or polynucleotide may be double-stranded).

The terms "fragment" and "portion" when used in reference to a nucleotide sequence (as in "a portion of a given nucleotide sequence") refers to partial segments of that sequence. The fragments may range in size from four nucleotides to the entire nucleotide sequence minus one nucleotide (10 nucleotides, 20, 30, 40, 50, 100, 200, etc.).

Similarly, the terms "fragment" and "portion" when used in reference to a polypeptide sequence refers to partial segments of that sequence. In some embodiments, the portion has an amino-terminal and/or carboxy-terminal deletion as compared to the native protein, but where the remaining amino acid sequence is identical to the corresponding positions in the amino acid sequence deduced from a full-length cDNA sequence. Fragments are preferably at least 4 amino acids long, more preferably at least 50 amino acids long, and most preferably at least 50 amino acids long or longer (the entire amino acid sequence minus on amino acid). In particularly preferred embodiments, the portion comprises the amino acid residues required for intermolecular binding of the compositions of the present invention with its various ligands and/or substrates.

As used herein the term "portion" when in reference to a protein (as in "a portion of a given protein") refers to fragments of that protein. The fragments may range in size from four consecutive amino acid residues to the entire amino acid sequence minus one amino acid.

As used herein the term "coding region" when used in reference to structural gene refers to the nucleotide sequences that encode the amino acids found in the nascent polypeptide as a result of translation of a mRNA molecule. The coding region is bounded, in eukaryotes, on the 5' side by the nucleotide triplet "ATG" that encodes the initiator methionine and on the 3' side by one of the three triplets which specify stop codons (i.e., TAA, TAG, TGA).

The term "recombinant DNA molecule" as used herein refers to a DNA molecule that is comprised of segments of DNA joined together by means of molecular biological techniques. Similarly, the term "recombinant protein" or "recombinant polypeptide" as used herein refers to a protein molecule that is expressed from a recombinant DNA molecule.

The term "native protein" as used herein to indicate that a protein does not contain amino acid residues encoded by vector sequences, that are the native protein contains only those amino acids found in the protein as it occurs in nature. A native protein may be produced by recombinant means or may be isolated from a naturally occurring source.

The term "Southern blot," refers to the analysis of DNA on agarose or acrylamide gels to fractionate the DNA according to size followed by transfer of the DNA from the gel to a solid support, such as nitrocellulose or a nylon membrane. The immobilized DNA is then probed with a labeled probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists (Sambrook et al., Molecular Cloning: A Laboratory Manual, Cold Spring Harbor Press, NY, pp. 9.31-9.58, 1989).

The term "Northern blot," as used herein refers to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled probe to detect RNA species complementary to the probe used. Northern blots are a standard tool of molecular biologists (Sambrook, et al., supra, pp. 7.39-7.52, 1989).

The term "Western blot" refers to the analysis of protein(s) (or polypeptides) immobilized onto a support such as nitrocellulose or a membrane. The proteins are run on acrylamide gels to separate the proteins, followed by transfer of the protein from the gel to a solid support, such as nitrocellulose or a nylon membrane. The immobilized proteins are then exposed to antibodies with reactivity against an antigen of interest. The binding of the antibodies may be detected by various methods, including the use of radiolabelled antibodies As used herein, the term "transgenic" refers to a cell or organism whose genome has been heritably altered by genetically engineering into the genome a gene ("transgene") not normally part of it or removing from it a gene ordinarily present (a "knockout" gene). The "transgene" or "foreign gene" may be placed into an organism by introducing it into newly fertilized eggs or early embryos. The term "foreign gene" refers to any nucleic acid (e.g., gene sequence) that is introduced into the genome of an animal by experimental manipulations and may include gene sequences found in that animal so long as the introduced gene does not reside in the same location as does the naturally-occurring gene.

As used herein, the term "vector" is used in reference to nucleic acid molecules that transfer DNA segment(s) from one cell to another. The term "vehicle" is sometimes used interchangeably with "vector."

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

As used herein, the term host cell refers to any eukaryotic or prokaryotic cell (e.g. bacterial cells such as *E. coli*, yeast cells, mammalian cells, avian cells, amphibian cells, plant cells, fish cells, and insect cells), whether located in vitro or in vivo. For example, host cells may be located in a transgenic animal.

The term "transfection" as used herein refers to the introduction of foreign DNA into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "stable transfection" or "stably transfected" refers to the introduction and integration of foreign DNA into the genome of the transfected cell. The term "stable transfectant" refers to a cell that has stably integrated foreign DNA into the genomic DNA.

The term "transient transfection" or "transiently transfected" refers to the introduction of foreign DNA into a cell where the foreign DNA fails to integrate into the genome of the transfected cell in the sense that the foreign DNA will be passed on to daughter cells. The term encompasses transfections of foreign DNA into the cytoplasm only. In general, however, the foreign DNA reaches the nucleus of the transfected cell and persists there for several days. During this time the foreign DNA is subject to the regulatory controls that govern the expression of endogenous genes in the chromosomes. The term "transient transfectant" refers to cells that have taken up foreign DNA but have failed to integrate this DNA. The term "transient transfection" encompasses transfection of foreign DNA into the cytoplasm only The term "calcium phosphate co-precipitation" refers to a technique for the introduction of nucleic acids into a cell. The uptake of nucleic acids by cells is enhanced when the nucleic acid is presented as a calcium phosphate-nucleic acid co-precipitate. The original technique of is modified to optimize conditions for particular types of cells. The art is well aware of these numerous modifications.

A "composition comprising a given polynucleotide sequence" as used herein refers broadly to any composition containing the given polynucleotide sequence. Such compositions may be employed as hybridization probes, typically in an aqueous solution containing salts (e.g., NaCl), detergents (e.g., SDS), and other components (e.g., Denhardt's solution, dry milk, salmon sperm DNA, etc.).

The terms "N-terminus" "NH$_2$-terminus" and "amino-terminus" refer to the amino acid residue corresponding to the methionine encoded by the start codon (e.g., position or residue 1). In contrast the terms "C-terminus" "COOH-terminus" and "carboxy terminus" refer to the amino acid residue encoded by the final codon (e.g., last or final residue prior to the stop codon).

The term "conservative substitution" as used herein refers to a change that takes place within a family of amino acids that are related in their side chains. Genetically encoded amino acids can be divided into four families: (1) acidic (aspartate, glutamate); (2) basic (lysine, arginine, histidine); (3) nonpolar (alanine, valine, leucine, isoleucine, proline, phenylalanine, methionine, tryptophan); and (4) uncharged polar (glycine, asparagine, glutamine, cysteine, serine, threonine, tyrosine). Phenylalanine, tryptophan, and tyrosine are sometimes classified jointly as aromatic amino acids. In similar fashion, the amino acid repertoire can be grouped as (1) acidic (aspartate, glutamate); (2) basic (lysine, arginine, histidine), (3) aliphatic (glycine, alanine, valine, leucine, isoleucine, serine, threonine), with serine and threonine optionally be grouped separately as aliphatic-hydroxyl; (4) aromatic (phenylalanine, tyrosine, tryptophan); (5) amide (asparagine, glutamine); and (6) sulfur-containing (cysteine and methionine). Whether a change in the amino acid sequence of a peptide results in a functional homolog can be readily determined by assessing the ability of the variant peptide to function in a fashion similar to the wild-type protein. Peptides having more than one replacement can readily be tested in the same manner. In contrast, the term "non-conservative substitution" refers to a change in which an amino acid from one family is replaced with an amino acid from another family (e.g., replacement of a glycine with a tryptophan). Guidance in determining which amino acid residues can be substituted, inserted, or deleted without abolishing biological activity can be found using computer programs (e.g., LASERGENE software, DNASTAR Inc., Madison, Wis.

A peptide sequence and nucleotide sequence may be "endogenous" or "heterologous" (i.e., "foreign"). The term "endogenous" refers to a sequence which is naturally found in the cell or virus into which it is introduced so long as it does not contain some modification relative to the naturally-occurring sequence. The term "heterologous" refers to a sequence which is not endogenous to the cell or virus into which it is introduced. For example, heterologous DNA includes a nucleotide sequence which is ligated to, or is manipulated to become ligated to, a nucleic acid sequence to which it is not ligated in nature, or to which it is ligated at a different location in nature. Heterologous DNA also includes a nucleotide sequence which is naturally found in the cell or virus into which it is introduced and which contains some modification relative to the naturally-occurring sequence. Generally, although not necessarily, heterologous DNA encodes heterologous RNA and heterologous proteins that are not normally produced by the cell or virus into which it is introduced. Examples of heterologous DNA include reporter genes, transcriptional and translational regulatory sequences, DNA sequences which encode selectable marker proteins (e.g., proteins which confer drug resistance), etc. In preferred embodiments, the terms "heterologous antigen" and "heterologous sequence" refer to a non-hepadna virus antigen or amino acid sequence including but not limited to microbial antigens, mammalian antigens and allergen antigens.

The terms "peptide," "peptide sequence," "amino acid sequence," "polypeptide," and "polypeptide sequence" are used interchangeably herein to refer to at least two amino acids or amino acid analogs which are covalently linked by a peptide bond or an analog of a peptide bond. The term peptide includes oligomers and polymers of amino acids or amino acid analogs. The term peptide also includes molecules which are commonly referred to as peptides, which generally contain from about two (2) to about twenty (20) amino acids. The term peptide also includes molecules which are commonly referred to as polypeptides, which generally contain from about twenty (20) to about fifty amino acids (50). The term peptide also includes molecules which are commonly referred to as proteins, which generally contain from about fifty (50) to about three thousand (3000) amino acids. The amino acids of the peptide may be L-amino acids or D-amino acids. A peptide, polypeptide or protein may be synthetic, recombinant or naturally occurring. A synthetic peptide is a peptide which is produced by artificial means in vitro The terms "oligosaccharide" and "OS" antigen refer to a carbohydrate comprising up to ten component sugars, either O or N linked to the next sugar. Likewise, the terms "polysaccharide" and "PS" antigen refer to polymers of more than ten monosaccharide residues linked glycosidically in branched or unbranched chains As used herein, the term "mammalian sequence" refers to synthetic, recombinant or purified sequences (preferably sequence fragments comprising at least one B cell epitope) of a mammal. Exemplary mammalian sequences include cytokine sequence, MHC class I heavy chain sequences, MHC class II alpha and beta chain sequences, and amyloid β-peptide sequences.

The terms "mammals" and "mammalian" refer animals of the class mammalia which nourish their young by fluid secreted from mammary glands of the mother, including human beings. The class "mammalian" includes placental animals, marsupial animals, and monotrematal animals. An exemplary "mammal" may be a rodent, primate (including simian and human) ovine, bovine, ruminant, lagomorph, porcine, caprine, equine, canine, feline, ave, etc. Preferred non-human animals are selected from the order Rodentia.

Preferred embodiments of the present invention are primarily directed to vertebrate (backbone or notochord) members of the animal kingdom.

The terms "patient" and "subject" refer to a mammal that may be treated using the methods of the present invention.

The term "control" refers to subjects or samples which provide a basis for comparison for experimental subjects or samples. For instance, the use of control subjects or samples permits determinations to be made regarding the efficacy of experimental procedures. In some embodiments, the term "control subject" refers to a subject that which receives a mock treatment (e.g., saline alone).

The terms "diluent" and "diluting agent" as used herein refer to agents used to diminish the strength of an admixture. Exemplary diluents include water, physiological saline solution, human serum albumin, oils, polyethylene glycols, glycerine, propylene glycol or other synthetic solvents, antibacterial agents such as benzyl alcohol, antioxidants such as ascorbic acid or sodium bisulphite, chelating agents such as ethylene diamine-tetra-acetic acid, buffers such as acetates, citrates or phosphates and agents for adjusting the osmolarity, such as sodium chloride or dextrose.

The terms "carrier" and "vehicle" as used herein refer to usually inactive accessory substances into which a pharmaceutical substance is suspended. Exemplary carriers include liquid carriers (such as water, saline, culture medium, saline, aqueous dextrose, and glycols) and solid carriers (such as carbohydrates exemplified by starch, glucose, lactose, sucrose, and dextrans, anti-oxidants exemplified by ascorbic acid and glutathione, and hydrolyzed proteins.

The term "derived" when in reference to a peptide derived from a source (such as a microbe, cell, etc.) as used herein is intended to refer to a peptide which has been obtained (e.g., isolated, purified, etc.) from the source. Alternatively, or in addition, the peptide may be genetically engineered and/or chemically synthesized.

The terms "operably linked," "in operable combination" and "in operable order" as used herein refer to the linkage of nucleic acid sequences such that they perform their intended function. For example, operably linking a promoter sequence to a nucleotide sequence of interest refers to linking the promoter sequence and the nucleotide sequence of interest in a manner such that the promoter sequence is capable of directing the transcription of the nucleotide sequence of interest and/or the synthesis of a polypeptide encoded by the nucleotide sequence of interest. Similarly, operably linking a nucleic acid sequence encoding a protein of interest means linking the nucleic acid sequence to regulatory and other sequences in a manner such that the protein of interest is expressed. The term also refers to the linkage of amino acid sequences in such a manner so that a functional protein is produced.

The terms "C-terminal portion," "COOH-terminal portion," "carboxy terminal portion," "C-terminal domain," "COOH-terminal domain," and "carboxy terminal domain," when used in reference to an amino acid sequence of interest refer to the amino acid sequence (and portions thereof that is located from approximately the middle of the amino acid sequence of interest to the C-terminal-most amino acid residue of the sequence of interest. The terms "specific binding," "binding specificity," and grammatical equivalents thereof when made in reference to the binding of a first molecule (such as a polypeptide, glycoprotein, nucleic acid sequence, etc.) to a second molecule (such as a polypeptide, glycoprotein, nucleic acid sequence, etc.) refer to the preferential interaction between the first molecule with the second molecule as compared to the interaction between the second molecule with a third molecule. Specific binding is a relative term that does not require absolute specificity of binding; in other words, the term "specific binding" does not require that the second molecule interact with the first molecule in the absence of an interaction between the second molecule and the third molecule. Rather, it is sufficient that the level of interaction between the first molecule and the second molecule is higher than the level of interaction between the second molecule with the third molecule. "Specific binding" of a first molecule with a second molecule also means that the interaction between the first molecule and the second molecule is dependent upon the presence of a particular structure on or within the first molecule; in other words the second molecule is recognizing and binding to a specific structure on or within the first molecule rather than to nucleic acids or to molecules in general. For example, if a second molecule is specific for structure "A" that is on or within a first molecule, the presence of a third nucleic acid sequence containing structure A will reduce the amount of the second molecule which is bound to the first molecule.

For example, the term "has the biological activity of a specifically named protein" when made in reference to the biological activity of a variant of the specifically named protein refers, for example, to a quantity of binding of an antibody that is specific for the specifically named protein to the variant which is preferably greater than 50% (preferably from 50% to 500%, more preferably from 50% to 200%, most preferably from 50% to 100%), as compared to the quantity of binding of the same antibody to the specifically named protein.

Reference herein to any specifically named nucleotide sequence includes within its scope fragments, homologs, and sequences that hybridize under stringent condition to the specifically named nucleotide sequence. The term "homolog" of a specifically named nucleotide sequence refers to an oligonucleotide sequence which exhibits greater than or equal to 50% identity to the sequence of interest. Alternatively, or in addition, a homolog of any specifically named nucleotide sequence is defined as an oligonucleotide sequence which has at least 95% identity with the sequence of the nucleotide sequence in issue. In another embodiment, the sequence of the homolog has at least 90% identity, and preferably at least 85% identity with the sequence of the nucleotide sequence in issue.

Exons, introns, genes and entire gene-sets are characteristically locatable with respect to one another. That is, they have generally invariant "genomic loci" or "genomic positions." Genes distributed across one or several chromosomes can be mapped to specific locations on specific chromosomes. The field of "cytogenetics" addresses several aspects of gene mapping. First, optical microscopy reveals features of chromosomes that are useful as addresses for genes. In humans, chromosomes are morphologically distinguishable from one another and each (except for the Y-chromosome) has two distinct arms separated by a "centromere." Each arm has distinctive "bands" occupied by specific genes. Disease-related changes in chromosome number and changes in banding form the basis for diagnosing a number of diseases. "Microdissection" of chromosomes and DNA analysis of the microdissected fragments have connected specific DNA sequences to specific locations on chromosomes. In cancer, a region of a chromosome may duplicate or amplify itself or drop out entirely. FISH, mentioned above, and "comparative genomic hybridization" ("CGH") have extended the reach of cytogenetic analysis to the extent of measuring genome alterations within and between individuals. CGH, for example, in which chromosomes from a normal cell are hybridized with a corresponding preparation from a cancer cell provides a means of directly determining cancer-related differences in copy number of chromosomal regions.

"Targeted therapeutics" is used herein to denote any therapeutic modality that affects only or primarily only the cells or tissues selected ("targeted") for treatment. A monoclonal antibody specific for an antigen expressed only by a target (if retained by the target) is highly useful in targeted therapeutics. In the case of unwanted cells such as cancer cells, if the antibody doesn't induce destruction of the target directly, it may do so indirectly by carrying to the target, for example, an agent coupled to the antibody. On the other hand, agents that suppress processes that tend to promote uncontrolled proliferation of cells ("antineoplastic agents") can be delivered to target sites in this manner.

The term "agent" is used herein in its broadest sense to refer to a composition of matter, a process or procedure, a device or apparatus employed to exert a particular effect. By way of non-limiting example, a surgical instrument may be employed by a practitioner as an "excising" agent to remove tissue from a subject; a chemical may be used as a pharmaceutical agent to remove, damage or neutralize the function of a tissue, etc. Such pharmaceutical agents are said to be "anti-cellular." Cells may be removed by an agent that promotes apoptosis. A variety of toxic agents, including other cells (e.g., cytotoxic T-cell lymphocytes) and their secretions, and a plethora of chemical species, can damage cells.

The term "by-stander", as used herein, refers to a process or event initiated or affected by another, causative event or process The term "knockdown", as used herein, refers to a method of selectively preventing the expression of a gene in an individual.

The term "oncogene", as used herein, refers to any gene that regulates a process affecting the suppression of abnormal proliferative events.

The term "single nucleotide polymorphism" or "SNP", as used herein, refers to a DNA sequence variation occurring when a single nucleotide in the genome (or other shared sequence) differs between members of a species or between paired chromosomes in an individual. Single nucleotide polymorphisms may fall within coding sequences of genes, non-coding regions of genes, or in the intergenic regions between genes. Single nucleotide polymorphisms within a coding sequence will not necessarily change the amino acid sequence of the protein that is produced, due to degeneracy of the genetic code. A Single nucleotide polymorphism in which both forms lead to the same polypeptide sequence is termed synonymous (sometimes called a silent mutation)—if a different polypeptide sequence is produced they are non-synonymous. Single nucleotide polymorphisms that are not in protein-coding regions may still have consequences for gene splicing, transcription factor binding, or the sequence of non-coding RNA.

The term "tissue array" or "tissue microarray", as used herein, refers to high throughput platforms for the rapid analysis of protein, RNA, or DNA molecules. These arrays can be used to validate the clinical relevance of potential biological targets in the development of diagnostics, therapeutics and to study new disease markers and genes. Tissue arrays are suitable for genomics-based diagnostic and drug target discovery.

As used herein, the term "shRNA" or "short hairpin RNA" refers to a sequence of ribonucleotides comprising a single-stranded RNA polymer that makes a tight hairpin turn on itself to provide a "double-stranded" or duplexed region. shRNA can be used to silence gene expression via RNA interference. shRNA hairpin is cleaved into short interfering RNAs (siRNA) by the cellular machinery and then bound to the RNA-induced silencing complex (RISC). It is believed that the complex inhibits RNA as a consequence of the complexed siRNA hybridizing to and cleaving RNAs that match the siRNA that is bound thereto.

As used herein, the term "RNA interference" or "RNAi" refers to the silencing or decreasing of gene expression by siRNAs. It is the process of sequence-specific, post-transcriptional gene silencing in animals and plants, initiated by siRNA that is homologous in its duplex region to the sequence of the silenced gene. The gene may be endogenous or exogenous to the organism, present integrated into a chromosome or present in a transfection vector that is not integrated into the genome. The expression of the gene is either completely or partially inhibited. RNAi inhibits the gene by compromising the function of a target RNA, completely or partially. Both plants and animals mediate RNAi by the RNA-induced silencing complex (RISC); a sequence-specific, multicomponent nuclease that destroys messenger RNAs homologous to the silencing trigger. RISC is known to contain short RNAs (approximately 22 nucleotides) derived from the double-stranded RNA trigger, although the protein components of this activity are unknown. However, the 22-nucleotide RNA sequences are homologous to the target gene that is being suppressed. Thus, the 22-nucleotide sequences appear to serve as guide sequences to instruct a multicomponent nuclease, RISC, to destroy the specific mRNAs. Carthew has reported (Curr. Opin. Cell Biol. 13(2): 244-248 (2001)) that eukaryotes silence gene expression in the presence of dsRNA homologous to the silenced gene. Biochemical reactions that recapitulate this phenomenon generate RNA fragments of 21 to 23 nucleotides from the double-stranded RNA. These stably associate with an RNA endonuclease, and probably serve as a discriminator to select mRNAs. Once selected, mRNAs are cleaved at sites 21 to 23 nucleotides apart.

As used herein, the term "siRNAs" refers to short interfering RNAs. In some embodiments, siRNAs comprise a duplex, or double-stranded region, of about 18-25 nucleotides long; often siRNAs contain from about two to four unpaired nucleotides at the 3' end of each strand. At least one strand of the duplex or double-stranded region of a siRNA is substantially homologous to or substantially complementary to a target RNA molecule. The strand complementary to a target RNA molecule is the "antisense strand"; the strand homologous to the target RNA molecule is the "sense strand", and is also complementary to the siRNA antisense strand. siRNAs may also contain additional sequences; non-limiting examples of such sequences include linking sequences, or loops, as well as stem and other folded structures. siRNAs appear to function as key intermediaries in triggering RNA interference in invertebrates and in vertebrates, and in triggering sequence-specific RNA degradation during posttranscriptional gene silencing in plants.

The term "xenograft", as used herein, refers to the transfer or transplant of a cell(s) or tissue from one species to an unlike species (or genus or family).

The term "orthotopic" or "orthotopic xenograft", as used herein, refers to a cell or tissue transplant grafted into its normal place in the body.

The term "fluorescent activated cell sorting" or "FACS", as used herein, refers to a technique for counting, examining, and sorting microscopic particles suspended in a stream of fluid. It allows simultaneous multiparametric analysis of the physical and/or chemical characteristics of single cells flowing through an optical and/or electronic detection apparatus. Generally, a beam of light (usually laser light) of a single wavelength is directed onto a hydro dynamically focused stream of fluid. A number of detectors are aimed at the point where the stream passes through the light beam; one in line with the light beam (Forward Scatter, correlates to cell volume) and several perpendicular to the beam, (Side Scatter, correlates to the inner complexity of the particle and/or surface roughness) and one or more fluorescent detectors. Each suspended particle passing through the beam scatters the light in some way, and fluorescent chemicals found in the particle or attached to the particle may be excited into emitting light at a lower frequency than the light source. By analyzing the combinations of scattered and fluorescent light picked up by the detectors it is then possible to derive information about the physical and chemical structure of each individual particle.

The term "data mining", as used herein, refers to the automated or convenient extraction of patterns representing knowledge implicitly stored or captured in large databases, data warehouses, internet websites, other massive information repositories, or data streams.

The terms "over-express", "over-expressing" and grammatical equivalents, as used herein, refer to the production of a gene product at levels that exceed production in normal or control cells. The term "over-expression" or "highly expressed" may be specifically used in reference to levels of mRNA to indicate a higher level of expression than that typically observed in a given tissue in a control or non-transgenic animal. Levels of mRNA are measured using any of a number of techniques known to those skilled in the art including, but not limited to Northern blot analysis. Appropriate controls are included on the Northern blot to control for differences in the amount of RNA loaded from each tissue analyzed, the amount of 28S rRNA (an abundant RNA transcript present at essentially the same amount in all tissues) present in each sample can be used as a means of normalizing or standardizing the mRNA-specific signal observed on Northern blots. Over-expression may likewise result in elevated levels of proteins encoded by said mRNAs.

The term "heatmap", as used herein, refers to a graphical representation of data where the values obtained from a variable two-dimensional map are represented as colors. As related to the field of molecular biology, heat maps typically represent the level of expression of multiple genes across a number of comparable samples as obtained from a microarray.

The term "phage display", as used herein, refers to the integration/ligation of numerous genetic sequences from a DNA library, consisting of all coding sequences of a cell, tissue or organism library into the genome of a bacteriophage (i.e. phage) for high-throughput screening protein-protein and/or protein-DNA interactions. Using a multiple cloning site, these fragments are inserted in all three possible reading frames to ensure that the cDNA is translated. DNA fragments are then expressed on the surface of the phage particle as part of it coat protein. The phage gene and insert DNA hybrid is then amplified by transforming bacterial cells (such as TG1 *E. coli* cells), to produce progeny phages that display the relevant protein fragment as part of their outer coat. By immobilizing relevant DNA or protein target(s) to the surface of a well, a phage that displays a protein that binds to one of those targets on its surface will remain while others are removed by washing. Those that remain can be eluted, used to produce more phage (by bacterial infection with helper phage) and so produce an enriched phage mixture. Phage eluted in the final step can be used to infect a suitable bacterial host, from which the phagemids can be collected and the relevant DNA sequence excised and sequenced to identify the relevant, interacting proteins or protein fragments.

The term "apoptosis", as used herein, refers to a form of programmed cell death in multicellular organisms that involves a series of biochemical events that lead to a variety of morphological changes, including blebbing, changes to the cell membrane such as loss of membrane asymmetry and attachment, cell shrinkage, nuclear fragmentation, chromatin condensation, and chromosomal DNA fragmentation. Defective apoptotic processes have been implicated in an extensive variety of diseases; for example, defects in the apoptotic pathway have been implicated in diseases associated with uncontrolled cell proliferations, such as cancer.

The term "bioluminescence imaging" or "BLI", as used herein, refers to the noninvasive study of ongoing biological processes in living organisms (for example laboratory animals) using bioluminescence, the process of light emission in living organisms. Bioluminescence imaging utilizes native light emission from one of several organisms which bioluminescence. The three main sources are the North American firefly, the sea pansy (and related marine organisms), and bacteria like *Photorhabdus luminescens* and *Vibrio fischeri*. The DNA encoding the luminescent protein is incorporated into the laboratory animal either via a virus or by creating a transgenic animal. While the total amount of light emitted via bioluminescence is typically small and not detected by the human eye, an ultra-sensitive CCD camera can image bioluminescence from an external vantage point. Common applications of BLI include in vivo studies of infection (with bioluminescent pathogens), cancer progression (using a bioluminescent cancer cell line), and reconstitution kinetics (using bioluminescent stem cells).

The term "consensus region" or "consensus sequence", as used herein, refers to the conserved sequence motifs that show which nucleotide residues are conserved and which nucleotide residues are variable when comparing multiple DNA, RNA, or amino acid sequence alignments. When comparing the results of a multiple sequence alignment, where related sequences are compared to each other, and similar functional sequence motifs are found. The consensus sequence shows which residues are conserved (are always the same), and which residues are variable. A consensus sequence may be a short sequence of nucleotides, which is found several times in the genome and is thought to play the same role in its different locations. For example, many transcription factors recognize particular consensus sequences in the promoters of the genes they regulate. In the same way restriction enzymes usually have palindromic consensus sequences, usually corresponding to the site where they cut the DNA. Splice sites (sequences immediately surrounding the exon-intron boundaries) can also be considered as consensus sequences. In one aspect, a consensus sequence defines a putative DNA recognition site, obtained for example, by aligning all known examples of a certain recognition site and defined as the idealized sequence that represents the predominant base at each position. Related sites should not differ from the consensus sequence by more than a few substitutions.

The term "linkage", or "genetic linkage," as used herein, refers to the phenomenon that particular genetic loci of genes are inherited jointly. The "linkage strength" refers to the probability of two genetic loci being inherited jointly. As the distance between genetic loci increases, the loci are more likely to be separated during inheritance, and thus linkage strength is weaker.

The term "neighborhood score", as used herein, refers to the relative value assigned to a genomic locus based on a geometry-weighted sum of expression scores of all the genes on a given chromosome, as a measurement of the copy number status of the locus. A positive neighborhood score is indicative of an increase in copy number, whereas a negative neighborhood score is indicative of a decrease in copy number.

The term "expression score", as used herein, refers to the expression differences (i.e., the level of transcription (RNA) or translation (protein)) between comparison groups on a given chromosome. The expression score for a given gene is calculated by correlating the level of expression of said gene with a phenotype in comparison. For example, an expression score may represent a comparison of the expression differences of a given gene in normal vs. abnormal conditions, such as parental vs. drug-resistant cell lines. As used herein, the term "regional expression score" refers to the expression score of gene(s) in proximity to the locus in consideration. Since linkage strength between genetic loci decreases (i.e. decays) as the distance between them increases, the "regional expression score" more accurately reflects the expression differences between comparison groups by assigning greater weight to the expression scores of genes in proximity to the locus in consideration.

The terms "geometry-weighted" or "geometry-weighted sum", as used herein, refers to the significance attached to a given value, for example an "expression score", based on physical position, including but not limited to genomic position. Since linkage strength between genetic loci decreases (i.e. decays) as the distance between them increases, the "weight" assigned to a given value is adjusted accordingly.

The term "copy number alteration" or "CNA", as used herein, refers to the increase (i.e. genomic gain) or decrease (i.e. genomic loss) in the number of copies of a gene at a specific locus of a chromosome as compared to the "normal" or "standard" number of copies of said gene that locus. As used herein, an increase in the number of copies of a given gene at a specific locus may also be referred to as an "amplification" or "genomic amplification" and should not be confused with the use of the term "amplification" as it relates, for example, to amplification of DNA or RNA in PCR and other experimental techniques.

The term "clonogenic assay", as used herein, refers to a technique for studying whether a given cancer therapy (for example drugs or radiation) can reduce the clonogenic survival and proliferation of tumor cells. While any type of cell may be used, human tumor cells are commonly used for ontological research. The term "clonogenic" refers to the fact that these cells are clones of one another.

The term "adjuvant therapy", as used herein, refers to additional treatment given after the primary treatment to increase the chances of a cure. In some instances, adjuvant therapy is administered after surgery where all detectable disease has been removed, but where there remains a statistical risk of relapse due to occult disease. If known disease is left behind following surgery, then further treatment is not technically "adjuvant". Adjuvant therapy may include chemotherapy, radiation therapy, hormone therapy, or biological therapy. For example, radiotherapy or chemotherapy is commonly given as adjuvant treatment after surgery for a breast cancer. Oncologists use statistical evidence to assess the risk of disease relapse before deciding on the specific adjuvant therapy. The aim of adjuvant treatment is to improve disease-specific and overall survival. Because the treatment is essentially for a risk, rather than for provable disease, it is accepted that a proportion of patients who receive adjuvant therapy will already have been cured by their primary surgery. Adjuvant chemotherapy and radiotherapy are often given following surgery for many types of cancer, including colon cancer, lung cancer, pancreatic cancer, breast cancer, prostate cancer, and some gynecological cancers.

The term "matched samples", as used herein, as for example "matched cancer samples" refers to a sample in which individual members of the sample are matched with every other sample by reference to a particular variable or quality other than the variable or quality immediately under investigation. Comparison of dissimilar groups based on specified characteristics is intended to reduce bias and the possible effects of other variables. Matching may be on an individual (matched pairs) or a group-wide basis.

The term "genomic segments", as used herein, refers to any defined part or region of a chromosome, and may contain zero, one or more genes.

The teen "co-administer", as used herein, refers to the administration of two or more agents, drugs, and/or compounds together (i.e. at the same time).

The term "diagnose" or "diagnosis", as used herein, refers to the determination, recognition, or identification of the nature, cause, or manifestation of a condition based on signs, symptoms, and/or laboratory findings.

The term "resistance", as used herein, refers to cancer cells that do not respond to chemotherapy drugs (i.e. chemotherapeutic agents). Typically, a first course of chemotherapy may prove highly beneficial, nearly annihilating a tumor, but a few resistant cancer cells often survive and proliferate. Too often, despite more aggressive second and third courses of chemotherapy, the remaining drug-defiant cells thrive, displaying increasing resistance to drug therapy and eventually displaying virtual invulnerability to chemotherapy. After the drug's effectiveness fades, the patient relapses. This occurs in patients with a variety of blood cancers and solid tumors, including breast, ovarian, lung, and lower gastrointestinal tract cancers. Nature Biotechnology 18:IT18-IT20 (2000). Resistance to treatment with anticancer drugs results from a variety of factors including individual variations in patients and somatic cell genetic differences in tumors, even those from the same tissue of origin. Frequently resistance is intrinsic to the cancer, but as therapy becomes more and more effective, acquired resistance has also become common. The development of multidrug resistance (MDR) to chemotherapy remains a major challenge in the treatment of cancer. Resistance exists against every effective anticancer drug and can develop by numerous mechanisms including decreased drug uptake, increased drug efflux, activation of detoxifying systems, activation of DNA repair mechanisms, and insensitivity to drug-induced apoptosis. Methods Mol. Biol. 596:47-76 (2010).

In some embodiments, the present invention contemplates treating drug resistant cancer cells. It is not intended that the present invention be limited to the degree of resistance, i.e. resistance can be shown simply by the fact that it takes higher doses of drug to kill these cells. The cells need not be resistant at every dose. The cells may be resistant such that higher doses needed to kill the cells will not be well tolerated by the patient.

As used herein, "Doxorubicin" (trade name Doxil) also known as "hydroxydaunorubicin" or "Adriamycin" refers to a drug used in cancer chemotherapy, that is considered to be the most effective agent in the treatment of breast cancer patients. Doxorubicin is an anthracycline antibiotic, closely related to the natural product daunomycin, and like all anthracyclines, works by intercalating DNA, with the most serious adverse effect being life-threatening heart damage. Doxorubicin is commonly used in the treatment of a wide range of cancers, including some leukemia's and Hodgkin's lymphoma, as well as cancers of the bladder, breast, stomach, lung, ovaries, thyroid, soft tissue sarcoma, multiple myeloma. It is frequently used in breast cancer therapy either as single-agent or in combination with other drugs like docetaxel and cyclophosphamide. Unfortunately, resistance to this agent is common, representing a major obstacle to successful treatment. Mol. Cancer. Ther. 5(8):2115-20 (2006). Doxorubicin is administered intravenously, as the hydrochloride salt. It may be sold under the brand names Adriamycin PFS, Adriamycin RDF, or Rubex. Commonly used doxorubicin-containing regimens include, but are not necessarily limited to, AC (Adriamycin, cyclophosphamide), TAC (taxotere, AC), ABVD (Adriamycin, bleomycin, vinblastine, dacarbazine), BEACOPP (bleomycin, etoposide, Adriamycin, cyclophosphamide, vincristine, procarbazine, prednisone), BEP (bleomycin, etoposide, platinum agent (cisplatin (Platinol)), CAF (cyclophosphamide, Adriamycin, fluorouracil (5-FU)), CAV (cyclophosphamide, Adriamycin, vincristine), CHOP (cyclophosphamide, Adriamycin, vincristine, prednisone), ChlVPP/EVA (chlorambucil, vincristine, procarbazine, prednisone, etoposide, vinblastine, Adriamycin), CVAD/Hyper-CVAD (cyclophosphamide, vincristine, Adriamycin, dexamethasone), DT-PACE (dexamethasone, thalidomide, cisplatin or platinol, Adriamycin, cyclophosphamide, etoposide), FAC (5-fluorouracil, Adriamycin, cyclophosphamide), m-BACOD (methotrexate, bleomycin, adriamycin, cyclophosphamide, Oncovin (vincristine), dexamethasone), MACOP-B (methotrexate, leucovorin (folinic acid), adriamycin, cyclophosphamide, Oncovin (vincristine), prednisone, bleomycin), ProMACE-MOPP (methotrexate, Adriamycin, cyclophosphamide, etoposide+MOPP), ProMACE-CytaBOM (prednisone, Adriamycin, cyclophosphamide, etoposide, cytarabine, bleomycin, vincristine, methotrexate, leucovorin), VAD (vincristine, Adriamycin, dexamethasone), Regimen I (vincristine, Adriamycin, etoposide, cyclophosphamide) and VAPEC-B (vincristine, Adriamycin, prednisone, etoposide, cyclophosphamide, bleomycin).

Analogues of Doxorubicin for cancer chemotherapy include, but are not limited to, daunorubicin, 4-demethoxydaunorubicin (idarubicin), pirarubicin (DaunoXome), epirubicin, pegylated liposomal doxorubicin (Lipo-Dox®), antibody-conjugated liposomal doxorubicin (e.g. S5A8-Lipo-Dox), 4'-epidoxorubicin, AD198, N-(5,5-Diacetoxypent-1-yl)doxorubicin, and Doxorubicin analogues 2-5, incorporating the following alkylating or latent alkylating substituents, R, on the 3'-position of the daunosamine sugar. 2, $R=NHCOC_6H_4(p)SO_2F$; 3, $R=NHCOCH_2Br$; 4, $R=NHCOCH_2Cl$; 5, $R=NHCON(NO)CH_2CH_2Cl$. J Med. Chem. 1991 Feb.; 34(2):561-4.

As used herein, "Ibrutinib", also known as PCI-32765, refers to a drug for the treatment of various types of hematopoietic related cancer. However, in one embodiment, the present invention contemplates the use of ibrutinib for non-hematopoietic related cancers, and in particular for breast cancer.

DETAILED DESCRIPTION

Tyrosine kinases (TKs) catalyze the reversible process of tyrosine phosphorylation, a key step in most signal transduction pathways that govern cellular proliferation, survival, differentiation, and motility. Dysregulation of TKs, as occurs through inappropriate expression, activation, or both, is commonly associated with human cancers (Blume-Jensen and Hunter 2001; Giamas, et al. 2010). As a result, TKs, as a class, are the most commonly found dominant oncogenes (Baselga 2006; Blume-Jensen and Hunter 2001; Krause and Van Etten 2005; Vassilev and Uckun 2004). Receptor protein tyrosine kinases (RPTKs) transmit extracellular signals across the plasma membrane to cytosolic proteins, stimulating the formation of complexes that regulate key cellular functions. Over half of the 90 tyrosine kinases have been implicated in human cancers and are for this reason considered highly promising drug targets. To gain insight into the tyrosine kinases that contribute to breast cancer related cellular mechanisms, we carried out a large-scale loss-of-function analysis of the tyrosine kinases, using RNA interference, in the clinically relevant Erb-B2 positive, BT474 breast cancer cell line. The cytosolic, non-receptor tyrosine kinase Bruton's tyrosine kinase (BTK), which has been extensively studied for its role in B cell development, was among those tyrosine kinase genes required for BT474 breast cancer cell survival. The BTK protein identified was an alternative faun containing an amino-terminal extension. This alternative form of the Btk message is also present in tumorigenic breast cells at significantly higher levels than in normal breast cells.

Small molecules that directly inhibit the catalytic activity of tyrosine kinases have been sought as potential cancer chemotherapeutics. Recent successes with a few well-studied tyrosine kinases have proven the value of these proteins as drug targets. Imatinib mesylate (Gleevec) has proven hugely successful in treating CML. The EGFR inhibitors, Gefitinib (Iressa) and erlotinib (Tarceva), are currently used on a variety of solid tumors (Krause and Van Etten 2005; Kris, et al. 2003; Shepard, et al. 2008). Trastuzumab (Herceptin), a humanized monoclonal antibody that specifically inhibits Erb-B2, is widely used in the treatment of breast cancers. Each of these treatments, however, has significant limitations related to tissue spectrum, acquired resistance, and efficacy in advanced disease (Nahta and Esteva 2006). The identification of additional TK genes and pathways that contribute to the survival of distinct cancer cell types, so that they can be effectively targeted, would be of great value.

A large-scale RNAi screen found that nearly ⅓ (30%) of the human TKs screened impeded cellular proliferation by more than half of control levels in an ErbB-2 over-expressing breast cancer cell line. Among these, 54% were receptor TKs and 46% were non-receptor cytoplasmic TKs and with few exceptions, were distinct from those identified as survival kinases in an RNAi screen carried out in HeLa cells (MacKeigan, et al. 2005). This may reflect decreased cellular proliferation or increased cell death in BT474 breast cancer cells. Unexpectedly, four of the five non-receptor tyrosine kinases that exhibited the strongest impact on cellular proliferation were members of the Tec family of cytoplasmic tyrosine kinases. Surprisingly, a novel isoform of a member of the Tec family of non-receptor tyrosine kinases, Bruton's tyrosine kinase (BTK), which is known primarily for its critical role in B cell maturation, is among the TKs that exhibited the strongest impact on cellular proliferation. The expression of this novel BTK isoform is elevated in a number of breast cancer cell lines compared to non-tumorigenic breast cell lines. Further exploration of one Tec family member, Bruton's Tyrosine Kinase, (BTK) revealed that its knockdown using either siRNAs led to an increase in apoptosis. A unique Btk transcript was isolated from BT474 cells, which encodes an additional 34 amino acids in frame with the published BTK start codon, suggesting that an N-terminally elongated form of the BTK protein is present in BT474 breast cancer cells. The expression of this novel Btk transcript is higher in a number of breast cancer cell lines compared to non-tumorigenic breast cell lines. These results suggest that an alternative BTK protein, potentially with other Tec family tyrosine kinases, contribute to breast cancer cell survival.

The validity of the breast screen is supported by the identification of several kinases with known transformative properties. ErbB-2, in particular was expected to be required for BT474 proliferation since it is amplified and constitutively activated in this breast cancer cell line. Other TK's identified in the screen have established roles in breast cancer. FGFR2 is amplified or over-expressed in 5-10% of breast tumors (Adnane, et al. 1991; Cha, et al. 2008; Penault-Llorca, et al. 1995), and has been the focus of several genome-wide association studies covering thousands of unique breast tumors (Hunter, et al. 2007). NTRK2/TRKB is the brain-derived neurotropic factor (BDNF) receptor and is expressed in a subset of high-grade human breast tumors (Cameron and Foster 2008).

The major and largely unexpected discovery of the screen was the identification of a functional role for the cytosolic, non-receptor tyrosine kinase BTK in breast cancer cell survival. BTK is thought to function primarily in cells derived from the hematopoietic cell lineage, where it is crucial for B cell maturation. Although a recent study has indicated that the expression of this kinase is elevated in a subset of basal breast tumors due to the presence of tumor-infiltrative lymphocytes (Sabatier, et al. 2011), our study focused on tumor cells Inhibition of BTK using RNAi or pharmacological inhibitors results in increased apoptosis in BT474 and MCF-7 breast cancer cells (FIGS. 10A, B; FIG. 13B). Importantly, RNAitriggers specific to the alternate isoform, BTK-C, which is expressed in breast cancer cells compromise cell survival; BTK-C over-expression inhibits apoptosis induced by Doxorubicin (FIG. 13D, E), both indicating that at least some of the pro-survival effects of BTK are due to this isoform.

Although no role has previously been described for BTK in epithelial cell cancers, dysregulated BTK expression is associated with the formation and maintenance of leukemias and lymphomas and is currently being targeted therapeutically. BTK over-expression has been implicated in imatinib resistance to chronic myeloid leukemia (CML) and acute lymphoblastic leukemia (ALL) (Villuendas, et al. 2006); (Hofmann, et al. 2002). Its constitutive activation due to deregulated B cell receptor (BCR) engagement contributes to the genesis of B cell lymphomas (Irish, et al. 2006); (Kuppers 2005) and new inhibitors are currently in clinical trials for lymphoid malignancies (Honigberg, et al. 2010; Winer, et al. 2012). It is worth noting that a number of tyrosine kinase genes related to B cell signaling were also identified in the screen as being important for the proliferation or survival of BT474 cells. These include LYN which induces BTK phosphorylation and ABL2 (Lin, et al. 2009) which may regulate BTK (Backesjo, et al. 2002) among others.

The BTK protein expressed in breast cells has an amino-terminal 34 amino acid extension, which we have termed BTK-C. Higher levels of this BTK-C mRNA are found in breast cancer cells compared to non-cancerous breast cells. Early experimentation has not detected functional differences between the BTK-A and BTK-C proteins. It may be that deregulation of an alternative promoter in breast cancer cells causes increased expression of BTK-C and that this provides an essential function for these cells. In this sense, BTK-C is similar to other cancer related genes. Recent work has shown that alternative promoter usage in genes involved in cancer initiation and progression are significantly more likely to have multiple promoters than are non-cancer causing genes (Davuluri, et al. 2008). For example, the aberrant use of an alternative promoter in the TGFf33, LEF1, and CyP19A1 genes have been directly linked to cancer cell growth (Archey, et al. 1999; Harada, et al. 1993; Li, et al. 2006). More recently, the expansion of genomic platforms has led to genome-wide views of promoter usage that have revealed increased alternative promoter usage in tumor cells compared to normal cells (Thorsen, et al. 2011).

At present, the mechanism for BTK supporting breast cancer cell survival is unknown. BTK, like several kinases identified in the screen, has multiple protein-protein/protein-lipid interaction domains, enabling the formation of numerous and diverse signal complexes. This complexity has made its mechanism of action in B cells where it is relatively well studied poorly understood. In breast cells, microarray analysis indicates that BTK may affect transcription of specific targets. Among transcripts more than 2.5 fold upregulated by BTK-C compared to BTK-A were the calcium handling proteins calbindin (CALB1) and troponin (TNNI2) which may suggest a role for this kinase in calcium signaling as occurs in B cells, and STEAP4 which implicates BTK-C in the increased glucose uptake found in a number of breast cancer cells (FIG. 15). In many ways, these findings are similar to recent studies that indicate that other B cell kinases, including Abl (Srinivasan and Plattner 2006) (Srinivasan, et al. 2008), BMX (Dai, et al. 2006; Jiang, et al. 2007) and Syk (Ruschel and Ullrich 2004), have critical functions in solid tumors and not just haematological malignancies. In these cases the mechanisms are incompletely understood and may involve pathways different from those operating in B cells. Further experimentation is necessary for the elucidation of how BTK and the other B cell kinases become integrated in epithelial cell signal transduction pathways.

RNAi knockdown screen of the PTKS in BT474 breast cancer cells. A functional genomic approach was taken to evaluate the contribution of each TK to breast cancer cell viability. An unbiased functional RNAi screen targeting the PTKs in the clinically relevant ErbB-2 positive, BT474 breast cancer cell line was performed to identify additional TKs that when knocked down, sensitized the cells to cell death. 236 short-hairpin RNAs (shRNAs) (Paddison et al., 2004; Silva et al. 2005) were used to target 82 of the 90 PTK genes in the ErbB-2-positive breast cancer cell line BT474, such that, on average, each PTK was targeted with 3 independent shRNA constructs. Each shRNA was co-transfected with a plasmid that directs the expression of GFP so that differences in transfection could be normalized. Effects on cells were monitored using alamarBlue (Biosource), a fluorimetric indicator of both cell proliferation and viability that has proven useful in RNAi screeens (Kourtidis et al., 2007), (FIG. 1). 25 of the 82 genes (30%) when silenced by shRNAs led to a fifty percent or greater decrease in BT474 cellular proliferation compared to control levels, in three replicate experiments using at least two unique shRNAs per gene. EGFR, ERBB2, ABL2, FES, NTRK2 (TRK-B), PTK2B, FGFR2, LYN (V-yes-1), EphA1, and BTK were among the kinases that when knocked down caused the greatest reduction in BT474 cellular proliferation levels (Table 2). The validity of the screen is supported in that many of these PTKs have previously described roles in breast tumors (EGFR, ERBB2, FGFR2, PTK2B, NTRK2/TRK-B, EphA1, ABL2) (Behmoaram, et al. 2008; Brantley-Sieders, et al. 2005; Chan, et al. 2006; Ogawa, et al. 2000; Srinivasan and Plattner 2006). These results support the validity of the screen in identifying kinases that are important for breast cancer cell proliferation or survival. For instance, over-expression of ERBB2 in mammary epithelial cells causes malignant transformation and amplification of ERBB2 in invasive primary breast cancers correlates with reduced patient survival (Baselga_2006_Science). FGFR2 is amplified or over-expressed in 5-10% of breast tumors (Adnane et al., 1991; Cha et al., 2008; Penault-Llorca et al., 1995), and has been the focus of several genome-wide association studies covering thousands of unique breast tumors (Hunter et al., 2007). NTRK2/TRKB is the brain-derived neurotrophic factor (BDNF) receptor that is expressed in a subset of high-grade human breast tumors (Cameron and Foster, 2008).

Btk Silencing Leads to Increased Apoptosis. Bruton's Tyrosine Kinase (BTK) was among those genes whose knockdown caused the most significant reduction in BT474 cellular proliferation (FIG. 1; Table 2). This is surprising since BTK is thought to function primarily in cells derived from the hematopoietic cell lineage (de Weers, et al. 1993; Smith, et al. 1994). Mutations in the human Btk gene cause inherited X-linked agammaglobulinemia which is characterized by a virtual absence of B lymphocytes. This is due to a block between the pro- and pre-B cell stages of B cell maturation (Tsukada et al., 1993); (Lindvall et al., 2005). Btk over-expression has been implicated in imatinib resistance to chronic myeloid leukemia (CML) and acute lymphoblastic leukemia (ALL) (Villuendas et al., 2006); (Hofmann et al., 2002). Its constitutive activation due to deregulated B cell receptor (BCR) engagement is an integral component to certain B cell lymphomas (Irish et al., 2006); (Kuppers, 2005). In B-lineage lymphoid cells, Btk serves a protective role through inhibition of Fas/APO-1 mediated apoptosis (Qiu and Kung, 2000; Vassilev et al., 1999).

We chose to interrogate the role Btk might have in breast cancer cells further since no function had been previously described for it in either normal or malignant breast cellular processes. Quantitative PCR (qPCR) analysis detected the Btk transcript towards the later rounds of cycling (34th of 40 total cycles) indicating that Btk levels in BT474 cells are relatively low. Nevertheless, the Btk transcript could be specifically knocked down 2.2 fold further using siRNAs (data not shown). The initial shRNA screen, utilizing a redox indicator assay, revealed a severe decrease in cellular proliferation after knockdown of Btk in BT474 cells. To determine if reduced proliferation correlated with an increase in apoptosis BT474 cells were transfected with siRNAs targeting Btk and cleaved caspase 3 levels were compared to control cells. BT474 cells that were transfected with the Btk siRNA had an 11 fold increase in apoptotic cells compared to control (FIG. 2A-2C) indicating that the loss of proliferation in Btk silenced BT474 cells is due, at least in part, to increased apoptosis.

Figure 10A:
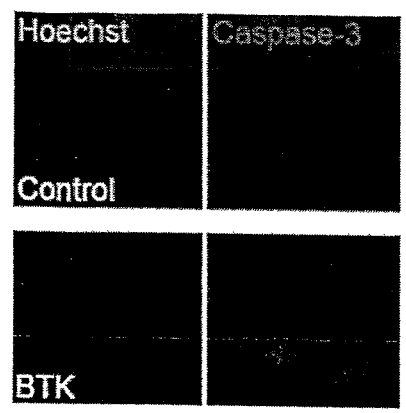
Figure 10B:
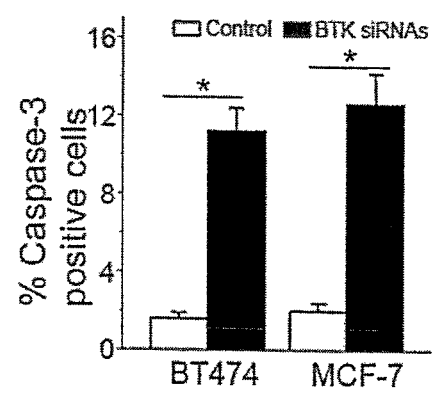

The shRNA screen and additional siRNA silencing experiments reveal a significant decrease in cellular proliferation after knockdown of BTK in BT474 cells (FIG. 1, FIG. 10). Knockdown of BTK in BT474 cells with siGENOME SMART pool duplex siRNAs, which are transfected into these cells more efficiently, leads to widespread cell death. In these cells, BTK transcript levels are specifically knocked down to 37.5% of control at 48 hrs (not shown) prior to the significant loss of cells that occurs between 72 and 96 hours and that is due to increased apoptosis. BT474 cells transfected with siRNAs targeting BTK have an 11-fold increase in apoptotic cells compared to control as evidenced by increased cleaved caspase 3 levels (FIG. 10A, B). Similarly, knockdown of BTK has the same effect increasing levels of apoptosis in MCF-7 cells. This indicates that the decrease in proliferative activity found in BTK-silenced BT474 cells is due, at least in part, to increased apoptosis. Since BTK knockdown with both shRNAs and several siRNAs all result in a similar apoptotic effect, we are confident this result is due to silencing of BTK and is not an off-target effect.

A novel form of the btk message is present in breast cancer cells. Although no function has been previously described for Btk in breast cells, inhibiting Btk using shRNAs severely reduced the proliferation of the BT474 breast cancer cell line compared to control (FIG. 1). The presence of the Btk transcript in BT474 breast cancer cells was confirmed by amplifying the transcript from cDNA. Two distinct Btk specific primer sets were generated by designing primer pairs to unique regions of the Btk gene at nucleotide positions 142 and 2,522, (Btk 5'UTR) and 519 and 2,079, (Btk internal) (Table 1). The Btk internal primer set is specific to sites located between the translational start and stop codons while the Btk 5'UTR forward primer is located 22 bps upstream from the translational start codon, within the 5'UTR, and the downstream primer is located 379 bps downstream from the translational stop codon. Interestingly, while a product of the expected size was amplified from BT474 cDNA using the Btk internal forward primer with either of the reverse primers (FIG. 8 and data not shown), no product was amplified from BT474 cDNA when the Btk 5'UTR forward primer was used with either of the reverse primers (FIG. 8). The 5'UTR primer set did generate a product of the expected size from a positive control cDNA sample generated from Namalwa B-cells (FIG. 8), suggesting that amino-terminal sequence of the Btk transcript in BT474 cells differed from the published sequence.

BT474 breast cancer cells express an alternative form of the btk message from an alternative promoter. To confirm the full length Btk product in BT474 cells, sequence information was obtained upstream from the published Btk start codon using rapid amplification of cDNA ends (5'RACE). A sequence alignment that included the first 395 nucleotides of the published Btk exon 1 sequence (accession # U3399) and the 398 nucleotides obtained using 5' RACE revealed that while the sequences were 100% identical from position 307 downstream, the sequence upstream of position 307 was non-homologous (FIG. 3A).

The Btk sequence obtained from BT474 cells using 5'RACE is 100% identical to two entries in the genome database (Levy et al., 2007) (Griffiths-Jones, 2004) that were derived using an automated analysis for gene prediction program (GNOMON). The sequence is named Btk-cra-C (hereafter referred to as Btk-C) reflecting its status as an automated computational prediction rather than an experimentally verified gene message. In addition, the Btk-C sequence is 100% identical to two sequences in the expressed sequence tag (EST) database. The first of the two EST sequences was obtained from a human pheochromocytoma tissue sample (Yang, Y. et al. 2000, unpublished; accession # AV733045) and the second from a study seeking to identify putative alternative promoters of human genes from human peripheral blood mononuclear cells (PEBLM2), (Kimura et al., 2006).

The unique, first exon present in the Btk-C message is located 4,416 bps to the 3' side of the first exon from the published Btk gene (Btk-cra-A, hereafter referred to as Btk-A) and 255 bps to the 5' side of the ribosomal protein L36a (FIG. 3B, C). Evidence of additional ESTs that are identical to the full-length Btk-C transcript, along with the identification of putative pol II promoter sites (Ref) and transcription factor binding sites including Ets, Ap2, AhR HoxA7 (Matys et al., 2003), strongly suggests that the Btk-C transcript found in BT474 cells is driven by an alternate promoter located 4,416 bps to the 3' side if the published Btk-A promoter. In addition, the first exons of the two transcripts must use different donor sites to yield the mature RNAs (FIG. 3A-3C). Furthermore, translation of the Btk-C nucleotide sequence into amino acids revealed an additional 47 amino acids that when aligned to the BTK-A amino acid sequence is in frame with the BTK-A methionine start codon. Importantly, the additional 47 amino acid stretch present in the Btk-C mRNA from BT474 breast cancer cells contains two additional methionine codons, at nucleotide positions 241-243 and 265-267, respectively (FIG. 3A), creating a putative elongated BTK protein (FIG. 4A). Bioinformatic analyses (ExPASy Proteomics Tools) of the BTK-C additional amino acid sequence for conserved motifs including, cleavage sites, phosphorylation, N-glycosylation, or Nmyristoylation sites did not identify any putative functional roles. Although, neither of the novel translational start sites contains strongly conserved Kozak sequences, a transcription start site prediction program (Down and Hubbard, 2002) identified a putative transcription start site, located within a CpG island, 200 bps upstream from the start of the Btk-C mRNA. Additionally, promoter prediction analyses (Knudsen, 1999) of 2500 nucleotides of the Btk-C sequence, located just upstream from the transcription start site (TSS), has predicted the presence of two putative promoters. The first is located 823 bps upstream from the Btk-C TSS and is predicted to be a highly likely promoter with a score of 1.156 and the second is located 22 nucleotides upstream from the Btk-C TSS and is predicted to be a promoter with marginal likeliness with a score of 0.699. A similar promoter prediction analyses using the 2500 nucleotides located just upstream from the Btk-A TSS has also predicted the presence of two putative promoters, but at greater distances from the TS S and with lower likeliness scores compared to either of the Btk-C predicted promoters. The first predicted Btk-A promoter is located 867 bps upstream from the Btk-A TSS and has a marginal likeliness score of 0.649 and the second is located 388 bps upstream from the Btk-A TSS with a marginal likeliness score of 0.569.

Consistent with the bioinformatic TSS and promoter prediction analyses of the Btk-C message, western blotting of BT474 total lysate using a BTK specific antibody detected a faint 801 kD sized product, the predicted size of the BTK-C protein if it was translated from the first of the two additional start codons (FIG. 4B). The BTK-C protein levels are low, suggesting that transcription from the Btk-C promoter is weak. However, no BTK-A specific sized product was detected in BT474 cell lysate, although it was readily detected in B-cell lysate (FIG. 4B), indicating that expression of the Btk-C transcript is distinct from Btk-A expression.

PCR performed with primers designed to amplify the sequence located between the published Ref seq BTK start and stop codons (BTK internal; Table 1) (FIG. 8 and data not shown), produces a product of the expected size from BT474 cDNA. Quantitative PCR (qPCR) analysis detects the BTK transcript in round 34 of 40 total cycles suggesting that BTK levels in BT474 cells are significantly lower than GAPDH reference transcripts. Interestingly, however, RT-PCR analysis of the full length BTK transcript indicates that the BTK mRNA expressed in BT474 cells is missing a PCR primer binding site in the 5'UTR when compared to that expressed in B-cells. Although internal primer pairs yield products of the expected size, no product is amplified from BT474 cDNA when a forward primer designed to hybridize within the 5' UTR is used (BTK 5'UTR; Table 1) (FIG. 8). This 5' UTR primer does, however, generate a product of the expected size from a positive control cDNA sample generated from Namalwa B-cells (FIG. 8). This result suggests that the N-terminal sequence of the BTK transcript in BT474 breast cancer cells differs from the published sequence deduced from B-cell mRNA. The 5' end of the BTK transcript expressed in BT474 cells was obtained using RACE-PCR and subsequently analyzed by DNA sequencing. When aligned to the 5' end of the published BTK message (BTK-A; accession # U13399) the nucleotide sequence of the transcript isolated from BT474 cells is identical downstream from position 307, however, the sequences upstream from position 307 diverge significantly (FIG. 11A) indicating that the BTK transcript in BT474 cells has an alternative first exon (FIG. 11B).

Since the BTK transcript found in BT474 cells is identical to an automated computationally predicted (GNOMON) sequence named BTK-cra-C, we refer to this isoform as BTK-C and the alternative exon, exon 1C (FIG. 11B, C). This transcript has been predicted in genome databases (Levy, et al. 2007) (Griffiths-Jones 2004) and isolated as an expressed sequence tag (EST) from human pheochromocytoma tissue (Yang, Y. et al. 2000, unpublished; accession # AV733045) and peripheral blood mononuclear cells (Kimura, et al. 2006). The portion of the sequence that is specific to the BTK message expressed in BT474 cells is located on the right arm of the X-chromosome, 4,416 by distal from the start site of exon 1 of the published BTK gene (BTK-A). The 5' end of BTK-C is 255 by from the start site of the ribosomal protein L36a gene which is transcribed in the opposite direction (FIG. 11C). A putative transcription start site exists within a CpG island 200 by upstream from the start of exon 1C (Down and Hubbard 2002). In addition, predicted transcription factor binding sites are also present, including Ets, Ap2, AhR and HoxA7 binding sites (Matys, et al. 2003) (Table 3). Transcription factor binding sites (TFBSs) were predicted for 1000 bps of genomic sequence located proximal to the first nucleotide of the BTK-C transcript. TFBSs were predicted for the BTK-C promoter using high stringency parameters to minimize false positives (Matys et al., 2003). From the left column, gene symbol for each transcription factor (TF), in the location of the predicted TFBS in relation to the most 5'-nucleotide transcribed in the BTK-C mRNA, and the sequence of the predicted TFBS are shown (Table 3). T Capitalization depicts nucleotides that are conserved with consensus TFBS, lower case depicts the adjacent BTK-C promoter sequence. Taken together, these data indicate that expression of the BTK-C transcript in BT474 breast cancer cells is driven by an alternate promoter located upstream from the published BTK-A promoter. The first exons from the BTK-A and BTK-C isoforms utilize different donor sites to splice into a common acceptor site, located within exon 2, to yield the mature BTK-A and BTK-C mRNA isoforms (FIG. 11B).

Due to the additional sequence, the BTK-C message encodes a product that contains an amino-terminal 34 amino acid extension to the BTK-A protein (FIG. 12A). This extension is phylogenetically conserved, since DNA sequence encoding it appears in most mammalian species upstream of the BTK start site in each organism (data not shown). A product consistent with this size is observed on immunoblots as an 80 kD product in cellular lysates from several breast cell lines using a polyclonal antibody raised against the pleckstrin homology domain, residues 2-172, of BTK (BD Transduction Laboratory, 611116). The observed size agrees with the BTK-C predicted size of 79.9 kDa and is larger than the 76.3 kDa BTK-A product which is also detected in the breast lines but at significantly lower levels than in the control NAMA-LWA B cell lysate (FIG. 12B). These results indicate that initiation of translation occurs from the initial methionine codon found in the 5' end of the BTK-C transcript in breast cells. Consistent with this, BTK-A and BTK-C sequences cloned into a retroviral vector containing a CMV promoter and a C-terminal triple flag tag sequence (BTK-A-flag and BTK-C-flag vectors, respectively) produce different sized products. 293FT cells transiently transfected with the BTK-A flag vector yield a 79.5 kDa molecular weight product, which is in agreement with the predicted size of the BTK-A protein containing a triple flag tag (FIG. 17A). When 293FT cells were transiently transfected with the BTK-C flag vector, however, two products are detected of approximately 79 kDa and 83 kDa, respectively (FIG. 12C, FIG. 17A, B). These translation product sizes could result from the BTK-C transcript if translation was initiated from the N-terminal methionine (83 kDa) of BTK-C, as well as the methionine start codon of the BTK-A message which is retained as the 35th codon of BTK-C (79.5 kDa) (FIG. 11B). shRNAs targeting internal exons of the BTK gene effectively silence the BTK gene decreasing protein expression, as would be predicted.

The Btk-C Transcript Encodes an Alternative Protein. To engineer more of the BTK-C protein, the Btk-C sequence beginning with the region corresponding to the new start codon and continuing to the stop codon was cloned into a Hygro-MarxIV over-expression vector (Hannon et al., 1999) containing a triple flag tag sequence (hereafter referred to as the Btk-C-flag vector). For comparison, the Btk-A sequence, beginning with the published start codon and continuing to the stop codon, was also cloned into the triple flag tag Hygro-MarxIV vector (hereafter referred to as the Btk-A-flag vector). 293FT cells were co-transfected with the Btk-A-flag vector or Btk-Cflag vector as well as either the Btk shRNA construct or a control shRNA construct. The 293FT cells containing the over-expressed Btk-A protein alone or with the control shRNA yielded a 79.5 KD molecular weight product; the predicted size of the Btk-A protein containing a triple flag tag (FIG. 4C). The 293FT cells containing the over-expressed Btk-C protein alone or with the control shRNA, however, yielded two products. The smaller product is approximately the predicted molecular weight of the Btk-A protein containing a triple flag tag (79.5 KD) and the larger product is the predicted molecular weight of the Btk-C protein containing a triple flag tag if it were translated from the first of the two novel methionine codons (83 KD) (FIG. 4C). Without intending to limit the invention in any embodiment by any theory as to how the embodiment works, Applicants believe that the most likely explanation for the two Btk-C products is that the first of the two additional methionine codons is being used as a translational start site as well as the original methionine start codon, which contains a good Kozak consensus sequence. Interestingly, data from western blotting, qPCR and 5'RACE (FIG. 4B and data not shown) indicate that only the Btk-C transcript is present in BT474 cells, suggesting that the Btk-A promoter is not active in BT474 cells.

293FT cells stably over-expressing either the BTK-A or BTK-C proteins that were transfected with the shRNA targeting Btk contained significantly less cross reactive protein compared to cells transfected with the control shRNA (FIG. 4C; FIG. 17A). Additionally, the transient transfection of BT474 cells stably over-expressing Btk-C with siRNAs targeting Btk resulted in an approximate 70% decrease in Btk protein compared to control (FIG. 4D; FIG. 17B). That the BTK isoform is important to breast cells was confirmed by designing siRNAs that would specifically target this isoform. As shown in FIG. 12B, siRNAs corresponding to exon 1C reduce BTK-C-flag protein expression in transfected HEK 293T cells. Importantly, these siRNAs also decrease the viability of BT474 cells, indicating that this isoform is important for cell viability. Taken together these results confirm that the Btk shRNA and siRNA are strong and specific effectors of Btk gene silencing and that the expression of this isoform is important for breast cancer cell survival.

To assess BTK activation in BT474 cells the phosphorylation status of tyrosine residue number 223, which becomes auto-phosphorylated after activation, was assessed. BT474 cells stably over-expressing either the Btk-A-flag or Btk-C-flag proteins were subjected to immunoprecipitation using a flag specific antibody and the immunoprecipitates were separated with SDS-PAGE electrophoresis. Blots were probed with an anti-phospho Tyr$^{223}$-Btk antibody or a total Btk antibody (Santa Cruz, E-9) to control for loading. The Btk-A protein was phosphorylated as well as both forms of the Btk-C proteins, indicating the Btk-C protein is activated in BT474 cells (FIG. 5A). Addition of the Btk specific inhibitor LFM-A13 severely impeded phosphorylation of both the Btk-A and Btk-C proteins, indicating that auto-phosphorylation of the elongated Btk-C protein is inhibited to a similar level as Btk-A using the Btk-A specific inhibitor LFM-A13 (FIG. 5A). Consistent with this, inhibiting Btk phosphorylation in BT474 cells using 25 uM LFM-A13 increased apoptosis levels by 8% compared to control, further establishing the protective role that Btk plays in BT474 cell survival (FIG. 5B, C). There was no significant change in growth rate or morphology in BT474 cells stably over-expressing the BTK-A or the BTK-C proteins compared to control cells under either standard conditions or serum-free conditions. Thus, although decreased expression results in apoptosis, Btk over-expression does not confer a growth advantage under these conditions (data not shown).

The specific phosphorylation of the BTK-A protein in addition to both forms of BTK produced from the BTK-C vector, indicate that the BTK-C protein is activated in BT474 cells (FIG. 13A) under standard growth conditions. Auto-phosphorylation of BTK was tested by the addition of the BTK specific inhibitor LFM-A13 which has an IC50 for BTK of 17 µM (Vassilev and Uckun 2004). Treatment with 35 µM LFM-A13 for 48 h significantly impedes phosphorylation of both the BTK-A and BTK-C proteins, indicating that autophosphorylation of the elongated BTK-C protein is inhibited to a similar level as BTK-A under these conditions (FIG. 13A). Consistent with this finding, inhibition of BTK autophosphorylation in BT474 cells using 35 µM LFM-A13 increases apoptosis levels six fold compared to control, further establishing the protective role that BTK plays in BT474 cell survival (FIG. 13B).

Figures 6A, 6B:
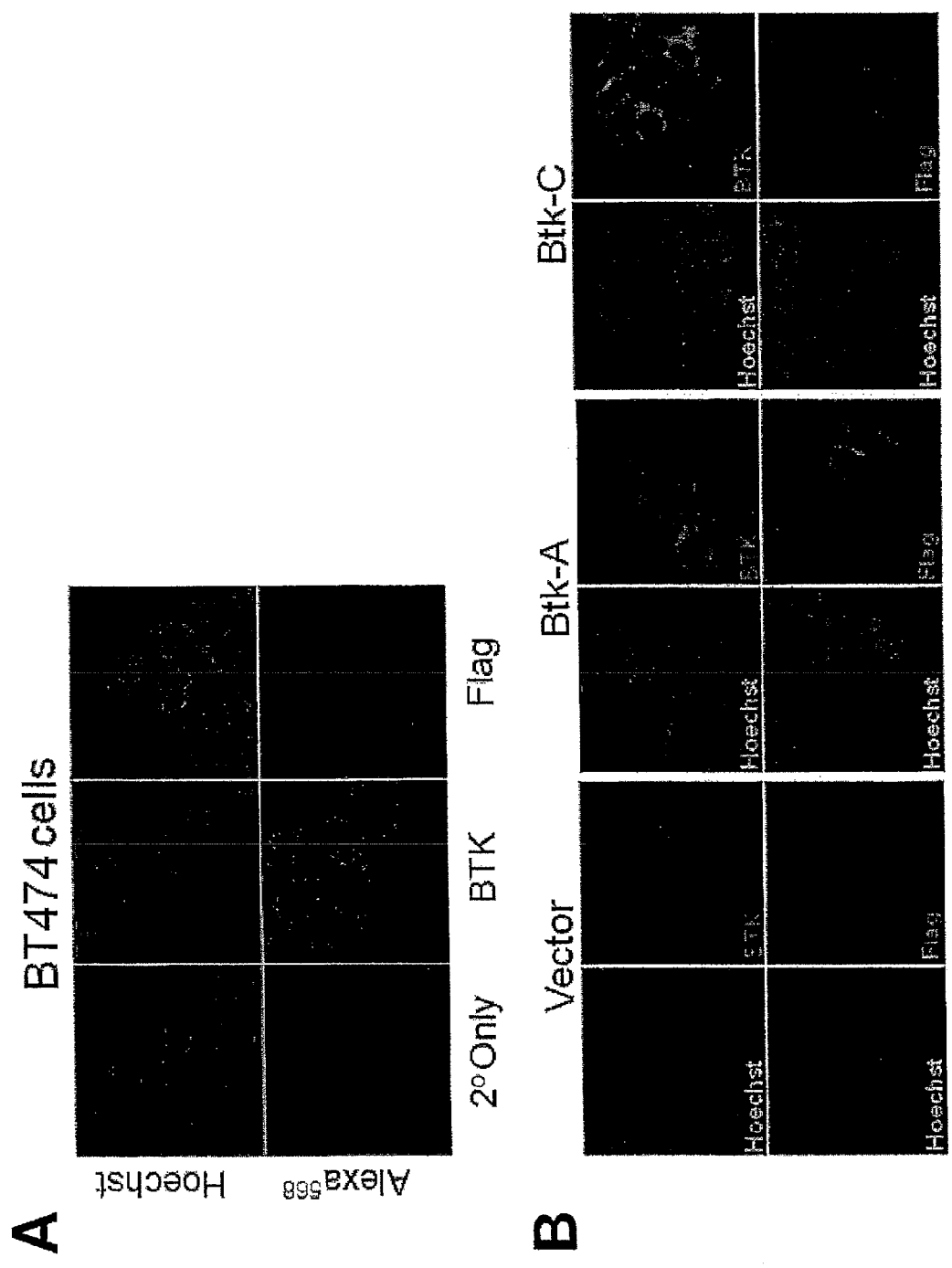

Btk is detected in BT474 cell cytoplasm using immunofluorescence. Immunofluorescent (IF) confocal images were taken of wild type BT474 cells, BT474 cells containing either a stably integrated control Hygro-MarxIV triple flag tag vector (hereafter referred to as control vector), the Btk-A-flag vector or the Btk-C flag vector. As was expected, no BTK specific signal was generated using a flag tag specific antibody in wt BT474 cells or cells stably over-expressing the control vector, but a signal was seen in the cytoplasm of both cell lines stably over-expressing either the BTK-Aflag or the BTK-C-flag proteins (FIG. 6B). However, IF images taken of cells probed with a BTK specific antibody were positive for BTK in the cytoplasm of wtBT474 cells (FIG. 6A) as well as in the cytoplasm of cells stably over-expressing the control vector (FIG. 6B). As would be expected, cells stably over-expressing either the BTK-A or BTK-C proteins contained, noticeably more signal than control cells. The endogenous BTK protein was most likely more visible using immunofluorescent confocal imagery because certain antibodies are more amenable to immunofluorescent confocal imaging protocols compared to SDS-PAGE immunoblotting.

The data from RACE-PCR and RT-PCR (FIG. 11A, FIG. 9) suggest that BTK-C may be preferentially expressed in breast cancer cells compared to non-tumorigenic cells. Immunohistochemical staining of breast tissue microarray samples (Biomax.us BRC-961) shows increased expression of BTK in clinical breast cancer tissues compared to matched, non-tumorigenic, breast tissues using a BTK specific antibody. Significant levels of anti BTK staining are observed in most of the tumor samples (80.2%). Representative images are shown in FIG. 14A. This confirms that at least some form of BTK is unexpectedly expressed in cells of this tissue type, although isoform-specific protein level determination is not currently possible. So that we could discriminate between BTK-A and BTK-C levels in normal and cancer cells, isoform specific qPCR primer sets were designed to the heterogeneous regions of the two sequences located within the 5'UTRs (BTK-A_5'UTR and BTK-C_5'UTR, respectively). cDNA from the BTK-A positive B-cell line Namalwa, the breast cancer cell lines BT474, MCF7, and MDA-MB-361, the non-tumorigenic breast cell line MCF10a and human mammary epithelial cells (HMEC), was independently amplified with each primer set using SYBR Green. A product is detected only for the BTK-A positive malignant B cell line Namalwa using the BTK-A specific primer set (data not shown). However, products are detected in all tested breast samples using the BTK-C specific primer set. Both the BT474 and MCF7 breast cancer cell lines have 4-fold more BTK-C transcript compared to either the non-tumorigenic MCF10a and HMEC breast cells or to the malignant B-cell line Namalwa, while MDA-MB-361 cells had approximately 2 fold more expression compared to MCF10a or HMEC cells (FIG. 14B).

Although BTK-C expression was higher in each of the cancer cell lines tested, isoform-specific expression determinations in tissue sample RNA was more complex. Ten of 23 breast cancer samples had significantly higher expression of BTK-C compared to BTK-A (FIG. 14C). Most of the other breast cancer samples had relatively low levels of both isoforms, with only one tumor sample showing higher levels of BTK-A compared to BTK-C. These results agree with mRNA expression profiling studies performed on clinical breast cancer tissues and made available in the Oncomine database (Oncomine, 2004) In these studies, BTK-A and BTK-C isoforms were not considered independently. In the TCGA data set, the median BTK expression was upregulated 2-fold in invasive breast carcinoma, 1.85 fold in invasive breast ductal carcinomas and 9-fold in invasive lobular breast carcinoma compared to normal breast tissue (The Cancer Genome Atlas, 2011). In a second study, total BTK levels are elevated 6.86 fold (p-value=6.50E-6) in the stroma of invasive ductal cancers (7 samples) compared to all matched, cancer-free, breast tissue samples analyzed (15 samples) (Karnoub, et al. 2007). In another study that profiled the mRNA expression levels of 54 breast cancer samples to 9 non-pathogenic tissue samples, BTK expression was 5.4 fold higher in breast carcinomas (5 samples), 3.2 fold higher in invasive ductal breast carcinoma samples (32 samples), and 4.2 fold higher in invasive lobular breast carcinoma samples (7 samples) compared to non-pathogenic tissue samples (9 samples) (Radvanyi, et al. 2005). Taken together these results indicate that BTK-C expression is enhanced in breast cancer cells compared to non-tumorigenic breast cells, further supporting the notion that expression of the BTK-C transcript, through use of an alternative promoter, contributes to the survival of these cells.

Despite decades of study in hematopoiesis, relatively little is understood about the effectors of BTK. To explore potential mechanisms of BTK-C in breast cell survival, over-expression constructs were used to determine if the BTK-A and BTK-C isoforms are functionally distinct. Assessments of growth rate, morphology, or resistance to apoptotic agents in BT474 cells stably over-expressing either the BTK-A or the BTK-C form proteins, under either standard growth conditions or serum-free conditions reveal no significant differences (data not shown). Furthermore, a bioinformatic analysis (ExPASy Proteomics Tools) of exon 1C to identify conserved motifs, including cleavage sites, phosphorylation, N-glycosylation, or N-myristoylation sites does not identify any putative functional roles.

Since BTK activity has been shown to affect the nuclear localization and activation of a number of transcription factors in hematopoietic cells, we performed microarray analysis of MCF-10A cells over-expressing the BTK-C isoform. In these experiments, BTK-C expression from a retrovirus CMV promoter is increased approximately eightfold compared to vector (data not shown). Microarray analysis of MCF-10A expressing either the BTK-A or BTK-C isoforms indicates that BTK may also affect transcriptional targets in breast cells. In these experiments, expression from a retrovirus CMV promoter of either BTK isoform was increased approximately eightfold more than vector. One gene upregulated in cells over-expressing BTK-C is STEAP4 which participates in a wide range of biologic processes (Gomes, et al. 2012; Grunewald, et al. 2012), such as control of cell proliferation and apoptosis, and glucose uptake (Qin, et al. 2011). Since BTK-C also has similar effects on proliferation and apoptosis resistance, we tested whether BTK-C activity was correlated with glucose uptake by assaying 2-NBDG fluorescence. LFM-A13 inhibits glucose uptake in those breast cancer cell lines that express BTK-C (FIG. 15A, B). Over-expression of BTK-C in MCF-10A cells also results in increased glucose uptake that is inhibited by LFM-A13 (FIG. 15C, D). These results are consistent with the notion that BTK, by altering the expression of STEAP4, has the potential to influence both tumor chemoresistance and energy metabolism, both of which are key features of the cancer cell phenotype.

Btk-C is elevated in breast cancer cells. The data from western blotting, 5'RACE and RT PCR suggested that the Btk-C message might be preferentially expressed in breast cancer cells compared to non-tumorigenic cells. To specifically amplify the Btk-A and Btk-C messages two distinct qPCR primer sets were designed to the unique region of the sequences located within the 5'UTRs, (Btk-A 5'UTR and Btk-C 5'UTR, respectively). cDNA from the Btk-A positive B cell line (Namalwa), the breast cancer cell lines BT474, MCF7, and MDA-MB361, as well as the non-tumorigenic breast cell lines MCF10a and HMEC, was amplified with each primer set using SYBR Green. A product was detected only for the Btk-A positive malignant B cell line Namalwa using the Btk-A specific primer set (data not shown). Products were detected in all breast cancer samples using the Btk-C specific primer set. The non-tumorigenic breast samples produced a signal inconsistently and at the last round of cycling, suggesting the transcript levels were at the limit of detection. Both the BT474 and MCF7 breast cancer cell lines had 4-fold more transcript compared to the either of the non-tumorigenic breast cell lines MCF10a and HMEC and the malignant B-cell line Namalwa (FIG. 7A) These results indicate Btk-C expression is enhanced in breast cancer cells compared to non-tumorigenic breast cells. While not wishing to be bound by any theory of how embodiments of the invention work, this result raises the possibility that mis-expression of the Btk-C transcript, through use of an alternative promoter, may support the unregulated growth characteristic to malignant cells.

A search for Btk expression in clinical breast cancer tissues (Oncomine) revealed that Btk levels are elevated in forty three percent (seven total samples) of invasive ductal cancers compared to all fifteen matched, cancer-free breast tissue samples analyzed (Karnoub et al., 2007). In a second study that profiled the expression levels of 198 breast cancer samples, Btk expression was upregulated in 13% of tissue samples from patients with invasive ductal breast cancer (Desmedt et al., 2007). Although, the Affymetrix probes used to target the Btk gene in these studies does not discriminate between the Btk-A and the Btk-C forms, based upon our data we would predict that the Btk C form is being expressed in these clinical cancer samples. Consistent with the oncomine expression data, using a BTK specific antibody, BTK was detected in a clinical breast cancer tissue sample but not in a matched non-tumorigenic breast tissue sample (FIG. 7B).

Using an unbiased RNAi approach to screen 91% of the human genomes PTKs, we have found that 29% of the total TKs examined strongly contributed to the proliferative potential of the breast cancer cell. Among these TKs, 54% were receptor TK's and 46% were non-receptor cytoplasmic tyrosine kinases As expected, known survival kinases such as EGFR, ERBB2, FGFR2, LYN, PTK2B, NTRK2/TRK-B were identified in the screen. EGFR and ERBB-2 are known critical survival kinases and ErbB-2 is amplified and constitutively activated in the BT474 breast cancer cell line. ERBB2 has no known ligand but rather becomes activated through dimerization with other EGFR family members resulting in constitutive signaling cascades through PLCgamma, PI3K and RAS (FIG. pPLCg2 blot; (Serra et al., 2008); (Eckert et al., 2004).

Additionally, we have revealed previously unrecognized roles for members of the Eph family of receptor tyrosine kinases and Tec family of cytoplasmic tyrosine kinases in promoting breast cancer cell survival in this Erb-B2 positive breast cancer. Four of the 25 TKs that caused the greatest inhibition of BT474 cellular proliferation when knocked down were Eph receptor TKs (FIG. 1; Table 2). Eph receptors and Eph ligands have been well studied for their role in neuronal development (Klein, 2004). Additional functions have been described including involvement in vascular development during embryogenesis, in cell to cell communication and in the regulation of cellular morphogenesis, adhesion and migration (Arvanitis and Davy, 2008); (Merlos-Suarez and Batlle, 2008) (Noren and Pasquale, 2004). Interestingly, Eph Receptors are also expressed on platelets and have been implicated in platelet aggregation at sites of vascular injury (Prevost et al., 2003).

The formation of breast carcinomas is accompanied by the recruitment of a "variety of stromal cells (such as MSCs) with both pro- and anti-tumorigenic activities" (Karnoub et al., 2007); (Bissell and Radisky, 2001). The response is similar to wound healing and scar formation, and involves the continuous deposition of growth factors, cytokines and matrix-remodeling proteins, such that a tumor site is like a 'wound that never heals' (Park et al., 2000). Similarly, both sites of vascular injury and sites of tumor initiation lead to the formation of thrombus; the process by which collagen or thrombin activate freely circulating platelets, leading to their adherence at the injured wall and then to each other, resulting in the formation of a fibril clot (Prevost et al., 2005).

The Eph kinase receptors EphA4 and EphB1 are expressed on platelets (Prevost et al., 2005) and Eph receptor interaction with ligand promotes adhesion and aggregation, at sites of vascular injury, in a Ras family member, Rap1, at least partially, dependent event (Prevost et al., 2005); (Prevost et al., 2004). Furthermore, Eph receptors are known to associate with Src family tyrosine kinases and to signal through cytoplasmic tyrosine kinases (Kullander and Klein, 2002). Following platelet activation EphA4 becomes associated with the Src family cytoplasmic TKs Lyn and Fyn and may promote the phosphorylation of integrin B3 (Prevost et al., 2002). Lyn is another TK integral to B cell receptor signaling and, when knocked down, led to a significant decrease in BT474 cellular proliferation (FIG. 1; Table 2). Without wishing to suggest that embodiments of the invention work according to any particular mechanism or theory, it is interesting that EGF promotes wound healing (Hardwicke et al., 2008), suggesting a potentially cooperative or shared signaling pathway exists for these receptor/ligands (Lo et al., 2006). Further studies will need to be conducted to determine if EGF and/or EGF receptor family members cooperate with the Eph receptors to promote breast cancer cell survival.

In addition, we found that knockdown of four of the five Tec family member kinases resulted in reduced BT474 proliferation (FIG. 1; Table 2). The Tec kinases are known primarily for their roles in immune development and function. Yet, further evaluation of one family member, BTK, led to the discovery of novel protein containing an amino-terminal extension and two additional start codons. A search of the EST database using sequence specific to the Btk-C transcript retrieved two identical EST sequences verifying that this gene is actively transcribed from an alternative promoter five thousand nucleotides downstream from the Btk-A promoter. Applicants will not be bound by any theory of how embodiments of the invention work. However, expression of Btk-C but not Btk-A in a number of breast cancer cells but not in non-tumorigenic cells suggests that deregulation of the promoter is responsible for its expression in the cancer cells. In support of this notion, Btk levels are elevated in several ductal carcinoma tissue samples compared to all normal breast tissue samples analyzed in a study represented in the cancer gene expression database, Oncomine (Karnoub, 2007, Nature). Further experiments will need to be done to determine if the Btk-C variant is in fact the form that is elevated in these breast carcinomas.

A number of recent papers provide data that is consistent with our results implicating hematopoietic associated cytoplasmic TKs in critical functions in solid tumors. ABL2 is a cytoplasmic TK, highly similar to the Src and Tec family of cytoplasmic TKS, whose constitutive activation, generated through chromosomal translocation into breakpoint cluster regions (BCR-Abl) and Tel genes (Tel-Abl), (Advani and Pendergast, 2002) causes various forms of leukemia and myeloproliferative diseases (Tefferi and Gilliland, 2007). Recently, however, Abl has been implicated, for the first time, in breast cancer cell pathogenic processes (Srinivasan and Plattner, 2006). Abl was found to be constitutively active downstream of deregulated ErbB receptors and Src family tyrosine kinases in highly invasive breast cancer cell lines (Srinivasan and Plattner, 2006) (Srinivasan et al., 2008).

In PTEN negative prostate cancer cell lines, LNCaP and PC3, knockdown of the Tec family kinase BMX using siRNAs caused suppression of cell growth. BMX was found to be activated by the ErbB2/ErbB3 receptors and the EGF receptor in a PI3-K dependent and independent manner, respectively. An interaction was identified between BMX and ErbB-3 using immunoprecipitation and immunoblotting. Furthermore, the cytoplasmic tyrosine kinase Src was shown to be responsible for the phosphorylation of BMX prior to membrane recruitment as a Src inhibitor blocked its activation. The authors propose that BMX has a role in integrating the PI3-K and ErbB2/ErbB3 signaling pathways (Jiang et al., 2007). We also noted cell death of BT474 cells after Src knockdown (data not shown), suggesting (without wishing to be bound by theory or hypothesis) that Btk and the other Tec family tyrosine kinases may serve a similar function in ErbB-2 positive breast cancers.

To determine how the RANK and Immune Receptor (ITAMs) signaling pathways converge to promote osteoclast differentiation a genome-wide screen of the non-receptor tyrosine kinases revealed that osteoclasts, but not osteoblasts, express high levels of Btk and Tec. Osteoclasts are derived from bone marrow cells and are under the control of the immune system. The authors conclude (without intending that embodiments of the invention must work according to the hypothesis) that RANKL stimulates the Btk and Tee kinases to form a signaling complex with other molecules, such as the adaptor protein BLNK and the tyrosine kinase Syk, which leads to PLCgamma phosphorylation and the induction of calcium signaling essential for osteoclastogenesis (Shinohara et al., 2008).

Do recruited cell types, such as mesenchymal stem cells, associate with primary tumor cells in such a way to stimulate Btk and other Tec family tyrosine kinases, leading to a convergence of signaling pathways that favor cell survival? Applicants pose this question without admitting in any way that embodiments of the invention work according to the hypothesis implied by the question. In any event, the EGF and BCR signaling complexes and regulated downstream signaling pathways are remarkably similar (Donjerkovic and Scott, 2000); (Lo et al., 2006). Both involve signaling through PLCgamma, PI3K and RAS with the resultant calcium flux and subsequent activation of MAPK/JNK. PLCgamma activation leads to the hydrolysis of PIP2 and the production of DG and IP3. DG induces/phosphorylates PKC leading to the activation of ELK1 and IP3 leads to calcium mobilization. The resulting cellular message is pro-survival. An RNAi screen conducted to identify tyrosine kinases and phosphotases that would sensitize chemoresistant cancer cells to apoptosis found a number of calcium-regulated kinases (CaMK1g, CaMKIINa, CaMKIIB and CaMKIId) to be potent survival kinases (MacKeigan et al., 2005), suggesting that kinases that regulate calcium flux may be important therapeutic targets.

We have previously described a novel isoform of the cytosolic, non-receptor tyrosine kinase, Bruton's tyrosine kinase that is essential for the survival of breast cancer cells. Here we show that we have identified short interfering RNAs that specifically target this isoform and cause the death of breast cancer cells. Since this isoform is preferentially expressed in cancer cells these siRNAs may represent potential therapeutics.

siRNAs that Specifically Target BTK-C.

Previous work is shown that down regulation of BTK with RNAi or inhibition with pharmacological inhibitors causes apoptosis in breast cancer cells. Overexpression gives rise to increased resistance to apoptosis. Our results also show that BTK has increased expression in several breast cancer cell lines and in human breast tumors. The predominant BTK protein found in tumors is an alternative form of the kinase which contains an amino-terminal extension. That a novel isoform of this kinase is expressed and is critical for cell survival indicates that it may represent a potential therapeutic target for the treatment of breast cancer.

That the BTK isoform is important to breast cells was confirmed by designing siRNAs that would specifically target this isoform. BTK-C specific siRNAs were custom synthesized (Dharmacon, Lafayette, CO, USA): siRNA1 sense: GGUUAUUGGAUGCCCAUUAUU (SEQ ID NO: 66), antisense: UAAUGGGCAUCCAAUAACCUU (SEQ ID NO: 67); siRNA2 sense: CAACAAAUGGUUAUUGGAUUU (SEQ ID NO: 68); antisense: AUCCAAUAACCAUUUG-UUGUU (SEQ ID NO: 69). As shown in the figure, siRNAs corresponding to exon 1 C reduce BTK-C-flag protein expression in transfected HEK 293 T cells. Importantly, these siRNAs also decrease the viability of BT474 cells, indicating that this isoform is important for cell viability (FIG. 12D).

BTK-C Inhibits Apoptosis Induced by Doxorubicin in Breast Cancer Cells.

BTK over-expression has been implicated in imatinib resistance to chronic myeloid leukemia (CML) and acute lymphoblastic leukemia (ALL) (Villuendas, et al. 2006); (Hofmann, et al. 2002). Its constitutive activation due to deregulated B cell receptor (BCR) engagement is an integral component to certain B cell lymphomas (Irish, et al. 2006); (Kuppers 2005) and it has been shown to serve a protective role through inhibition of Fas/APO-1 mediated apoptosis (Qiu and Kung 2000; Vassilev, et al. 1999). For this reason we determined whether BTK-C inhibits apoptosis induced by Doxorubicin in breast cancer cells. The BTK-C isoform is expressed at relatively low levels in MCF-10A cells (FIG. 13C, 14B). Over-expression of BTK-C in MCF-10A cells using Flag-tagged MCF-10-vector (10A-Vec) or MCF-10A-Btk-C (10A-Btk-C) constructs reveals that BTK-C counteracts the effects of doxorubicin. The number of apoptotic cells after doxorubicin treatment decreases nearly threefold in cells over-expressing BTK-C as assayed by cleaved caspase-3 signal (FIG. 13D, E). Treatment of MCF-10A cells over-expressing BTK-C with 35 µM LFM-A13 for 24 abolishes the acquired resistance to Doxorubicin (1 µM). These results suggest that BTK expression in tumor cells may lead to chemotherapeutic resistance.

REFERENCES

Adnane, J., Gaudray, P., Dionne, C. A., Crumley, G., Jaye, M., Schlessinger, J., Jeanteur, P., Birnbaum, D. and Theillet, C. (1991) BEK and FLG, two receptors to members of the FGF family, are amplified in subsets of human breast cancers. Oncogene, 6, 659-663.

Advani, A. S, and Pendergast, A. M. (2002) Bcr-Abl variants: biological and clinical aspects. Leuk Res, 26, 713-720.

Archey W B, Sweet M P, Alig G C, Arrick B A. 1999. Methylation of CpGs as a determinant of transcriptional activation at alternative promoters for transforming growth factorbeta3. Cancer Res 59(10):2292-2296.

Arvanitis, D. and Davy, A. (2008) Eph/ephrin signaling: networks. Genes Dev, 22, 416-429. Bissell, M. J. and Radisky, D. (2001) Putting tumours in context. Nat Rev Cancer, 1, 46-54. Blume-Jensen, P. and Hunter, T. (2001) Oncogenic kinase signalling. Nature, 411, 355-365.

Backesjo C M, Vargas L, Superti-Furga G, Smith C I. 2002. Phosphorylation of Bruton's tyrosine kinase by c-Abl. Biochem Biophys Res Commun 299(3):510-515.

Baselga J. 2006. Targeting tyrosine kinases in cancer: the second wave. Science 312(5777):1175-1178.

Behmoaram E, Bijian K, Jie S, Xu Y, Darnel A, Bismar T A, Alaoui-Jamali M A. 2008. Focal adhesion kinase-related proline-rich tyrosine kinase 2 and focal adhesion kinase are co-overexpressed in early-stage and invasive ErbB-2-positive breast cancer and cooperate for breast cancer cell tumorigenesis and invasiveness. Am J Pathol 173(5):1540-1550.

Blume-Jensen P, Hunter T. 2001. Oncogenic kinase signalling. Nature 411(6835):355-365.

Brantley-Sieders, D. M., Fang, W. B., Hicks, D. J., Zhuang, G., Shyr, Y. and Chen, J. (2005) Impaired tumor microenvironment in EphA2-deficient mice inhibits tumor angiogenesis and metastatic progression. Faseb J, 19, 1884-1886.

Call, J. A., Eckhardt, S. G. and Camidge, D. R. (2008) Targeted manipulation of apoptosis in cancer treatment. Lancet Oncol.

Cameron, H. L. and Foster, W. G. (2008) Dieldrin promotes resistance to anoikis in breast cancer cells in vitro. Reprod Toxicol, 25, 256-262.

Cha, J. Y., Lambert, Q. T., Reuther, G. W. and Der, C. J. (2008) Involvement of fibroblast growth factor receptor 2 isoform switching in mammary oncogenesis. Mol Cancer Res, 6, 435-445.

Chan S K, Hill M E, Gullick W J. 2006. The role of the epidermal growth factor receptor in breast cancer. J Mammary Gland Biol Neoplasia 11(1):3-11.

Dai B, Kim O, Xie Y, Guo Z, Xu K, Wang B, Kong X, Melamed J, Chen H, Bieberich C J, Borowsky A D, Kung H J, Wei G, Ostrowski M C, Brodie A, Qiu Y. 2006. Tyrosine kinase Etk/BMX is up-regulated in human prostate cancer and its overexpression induces prostate intraepithelial neoplasia in mouse. Cancer Res 66(16): 8058-8064.

Davuluri R V, Suzuki Y, Sugano S, Plass C, Huang T H. 2008. The functional consequences of alternative promoter use in mammalian genomes. Trends Genet. 24(4):167-177.

Desmedt, C., Piette, F., Loi, S., Wang, Y., Lallemand, F., Haibe-Kains, B., Viale, G., Delorenzi, M., Zhang, Y., d'Assignies, M. S., Bergh, J., Lidereau, R., Ellis, P., Harris, A. L., Klijn, J. G., Foekens, J. A., Cardoso, F., Piccart, M. J., Buyse, M. and Sotiriou, C. (2007) Strong time dependence of the 76 gene prognostic signature for node-negative breast cancer patients in the TRANSBIG multicenter independent validation series. Clin Cancer Res, 13, 3207-3214.

de Weers M, Verschuren M C, Kraakman M E, Mensink R G, Schuurman R K, van Dongen J J, Hendriks R W. 1993. The Bruton's tyrosine kinase gene is expressed throughout B cell differentiation, from early precursor B cell stages preceding immunoglobulin gene rearrangement up to mature B cell stages. Eur J Immunol 23(12):3109-3114.

Donjerkovic, D. and Scott, D. W. (2000) Activation-induced cell death in B lymphocytes. Cell Res, 10, 179-192.

Down, T. A. and Hubbard, T. J. (2002) Computational detection and location of transcription start sites in mammalian genomic DNA. Genome Res, 12, 458-461.

Eckert, L. B., Repasky, G. A., Ulku, A. S., McFall, A., Zhou, H., Sartor, C. I. and Der, C. J. (2004) Involvement of Ras activation in human breast cancer cell signaling, invasion, and anoikis. Cancer Res, 64, 4585-4592.

Giamas G, Man Y L, Hirner H, Bischof J, Kramer K, Khan K, Ahmed S S, Stebbing J, Knippschild U. 2010. Kinases as targets in the treatment of solid tumors. Cell Signal 22(7): 984-1002.

Gomes I M, Maia C J, Santos C R. 2012. STEAP proteins: from structure to applications in cancer therapy. Mol Cancer Res 10(5):573-587.

Griffiths-Jones, S. (2004) The microRNA Registry. Nucleic Acids Res, 32, D109-111.

Grunewald T G, Bach H, Cossarizza A, Matsumoto I. 2012. The STEAP protein family: Versatile oxidoreductases and targets for cancer immunotherapy with overlapping and distinct cellular functions. Biol Cell.

Hannon, G. J., Sun, P., Carnero, A., Xie, L. Y., Maestro, R., Conklin, D. S, and Beach, D. (1999) MaRX: an approach to genetics in mammalian cells. Science, 283, 1129-1130.

Harada N, Utsumi T, Takagi Y. 1993. Tissue-specific expression of the human aromatase cytochrome P-450 gene by alternative use of multiple exons 1 and promoters, and switching of tissue-specific exons 1 in carcinogenesis. Proc Natl Acad Sci USA 90(23):11312-11316.

Hardwicke, J., Schmaljohann, D., Boyce, D. and Thomas, D. (2008) Epidermal growth factor therapy and wound healing—past, present and future perspectives. Surgeon, 6, 172-177.

Hofmann, W. K., de Vos, S., Elashoff, D., Gschaidmeier, H., Hoelzer, D., Koeffler, H. P. and Ottmann, O. G. (2002) Relation between resistance of Philadelphia-chromosome-positive acute lymphoblastic leukaemia to the tyrosine kinase inhibitor STI571 and gene-expression profiles: a gene-expression study. Lancet, 359, 481-486.

Honigberg L A, Smith A M, Sirisawad M, Verner E, Loury D, Chang B, Li S, Pan Z, Thamm D H, Miller R A, Buggy J J. 2010. The Bruton tyrosine kinase inhibitor PCI-32765 blocks B-cell activation and is efficacious in models of autoimmune disease and B-cell malignancy. Proc Natl Acad Sci USA 107(29):13075-13080.

Hunter, D. J., Kraft, P., Jacobs, K. B., Cox, D. G., Yeager, M., Hankinson, S. E., Wacholder, S., Wang, Z., Welch, R., Hutchinson, A., Wang, J., Yu, K., Chatterjee, N., On, N., Willett, W. C., Colditz, G. A., Ziegler, R. G., Berg, C. D., Buys, S. S., McCarty, C. A., Feigelson, H. S., Calle, E. E., Thun, M. J., Hayes, R. B., Tucker, M., Gerhard, D. S., Fraumeni, J. F., Jr., Hoover, R. N., Thomas, G. and Chanock, S. J. (2007) A genome-wide association study identifies alleles in FGFR2 associated with risk of sporadic postmenopausal breast cancer. Nat Genet, 39, 870-874.

Irish, J. M., Czerwinski, D. K., Nolan, G. P. and Levy, R. (2006) Altered B-cell receptor signaling kinetics distinguish human follicular lymphoma B cells from tumor-infiltrating nonmalignant B cells. Blood, 108, 3135-3142.

Jiang, X., Borgesi, R. A., McKnight, N. C., Kaur, R., Carpenter, C. L. and Balk, S. P. (2007) Activation of nonreceptor tyrosine kinase Bmx/Etk mediated by phosphoinositide 3-kinase, epidermal growth factor receptor, and ErbB3 in prostate cancer cells. J Biol Chem, 282, 32689-32698.

Karnoub, A. E., Dash, A. B., Vo, A. P., Sullivan, A., Brooks, M. W., Bell, G. W., Richardson, A. L., Polyak, K., Tubo, R. and Weinberg, R. A. (2007) Mesenchymal stem cells within tumour stroma promote breast cancer metastasis. Nature, 449, 557-563.

Kimura, K., Wakamatsu, A., Suzuki, Y., Ota, T., Nishikawa, T., Yamashita, R., Yamamoto, J., Sekine, M., Tsuritani, K., Wakaguri, H., Ishii, S., Sugiyama, T., Saito, K., Isono, Y., Irie, R., Kushida, N., Yoneyama, T., Otsuka, R., Kanda, K., Yokoi, T., Kondo, H., Wagatsuma, M., Murakawa, K., Ishida, S., Ishibashi, T., Takahashi-Fujii, A., Tanase, T., Nagai, K., Kikuchi, H., Nakai, K., Isogai, T. and Sugano, S. (2006) Diversification of transcriptional modulation: large-scale identification and characterization of putative alternative promoters of human genes. Genome Res, 16, 55-65.

Klein, R. (2004) Eph/ephrin signaling in morphogenesis, neural development and plasticity. Curr Opin Cell Biol, 16, 580-589.

Knudsen, S. (1999) Promoter2.0: for the recognition of PolII promoter sequences. Bioinformatics, 15, 356-361.

Kourtidis, A., Eifert, C. and Conklin, D. S. (2007) RNAi applications in target validation. Ernst Schering Res Found Workshop, 1-21.

Krause D S, Van Etten R A. 2005. Tyrosine kinases as targets for cancer therapy. N Engl J Med 353(2):172-187.

Kris M G, Natale R B, Herbst R S, Lynch T J, Jr., Prager D, Belani C P, Schiller J H, Kelly K, Spiridonidis H, Sandler A, Albain K S, Cella D, Wolf M K, Averbuch S D, Ochs J J, Kay A C. 2003. Efficacy of gefitinib, an inhibitor of the epidermal growth factor receptor tyrosine kinase, in symptomatic patients with non-small cell lung cancer: a randomized trial. Jama 290(16):2149-2158.

Kullander, K. and Klein, R. (2002) Mechanisms and functions of Eph and ephrin signalling. Nat Rev Mol Cell Biol, 3, 475-486.

Kuppers, R. (2005) Mechanisms of B-cell lymphoma pathogenesis. Nat Rev Cancer, 5, 251-262.

Levy, S., Sutton, G., Ng, P. C., Feuk, L., Halpern, A. L., Walenz, B. P., Axelrod, N., Huang, J., Kirkness, E. F., Denisov, G., Lin, Y., MacDonald, J. R., Pang, A. W., Shago, M., Stockwell, T. B., Tsiamouri, A., Bafna, V., Bansal, V., Kravitz, S. A., Busam, D. A., Beeson, K. Y., McIntosh, T. C., Remington, K. A., Abril, J. F., Gill, J., Boiman, J., Rogers, Y. H., Frazier, M. E., Scherer, S. W., Strausberg, R. L. and Venter, J. C. (2007) The diploid genome sequence of an individual human. PLoS Biol, 5, e254.

Li T W, Ting J H, Yokoyama N N, Bernstein A, van de Wetering M, Waterman M L. 2006. Wnt activation and alternative promoter repression of LEF1 in colon cancer. Mol Cell Biol 26(14):5284-5299.

Lin L, Czerwinski R, Kelleher K, Siegel M M, Wu P, Kriz R, Aulabaugh A, Stahl M. 2009. Activation loop phosphorylation modulates Bruton's tyrosine kinase (Btk) kinase domain activity. Biochemistry 48(9):2021-2032.

Lindvall, J. M., Blomberg, K. E., Valiaho, J., Vargas, L., Heinonen, J. E., Berglof, A., Mohamed, A. J., Nore, B. F., Vihinen, M. and Smith, C. I. (2005) Bruton's tyrosine kinase: cell biology, sequence conservation, mutation spectrum, siRNA modifications, and expression profiling 30 Immunol Rev, 203, 200-215.

Lo, H. W., Hsu, S. C. and Hung, M. C. (2006) EGFR signaling pathway in breast cancers: from traditional signal transduction to direct nuclear translocalization. Breast Cancer Res Treat, 95, 211-218.

Lu, J. and Chu, D. (2008) Novel Therapies in Breast Cancer: What is New from ASCO 2008. Hematol Oncol, 1, 16.

MacKeigan, J. P., Murphy, L. O. and Blenis, J. (2005) Sensitized RNAi screen of human kinases and phosphatases identifies new regulators of apoptosis and chemoresistance. Nat Cell Biol, 7, 591-600.

Matys, V., Fricke, E., Geffers, R., Gossling, E., Haubrock, M., Hehl, R., Hornischer, K., Karas, D., Kel, A. E., Kel-Margoulis, O. V., Kloos, D. U., Land, S., Lewicki-Potapov, B., Michael, H., Munch, R., Reuter, I., Rotert, S., Saxel, H., Scheer, M., Thiele, S, and Wingender, E. (2003) TRANSFAC: transcriptional regulation, from patterns to profiles. Nucleic Acids Res, 31, 374 378.

Merlos-Suarez, A. and Baffle, E. (2008) Eph-ephrin signalling in adult tissues and cancer. Curr Opin Cell Biol, 20, 194-200.

Mohamed A J, Yu L, Backesjo C M, Vargas L, Faryal R, Aints A, Christensson B, Berglof A, Vihinen M, Nore B F, Smith C I. 2009. Bruton's tyrosine kinase (Btk): function, regulation, and transformation with special emphasis on the PH domain. Immunol Rev 228(1):58-73.

Nahta, R. and Esteva, F. J. (2006) HER2 therapy: molecular mechanisms of trastuzumab resistance. Breast Cancer Res, 8, 215.

Noren, N. K. and Pasquale, E. B. (2004) Eph receptor-ephrin bidirectional signals that target Ras and Rho proteins. Cell Signal, 16, 655-666.

Ogawa, K., Pasqualini, R., Lindberg, R. A., Kain, R., Freeman, A. L. and Pasquale, E. B. (2000) The ephrinA1 ligand and its receptor, EphA2, are expressed during tumor neovascularization. Oncogene, 19, 6043-6052.

Paddison, P. J., Silva, J. M., Conklin, D. S., Schlabach, M., Li, M., Aruleba, S., Balija, V., O'Shaughnessy, A., Gnoj, L., Scobie, K., Chang, K., Westbrook, T., Cleary, M., Sachidanandam, R., McCombie, W. R., Elledge, S. J. and Hannon, G. J. (2004) A resource for large-scale RNA-interference-based screens in mammals. Nature, 428, 427-431.

Park, C. C., Bissell, M. J. and Barcellos-Hoff, M. H. (2000) The influence of the microenvironment on the malignant phenotype. Mol Med Today, 6, 324-329.

Penault-Llorca, F., Bertucci, F., Adelaide, J., Parc, P., Coulier, F., Jacquemier, J., Birnbaum, D. and deLapeyriere, 0. (1995) Expression of FGF and FGF receptor genes in human breast cancer. Int J Cancer, 61, 170-176.

Prevost, N., Woulfe, D., Tanaka, T. and Brass, L. F. (2002) Interactions between Eph kinases and ephrins provide a mechanism to support platelet aggregation once cell-to-cell contact has occurred. Proc Natl Acad Sci USA, 99, 9219-9224.

Prevost, N., Woulfe, D., Tognolini, M. and Brass, L. F. (2003) Contact-dependent signaling during the late events of platelet activation. J Thromb Haemost, 1, 1613-1627.

Prevost, N., Woulfe, D. S., Jiang, H., Stalker, T. J., Marchese, P., Ruggeri, Z. M. and Brass, L. F. (2005) Eph kinases and ephrins support thrombus growth and stability by regulating integrin outside-in signaling in platelets. Proc Natl Acad Sci USA, 102, 9820-9825.

Prevost, N., Woulfe, D. S., Tognolini, M., Tanaka, T., Jian, W., Fortna, R. R., Jiang, H. and Brass, L. F. (2004) Signaling by ephrinB1 and Eph kinases in platelets promotes Rap1 activation, platelet adhesion, and aggregation via effector pathways that do not require phosphorylation of ephrinB1. Blood, 103, 1348-1355.

Qin D N, Zhu J G, Ji C B, Chunmei S, Kou C Z, Zhu G Z, Zhang C M, Wang Y P, Ni Y H, Guo X R. 2011. Monoclonal antibody to six transmembrane epithelial antigen of prostate-4 influences insulin sensitivity by attenuating phosphorylation of PI3K (P85) and Akt: possible mitochondrial mechanism. J Bioenerg Biomembr 43(3):247-255.

Qiu, Y. and Kung, H. J. (2000) Signaling network of the Btk family kinases. Oncogene, 19, 5651-5661.

Radvanyi L, Singh-Sandhu D, Gallichan S, Lovitt C, Pedyczak A, Mallo G, Gish K, Kwok K, Hanna W, Zubovits J, Armes J, Venter D, Hakimi J, Shortreed J, Donovan M, Parrington M, Dunn P, Oomen R, Tartaglia J, Berinstein N L. 2005. The gene associated with trichorhinophalangeal syndrome in humans is overexpressed in breast cancer. Proc Natl Acad Sci USA 102(31):11005-11010.

Ruschel A, Ullrich A. 2004. Protein tyrosine kinase Syk modulates EGFR signalling in human mammary epithelial cells. Cell Signal 16(11):1249-1261.

Sabatier R, Finetti P, Mamessier E, Raynaud S, Cervera N, Lambaudie E, Jacquemier J, Viens P, Birnbaum D, Bertucci F. 2011. Kinome expression profiling and prognosis of basal breast cancers. Mol Cancer 10:86.

Sabbah, M., Emami, S., Redeuilh, G., Julien, S., Prevost, G., Zimber, A., Ouelaa, R., Bracke, M., De Weyer, 0. and Gespach, C. (2008) Molecular signature and therapeutic perspective of the epithelial-to-mesenchymal transitions in epithelial cancers. Drug Resist Updat.

Serra, V., Markman, B., Scaltriti, M., Eichhorn, P. J., Valero, V., Guzman, M., Botero, M. L., Llonch, E., Atzori, F., Di Cosimo, S., Maira, M., Garcia-Echeverria, C., Parra, J. L., Arribas, J. and Baselga, J. (2008) NVP-BEZ235, a dual PI3K/mTOR inhibitor, prevents PI3K signaling and inhibits the growth of cancer cells with activating PI3K mutations. Cancer Res, 68, 8022-8030.

Shepard H M, Brdlik C M, Schreiber H. 2008. Signal integration: a framework for understanding the efficacy of therapeutics targeting the human EGFR family. J Clin Invest 118(11):3574-3581.

Shinohara, M., Koga, T., Okamoto, K., Sakaguchi, S., Arai, K., Yasuda, H., Takai, T., Kodama, T., Mono, T., Geha, R. S., Kitamura, D., Kurosaki, T., Ellmeier, W. and Takayanagi, H. (2008) Tyrosine kinases Btk and Tec regulate osteoclast differentiation by linking RANK and ITAM signals. Cell, 132, 794-806.

Silva J M, Li M Z, Chang K, Ge W, Golding M C, Rickles R J, Siolas D, Hu G, Paddison P J, Schlabach M R, Sheth N, Bradshaw J, Burchard J, Kulkarni A, Cavet G, Sachidanandam R, McCombie W R, Cleary M A, Elledge S J, Hannon G J. 2005. Second-generation shRNA libraries covering the mouse and human genomes. Nat Genet. 37(11):1281-1288.

Smith C I, Baskin B, Humire-Greiff P, Zhou J N, Olsson P G, Maniar H S, Kjellen P, Lambris J D, Christensson B, Hammarstrom L, et al. 1994. Expression of Bruton's agammaglobulinemia tyrosine kinase gene, BTK, is selectively down-regulated in T lymphocytes and plasma cells. J Immunol 152(2):557-565.

Srinivasan, D. and Plattner, R. (2006) Activation of Abl tyrosine kinases promotes invasion of aggressive breast cancer cells. Cancer Res, 66, 5648-5655.

Srinivasan, D., Sims, J. T. and Plattner, R. (2008) Aggressive breast cancer cells are dependent on activated Abl kinases for proliferation, anchorage-independent growth and survival. Oncogene, 27, 1095-1105.

Tefferi, A. and Gilliland, D. G. (2007) Oncogenes in myeloproliferative disorders. Cell Cycle, 6, 550-566.

Thorsen K, Schepeler T, Oster B, Rasmussen M H, Vang S, Wang K, Hansen K Q, Lamy P, Pedersen J S, Eller A, Mansilla F, Laurila K, Wiuf C, Laurberg S, Dyrskjot L, Orntoft T F, Andersen C L. 2011. Tumor-specific usage of alternative transcription start sites in colorectal cancer identified by genome-wide exon array analysis. BMC Genomics 12:505.

Tsukada, S., Saffron, D. C., Rawlings, D. J., Parolini, 0., Allen, R. C., Klisak, I., Sparkes, R. S., Kubagawa, H., Mohandas, T., Quan, S, and et al. (1993) Deficient expression of a B cell cytoplasmic tyrosine kinase in human X-linked agammaglobulinemia. Cell, 72, 279-290.

Vassilev, A., Ozer, Z., Navara, C., Mahajan, S, and Uckun, F. M. (1999) Bruton's tyrosine kinase as an inhibitor of the Fas/CD95 death-inducing signaling complex. J Biol Chem, 274, 1646 1656.

Vassilev A O, Uckun F M. 2004. Therapeutic potential of inhibiting Bruton's tyrosine kinase, (BTK). Curr Pharm Des 10(15):1757-1766.

Villuendas, R., Steegmann, J. L., Pollan, M., Tracey, L., Granda, A., Fernandez-Ruiz, E., Casado, L. F., Martinez, J., Martinez, P., Lombardia, L., Villalon, L., Odriozola, J. and Piris, M. A. (2006) Identification of genes involved in imatinib resistance in CML: a gene-expression profiling approach. Leukemia, 20, 1047-1054.

Winer E S, Ingham R R, Castillo J J. 2012. PCI-32765: a novel Bruton's tyrosine kinase inhibitor for the treatment of lymphoid malignancies. Expert Opin Investig Drugs 21(3):355-361.

EXPERIMENTAL

Cell culture. Breast cancer cell lines NAMALWA, BT474, MCF-7, SK-BR-3, MDA-MB-361 and MCF10a were obtained from the ATCC. The Burkitt's Lymphoma cell line NAMALWA was obtained from ATCC. Human mammary epithelial cells (HMEC) were obtained from Cambrex. HEK 293FT cells were obtained from Invitrogen. BT474, MCF-7 and HEK 293FT cells were cultured in DMEM (Hyclone) supplemented with 10% FBS (Hyclone) and 100 U/µl of penicillin-streptomycin (Cellgro). NAMALWA were cultured in RPMI-1640 medium (ATCC) supplemented with 10% FBS (Hyclone) and 100 U/µl of penicillin-streptomycin. MDA-MB-361 were cultured in RPMI-1640 medium (ATCC) supplemented with 20% FBS and 100 U/0 of penicillin-streptomycin. HMECs were cultured in MEGM medium (Cambrex). MCF10a were cultured in DME/F12 1:1 medium supplemented with 5% Horse serum, 20 ng/ml EGF, 0.5 µg/ml hydrocortisone, 100 ng/ml cholera toxin, 10 µg/ml insulin, and 100 U/µl of penicillin-streptomycin.

Reagents. The polyclonal anti-BTK antibody (C-20), the monoclonal anti-BTK antibody (E-9) and the polyclonal anti-GAPDH antibody (V-18) were obtained from Santa Cruz Biotechnology (Santa Cruz, Calif., USA). The polyclonal anti-BTK antibody used for immunofluorescence was obtained from ProSci Incorporated (Poway, Calif., USA). The monoclonal anti-FLAG M2 antibody was from Stratagene (Cedar Creek, Tex., USA). The polyclonal anti-caspase-3 antibody (Asp175) was obtained from Cell Signaling Technology (Danvers, Mass., USA). The protease inhibitor cocktail was obtained from Roche (Indianapolis, Ind., USA) and the phosphatase inhibitor cocktail was from Pierce (Rockford, Ill., USA).

Construction of the PTK shRNA Library. A collection of short hairpin RNAs (shRNAs) targeting each of the PTKs were assembled from the pShagMagic2 (pSM2) shRNA library (Paddison et al., 2004; Silva et al. 2005). pSM2 shRNAs are modeled after pre-miRNAs and are transcribed by a pol III type promoter (U6) in a retroviral backbone. These vectors can be used to transfect cells to induce transient gene knockdown or they can be used to generate virus capable of infecting cells for long-term, continuous hairpin expression. In most cases, multiple shRNA constructs target the same gene, such that, over 300 shRNA clones were selected from the library to transfect into BT474 cells. Plasmid DNA was isolated, in 96-well format, from bacterial stocks containing each of the shRNAs using the Perfectprep Plasmid 96 Vac Direct Bind kit (Eppendorf, Hamburg, Germany).

RNAi screen-transfections. shRNA constructs were expressed from the pSHAGMAGIC 2 (pSM2) vector and derived from a genome-wide shRNA library (31). ShRNAs targeting the firefly (*Photinus pyralis*) luciferase gene were used as controls. Transfection efficiency was monitored by co-transfection with a modified MSCV-Puro vector expressing green fluorescent protein (GFP). The alamarBlue (Biosource) assay was performed 96 h post-transfection, since BT474 cells have a population doubling time of ~100 hours. Mature sequences of the shRNAs that produced the best results on decreasing BT474 viability are given in Table 1; a complete list is available in the RNAi Codex web page (codex.cshl.edu). The shRNAs targeting the luciferase gene were constructed as described in the RNAi Codex web page (codex.cshl.edu/scripts/newmain.pl) using a modified pSM2 vector containing the PheS gene (pSM2-PheS) in the cloning site, as a negative selection marker. Quantification of alamarBlue we used a BioTek HT Synergy plate reader. Transfections were performed using FuGENE 6 (Roche) according to the manufacturer's protocol. High-throughput transfections were performed using an EpMotion 5070 fluidics station (Eppendorf). Z-scores were calculated using the following formula: (normalized sample value−normalized data set mean)/data set standard deviation.

BTK was also knocked down using the siGEMOME SMART pool duplex (Dharmacon, Lafayette, CO, USA) transfected with Oligofectamine Reagent (Invitrogen, Gaithersburg, MD, USA) according to the manufacturer's instructions. BTK-C specific siRNAs were custom synthesized (Dharmacon, Lafayette, CO, USA): siRNA1 sense: GGUUA-UUGGAUGCCCAUUAUU (SEQ ID NO: 66), antisense: UAAUGGGCAUCCAAUAACCUU (SEQ ID NO: 67); siRNA2 sense: CAACAAAUGGUUAUUGGAUUU (SEQ ID NO: 68); antisense: AUCCAAUAACCAUUUGUUGUU (SEQ ID NO: 69).

Cell viability-apoptosis assays. For high-throughput experiments, cells grown on 96-well plates were washed once with 1×PBS, fixed with 2.5% formaldehyde and stained with Hoechst 33342 (Molecular Probes-Invitrogen). Cell images were acquired using an In Cell Analyzer 1000 (GE Healthcare) high content imaging system, with a 20× objective. At least 50 fields were imaged per single experiment. Cell counts and statistics were then performed using the In Cell Investigator 3.4 high-content image analysis software (GE Healthcare). Apoptosis was detected by cleaved Caspase-3 after 48 h to 96 h of shRNA treatments. Apoptosis was detected by cleaved Caspase-3 after 48 h of siRNA treatments or treatment with the BTK specific inhibitor LFM-A13. BT474 cells were treated with 35 µM LFM-A13. Control cells were treated with DMSO. For the cleaved caspase-3 assy, cells were fixed after treatment with 2.5% formaldehyde, washed with 1×PBS, permeabilized with 0.1% Triton-X 100 (Fisher Chemicals), blocked with 3% normal goat serum (Sigma-Aldrich), incubated with a 1:50-1:200 dilution of the primary antibody, washed with 1×PBS, incubated with a 1:800 dilution of the secondary antibody, washed again with 1×PBS and finally stained with Hoechst 33342 (Molecular Probes-Invitrogen). Cells were imaged by the In Cell Analyzer 1000 (GE Healthcare) or by a Leica TCS SP5 confocal microscope system (Leica Microsystems). At least 500 cells were counted for cleaved Caspase-3. Apoptotic cells were calculated as a percentage of the total cellular population. Antibodies used: cleaved Caspase-3 (Asp175, #9661; Cell Signaling Technology), Alexa Fluor 568 goat anti-rabbit IgG (#A-11011; Invitrogen) and Alexa Fluor 568 goat anti-mouse IgG (#A-11004; Invitrogen), and, Alexa Fluor 568 goat anti-rabbit IgG (#A-11011; Invitrogen).

Immunoblotting. Cell extracts for western blots (immunoblots) were obtained using RIPA buffer (1% Triton X-100, 40 mM NaCl, 0.1% SDS, 10 mM Tris pH 8.0) or non-denaturing lysis buffer: (20 mM Tris (pH 8.0), 137 mM NaCl, 10% glycerol, 1% Triton X-100, 2 mM EDTA), supplemented with complete cocktail of proteinase inhibitors (Roche). BT474 cells containing the stably integrated BTK-A-flag tag MarxIV, the BTK-C-flag tag MarxIV, and the 3-galactosidase MarxIV vectors were incubated with 100 µM LFM-A13 for 45 min. For detection of phoshporylated epitopes, the PhosSTOP cocktail of phospatase inhibitors (Roche) was added in the lysis buffer. Tyrosine-phosphorylated BTK was assessed by immunoprecipitation (IP) using anti-Flag and Western blot (WB) analysis using anti-BTK Phospho (pY223) and anti-BTK. Protein extracts were separated by SDS-PAGE, transferred to Immobilon-P (Millipore) membranes and immunoblotted according to standard protocols. Blots were imaged using a Fluor Chem HD (Alpha Innotech) imaging system. A polyclonal anti-BTK antibody (C-20), the monoclonal anti-BTK antibody (E-9) and a polyclonal anti-GAPDH antibody (V-18) were obtained from Santa Cruz Biotechnology (Santa Cruz, Calif., USA). A polyclonal anti-BTK antibody raised against residues 2-172, of BTK was obtained from Becton Dickinson (BD Transduction Laboratory, 611116). A polyclonal anti-BTK antibody used for immunofluorescence was obtained from ProSci Incorporated (Poway, Calif., USA). The monoclonal anti-FLAG M2 antibody was from Stratagene (Cedar Creek, Tex., USA). The polyclonal anti-caspase-3 antibody (Asp175) was obtained from Cell Signaling Technology (Danvers, Mass., USA). The protease inhibitor cocktail was obtained from Roche (Indianapolis, Ind., USA) and the phosphatase inhibitor cocktail was from Pierce (Rockford, Ill., USA). Antibodies used included: GAPDH (V-18; Santa Cruz Biotechnology), anti-rabbit IgG-HRP (sc2204, Santa Cruz Biotechnology), antigoat IgG-HRP (sc-2768, Santa Cruz Biotechnology), anti-mouse IgG-HRP (#31430; Pierce Biotechnology).

RNA isolation; quantitative polymerase chain reaction (qpcr); TaqMan-qPCR; RTPCR.

Total RNA was extracted from cells using TRizol (Invitrogen) according to the manufacturer's instructions, followed by the addition of DNaseI (Roche) for 20 min at 37° C. and purified using the RNeasy column (Qiagen, Valencia, Calif., USA) cleanup protocol. The cDNA was amplified using a modified version of the NIH/NCI Reid Lab cDNA synthesis protocol. A mixture containing 2-3.5 µg tRNA, 3 ul oligodT (Promega, Madison, Wis., USA) and 0.5 mM dNTPs was incubated at 65° C. for 5 minutes. Following incubation, 1×M-MLV reverse transcriptase buffer (Promega), and 256 U RNase Inhibitor (Fisher Scientific, Pittsburgh, Pa., USA), were added to the tRNA mixture and was incubated at 42° C. for 1 minute. 200u of M-MLV reverse transcriptase (Promega) was then added to the tRNA mixture and incubated at 42° C. for 1 hour, followed by a 15 minute incubation at 70° C. to inactivate the M-MLV enzyme. qPCR reactions using SYBR Green Master Mix (Applied Biosystems) or Taq SYBR Green Super Mix (BioRad), or TaqMan qPCR using TaqMan Gene Expression Master Mix (Applied Biosystems) were performed on a ABI PRISM 7900HT Sequence Detectin System (Applied Biosystems). TaqMan qPCR were performed using TaqMan Gene Expression Master Mix (Applied Biosystems) on a ABI PRISM 7900HT Sequence Detectin System (Applied Biosystems). The primer pairs used were designed using ABI's Primer Express software and are shown in Table 1. After the initial denaturation step (95° C. for 2.5 min), PCR reactions consisted of 40 cycles of a 95° C.-15 sec step, and a 60° C.-1 min step. Analysis was conducted using ABsystems Real-Time Analysis software Version 2.2. The RT-PCR amplification mix consisted of 1×Taq polymerase buffer (Fisher), 0.2 mM dNTPs, 0.2 uM Fwd Primer, 0.2 uM Rvs Primer (Table 1), ¹⁄₁₀th total volume cDNA (10 µl), and 5u Taq polymerase (Fisher) in a 100 µl total volume. After the initial denaturation step (95° C. for 2 min), PCR reactions consisted of 40 cycles of a 95° C.-30 sec step, 55° C.-30 sec step and a 72° C.-3 min step. Aliquots of each PCR reaction were electrophoresed on 1% agarose gels. The GeneRacer Kit (Invitrogen) was used, according to the manufacturer's specifications, for amplification of the N-terminal portion of the BTK message.

Measurement of BTK mRNA expression in normal and tumor tissues was performed using an array of first-strand complementary DNA (cDNA) from human breast tissues contained in the TissueScan Cancer Survey Panel in 384-well plates from OriGene (Rockville, Md.) (CSRT302). The cDNAs were prepared from normal breast tissues or breast adenocarcinoma biopsy samples. The cDNAs from one plate were used for measurement of BTK mRNA levels by real-time RT-PCR analysis. The same cDNAs in another plate were used for measurement of actin. The data presented are relative BTK isoform mRNA levels normalized to actin. This experiment was conducted twice with a representative dataset shown.

Small interfering RNA methodology. Btk was knocked down using the siGEMOME SMART pool duplex (Dharmacon, Lafayette, Colo., USA) transfected with Oligofectamine Reagent (Invitrogen, Gaithersburg, Md., USA) according to the manufacturer's instructions.

MarxIV triple flag tag vector construction. The triple flag tag sequence was amplified using the following reaction conditions; 100 ng of the pCMV-3Tag-3a Vector (Stratagene) as template, 1×Taq polymerase buffer (Fisher), 0.2 mM dNTPs, 0.2 uM each of the pCMV-3× Flag Fwd and Rvs primers (Table 1), and 5u Taq polymerase (Fisher). The PCR products were purified using spin columns (LPS inc.). The PCR DNA as well as the MarxIV vector DNA were double digested with 10u ApaI and 10u XhoI restriction endonucleases (NEB) in 1×NEB buffer #4 containing 1×BSA. The digested DNA was run on a 2% agarose gel and the desired DNA fragments were cut out and purified using the GeneClean Turbo kit (Qbiogene), according to the manufacturer's specifications. The double digested PCR flag tag product was ligated into the double digested MarxIV vector in using ApaI and XhoI restriction sites and 1× Ligase buffer (NEB), with 400 U Ligase. The ligase mix was transformed in 5-alpha competent E. coli cells (NEB) and plated on LB plates containing 100 µg/mL ampicillin (Amp). Colonies were picked and grown in LB+100 µg/mL Amp overnight for plasmid DNA preparations. Plasmid DNA was double digested with 10u Xho and 10u ApaI and run on a 2% agarose gel to determine which colonies contain the MarxIV vector with the integrated triple flag tag sequence. The BTK-A and BTK-C sequences were amplified using a proofreading Taq polymerase (Phusion DNA polymerase, NEB), according to the manufacturers specifications.

Construction of the Btk-A and Btk-C MarxIV and MarxIV triple flag tag vectors. The Btk-A sequence was amplified using Namalwa cDNA (10 ul) as a template with the Btk-Flag primer set (Table 1). The Btk-C sequence was amplified using over-lap extension PCR (OLE). BTK-C(N-terminus) was amplified using 10 ng pCR2.1-TOPO plasmid DNA (Invitrogen) containing the N-terminal Btk-C sequence (constructed in the 5'RACE experiment) as template with the N-term-BTK-C primer set (Table 1). The amplification reaction conditions were 0.5 mM of each of the N-term-Btk-C primers (Table 1), 1× Phusion DNA polymerase buffer (NEB), 0.2 mM dNTPs and 2u Phusion DNA polymerase (NEB). The second amplification reaction amplified the C-terminal portion of the Btk-C gene using similar conditions as above except rather than plasmid DNA, Namalwa cDNA was used as template and the Btk-C-terminus primer set (Table 1) was used for amplification in 100µl total volume. BTK-C (full-length) was amplified using the BTK-C(N-terminus) and BTK-C(C-terminus) PCR DNAs as template with the BTK-C-Flag primer set. The BTK-C (full-length) PCR product was cloned into the MarxIV-Flag vector using BamHI and XhoI (NEB) restriction sites. The BTK-A PCR product was cloned into the MarxIV-Flag vector using MfeI and XhoI (NEB) restriction sites. Selected clones were sequence-verified. PCR products resulting from these amplification reactions were purified using Uprep Spin columns (LPS inc.) and both were subsequently used in a third amplification reaction to generate a PCR product of the complete Btk-C sequence. The amplification reaction conditions were N-terminus PCR product, C-terminus PCR product, 0.5 mM each of the Btk-C-Flag primer set, 1× Phusion DNA polymerase buffer, 0.2 mM dNTPs and 2u Phusion DNA polymerase. The full-length Btk-C PCR product as well as the MarxIV triple flag vector DNA were Uprep column purified (LPS inc.) and double-digested using 10u BamHI and 10u XhoI restriction endonucleases. The Btk-A PCR product was double-digested using 10u MfeI and 10u XhoI restriction endonucleases. The digested DNA was run on a 1% agarose gel and the desired DNA fragments were cut out and purified using the GeneClean Turbo kit (Qbiogene), according to the manufacturer's specifications. Each of the double-digested Btk-A and Btk-C PCR products were ligated into the double-digested MarxIV triple flag tag vector using 1× Ligase buffer (NEB), with 400 U Ligase. The ligase mix was transformed in competent E. coli cells and plated on LB plates containing ampicillin (100 µg/mL Amp) Colonies were picked and grown in LB+100 µg/mL Amp overnight for plasmid DNA preparations. Plasmid DNA was double digested with 10u Xho and 10u BamHI (Btk-C) insert or 10u XhoI and 10u MfeI (Btk-A) insert and run on a 1% agarose gel to determine which colonies contained the Btk-A or Btk-C DNA fragment within the MarxIV triple flag tag vector. Selected clones were sequence verified.

Stable infections and selection. BT474 cells that over-express MarxIV-Flag, Btk-A MarxIV-Flag or Btk-C-MarxIV-Flag were selected with 75 µg/ml Hygromycin B (Roche Diagnostics) for 10 days after infection with retrovirus produced by Phoenix A cells, transfected with either the MarxIV-Flag, Btk-A-Flag or Btk-C-Flag.

5'RACE. Total RNA was extracted from BT474 cells using TRizol (Invitrogen), according to the manufacturer's instructions. The tRNA was then incubated with DNase1 (Roche) for 20 min at 37° C., and then purified using RNeasy (Qiagen, Valencia, Calif., USA) RNA Cleanup protocol. The GeneRacer Kit (Invitrogen) was used, according to the manufacturer's specifications, for amplification of the N-terminal portion of the Btk message. Briefly, the 5' Cap was removed from full-length mRNAs. The GeneRacer Oligo was ligated to the message RNAs (mRNAs). The mRNA was reverse transcribed into cDNA. The Btk specific transcript was amplified in a first round of amplification using the GeneRacer 5' Primer (complementary to the GeneRacer Oligo sequence) and the Btk-RACE Primer (Table 1). In a second round of amplification 1 ul of the product from the first amplification reaction was used as substrate with the Btk-RACE-Nest 3' primer and the GeneRacer 5' Nested primer (Table 1). The product was gel extracted and ligated into the PCR2.1-TOPO vector. The inserted DNA fragment was sequence verified.

BTK Immunolocalization. Cells were immunostained on cover slips with anti-BTK antibody (ProSci); anti-Flag antibody (Stratagene) and Alexa568 conjugated secondary antibody, with Hoechst to stain nuclei, and were imaged using a Leica TCS SP5 confocal microscope system (Leica Microsystems Inc., Bannockburn, Ill., USA). Breast cancer tissue arrays were obtained from Biomax.us (BRC-961) and contained 96 breast cancer cases with a range of disease stages and patient ages. Arrays were processed with standard immunohistochemical procedures. Briefly, slides were baked at 65° C. for 1 hour, then de-parrafinized in HistoChoice clearing agent, and rehydrated through a series of decreasing concentrations of ethanol (100, 95, 70, 50%) and finally into PBS. Slides were washed with PBS/0.3% Triton X-100 for 10 minutes and epitopes retrieved in a pressure cooker for 20 minutes. Sections were then blocked in 10% donkey serum/3% BSA in PBS and then incubated 0/N at 4° C. with BTK antibody (1:200 dillution in 3% BSA/PBS). Slides were washed in PBS and primary antibody detected with Cy5 donkey anti-mouse secondary antibody (1:250 dilution in 3% BSA/PBS, Jackson Immunologicals). Slides were washed, stained in DAPI to visualize the nuclei, rinsed, and mounted with DABCO antifade in 90% glycerol. TMA cores were imaged on a Zeiss AxioImager Z1 equipped for epifluorescence with at 300W Zenon exicitation source, 20×0.8 n.a. objective, filter sets optimized for DAP1 and CY5 (Semrock) and a Hammamatsu ORCA digital CCD camera. Exposure for DAP1 and CY5 was fixed across the tissue array sample, and autofocusing was used after pre-setting coordinates for image acquisition using the AxioVision software (Carl Zeiss).

TABLE 1

| Gene | Primer Name | SEQ ID Fwd Primer | SEQ ID RVs Primer |
|---|---|---|---|
| BTK | Btk-Full | 4 5'-TGAACTCCAGAAAGAAGAAGGTATG-3' | 5 5'-CCTCCCCTCCCATCTTTATG-3' |
| BTK | Btk-Internal | 6 5'-CGTCTTCTCCCCAACTGAAG-3' | 7 5'-TTTGAAAGTGGGACGCTCAT-3' |
| BTK-A | Btk-A-specific | 8 5'-TGCTGCGATCGAGTCCCAC-3' | 9 5'-TTTGAAAGTGGGACGCTCAT-3' |
| BTK-C | Btk-C-specific | 10 5'-AAATGGTTATTGGATGCCCATT-3' | 11 5'-TTTGAAAGTGGGACGCTCAT-3' |
| BTK-C | qPCR-Btk-C-specific | 12 5'-AAATGGTTATTGGATGCCCATT-3' | 13 5'-TCTTCTTTCTGGAGTTCACCTGTCT-3' |

TABLE 1-continued

| Gene | Primer Name | SEQ ID | Fwd Primer | SEQ ID | RVs Primer |
|---|---|---|---|---|---|
| BTK-A | Taq-Btk-A-specific | 14 | 5'-TCCTTCCTCTCTGGACTGTAAGAATAT-3' | 15 | 5'-ACTTGGAAGGTGGGACTCGAT-3' |
| | Taq-Btk-A-specific Probe | 16 | 5'-56-FAM/TCTCCAGGGCCAGTGTCTGCTGC/36-TAMSp-3' | | |
| BTK-C | Taq-Btk-C-specific | 17 | 5'-TCTTTTGGTGGACTCTGCTACGT-3' | 18 | 5'-GGCCAGAGGATCTGGGAAA-3' |
| | Taq-Btk-C-specific Probe | 19 | 5'-56-FAM/TGGCGTTCAGTGAAGGGAGCAGTGT/36-TAMSp-3' | | |
| Flag tag | pCMV-3X Flag | 20 | 5'-GTGAACCGTCAGATCCGCTA-3' | 21 | 5'-AGGTACGGGCCCCTATTTATCGTCATCATCTTTGT-3' |
| BTK-A | BTK-A-Flag | 22 | 5'-AAAGAACAATTGATGGCCGCAGTGATTCTGGAG-3' | 23 | 5'-CTTATCTCGAGGGATTCTTCATCCATGACATC-3' |
| BTK-C | N-term-Btk-C | 24 | 5'-AGAGTGGATCCGCCACCCTTTATCTCTTTTGGTGGACTC-3' | 25 | 5'-CCAGAATCACTGCGGCCAT-3' |
| BTK-C | C-term-Btk-C | 26 | 5'-ATGGCCGCAGTGATTCTGG-3' | 27 | 5'-CTTATCTCGAGGGATTCTTCATCCATGACATC-3' |
| BTK-C | BTK-C-Flag | 28 | 5'-AGAGTGGATCCGCCACCCTTTATCTCTTTTGGTGGACTC-3' | 29 | 5'-CTTATCTCGAGGGATTCTTCATCCATGACATC-3' |
| BTK | BTK-RACE | 30 | 5'-GAGCTGGTGAATCCACCGCTTCCTTAGTTCTTC-3' | 31 | 5'-CGACTGGAGCACGAGGACACTGA-3' |
| BTK | BTK-RACE-Nest | 32 | 5'-AGTTGGGGAGAAGACGTAGAGAGGCCCTTCAT-3' | 33 | 5'-GGACACTGACATGGACTGAAGGAGTA-3' |

TABLE 2

Tyrosine kinase genes which when silenced result in greater than 50% reduction in normalized proliferation.

| Symbol | Name | z-score |
|---|---|---|
| ABL2 | V-abl Abelson murine leukemia viral oncogene homolog 2 | −5.68 |
| BTK | Bruton agammaglobulinemia tyrosine kinase | −4.95 |
| FES | Feline sarcoma oncogene | −4.35 |
| NTRK2 | Neurotrophic tyrosine kinase, receptor, type 2 | −3.95 |
| PTK2B | Protein tyrosine kinase 2 beta | −3.95 |
| Ptk9 | Protein tyrosine kinase 9 | −3.38 |
| FGFR2 | Fibroblast growth factor receptor 2 | −3.20 |
| EPHA1 | EPH receptor A1 | −3.00 |
| LYN | V-yes-1 Yamaguchi sarcoma viral related oncogene homolog | −2.93 |
| FLT3 | Fms-related tyrosine kinase 3 | −2.78 |
| IGF1R | Insulin-like growth factor 1 receptor | −2.68 |
| EGFR | Epidermal growth factor receptor | −2.45 |
| JAK1 | Janus kinase 1 (a protein tyrosine kinase) | −2.25 |
| DDR1 | Discoidin domain receptor family, member 1 | −2.15 |
| TXK | TXK tyrosine kinase | −2.08 |
| EPHB2 | EPH receptor B2 | −2.08 |
| EPHA4 | EPH receptor A4 | −2.05 |
| RYK | RYK receptor-like tyrosine kinase | −1.95 |
| PDGFRB | Platelet-derived growth factor receptor, beta polypeptide | −1.83 |
| ERBB2 | V-erb-bZ erythroblastic leukemia viral oncogene homolog 2 | −1.80 |
| ZAP70 | Zeta-chain (TCR) associated protein kinase 70 kDa | −1.70 |
| JAK2 | Janus kinase 2 (a protein tyrosine kinase) | −1.45 |
| BMX | BMX non-receptor tyrosine kinase | −1.43 |
| TEC | Tec protein tyrosine kinase | −1.30 |
| EPHB6 | EPH receptor B6 | −1.15 |

TABLE 3

| Symbol | Location | SEQ ID | Sequence |
|---|---|---|---|
| POU3F2 | −902 | 44 | TTATCttaat |
| Pax-6 | −801 | 45 | accaaattataCGGAAtccat |
| SZF1-1 | −785 | 46 | tccatcttaCCCTGg |
| Spz1 | −694 | 47 | tccGGCGGgttttag |
| PPARG | −686 | 48 | gttttagggacgtTAAC-Ctagta |
| HNF3beta | −668 | 49 | taaagAAACAgttca |
| VDR, CAR, PXR | −660 | 50 | aaacaGTTCAgaacgtgcaat |
| 1-Oct | −573 | 51 | tcctcATTACttg |
| IPF1 | −477 | 52 | cctCATTAactc |
| CACD | −466 | 53 | ccaCCCCC |
| ZF5 | −412 | 54 | taGCCCGgtccct |
| HOXA7 | −381 | 55 | aGATTGg |
| BRCA1:USF2 | −378 | 56 | ttgGGTTG |
| Muscle initiator sequences-19 | −362 | 57 | tatcgagtcCACACaggag |
| CP2/LBP-lc/LSF | −293 | 58 | GCTGGatgttactcg |
| Pax-8 | −257 | 59 | catgcttgCGTGAgc |
| AhR | −253 | 60 | cttGCGTGagc |
| v-Myb | −211 | 61 | gcaAACGGa |

TABLE 3-continued

| Symbol | Location | SEQ ID | Sequence |
|---|---|---|---|
| c-Ets-I(p54) (ETS1) | -210 | 62 | caaaCGGAAgtat |
| CDP_CR3 | -208 | 63 | aacggaagtaTATAG |
| AP-2 | -125 | 64 | cgCCCTCgggcg |
| Ets | -41 | 65 | aCTTCCtc |

The invention claimed is:

1. A method of treating cancer, comprising:
   a) providing:
      i) subject with breast cancer,
      ii) a chemotherapeutic agent, and
      iii) an inhibitor of a gene encoding a cytoplasmic tyrosine kinase, wherein said inhibitor comprises an interfering double stranded RNA selected from the group consisting of: sense strand having the nucleotide sequence of SEQ ID NO: 66, an antisense strand having the nucleotide sequence of SEQ ID NO: 67, a sense strand having the nucleotide sequence of SEQ ID NO: 68, and an antisense strand having the nucleotide sequence of SEQ ID NO: 69; and
   b) treating said subject with said chemotherapeutic agent and said inhibitor.

2. The method of claim 1, wherein said cytoplasmic tyrosine kinase is Bruton's Tyrosine Kinase.

3. The method of claim 1, wherein said cytoplasmic tyrosine kinase is a variant of Bruton's Tyrosine Kinase comprising an amino-terminal extension.

4. The method of claim 3, wherein said extension comprises an additional 34 amino acids.

5. The method of claim 1, wherein said chemotherapeutic agent comprises Doxorubicin.

6. The method of claim 1, wherein treating with said chemotherapeutic agent and said inhibitor results in reduced proliferation of the breast cancer cells within said subject.

7. A method of treating cancer, comprising:
   a) providing:
      i) subject with breast cancer,
      ii) a chemotherapeutic agent, and
      iii) an inhibitor of a gene encoding a cytoplasmic tyrosine kinase, wherein said inhibitor comprises a mixture of interfering double stranded RNAs comprising a sense strand having the nucleotide sequence of SEQ ID NOs: 66 and 68 and an antisense strand having the nucleotide sequence of SEQ ID NOs: 67 and 69; and b) treating said subject with said chemotherapeutic agent and said inhibitor.

8. The method of claim 1, A method of treating cancer, comprising:
a) providing:
i) a subject with breast cancer cells, at least some of said breast cancer cells exhibiting resistance to a chemotherapeutic agent, and
ii) an inhibitor of a gene encoding a cytoplasmic tyrosine kinase, wherein said inhibitor comprises interfering double stranded RNA selected from the group consisting of: sense strand having the nucleotide sequence of SEQ ID NO: 66, an antisense strand having the nucleotide sequence of SEQ ID NO: 67, a sense strand having the nucleotide sequence of SEQ ID NO: 68, and an antisense strand having the nucleotide sequence of SEQ ID NO: 69, and
b) treating said subject with said inhibitor.

9. The method of claim 8, wherein said cytoplasmic tyrosine kinase is Bruton's Tyrosine Kinase.

10. The method of claim 8, wherein said cytoplasmic tyrosine kinase is a variant of Bruton's Tyrosine Kinase comprising an amino-terminal extension.

11. The method of claim 10, wherein said extension comprises an additional 34 amino acids.

12. The method of claim 8, wherein treating with said inhibitor results in reduced proliferation of at least some of said breast cancer cells within said subject.

13. The method of claim 8, wherein said inhibitor results in reduced proliferation of at least some breast cancer cells within said subject identified as resistant to said chemotherapeutic agent.

14. A method of treating cancer, comprising:
a) providing:
i) a subject with breast cancer cells, at least some of said breast cancer cells exhibiting resistance to a chemotherapeutic agent, and
ii) an inhibitor of a gene encoding a cytoplasmic tyrosine kinase, wherein said inhibitor comprises a mixture of interfering double stranded RNAs comprising a sense strand having the nucleotide sequence of SEQ ID NOs: 66 and 68 and an antisense strand having the nucleotide sequence of SEQ ID NOs: 67 and 69, and
b) treating said subject with said inhibitor.

15. A method of treating cancer, comprising:
a) providing:
i) a subject with breast cancer,
ii) a chemotherapeutic agent, and
iii) an inhibitor of a gene encoding a cytoplasmic tyrosine kinase wherein said inhibitor comprises interfering double stranded RNA selected from the group consisting of: sense strand having the nucleotide sequence of SEQ ID NO: 66, an antisense strand having the nucleotide sequence of SEQ ID NO: 67, a sense strand having the nucleotide sequence of SEQ ID NO: 68, and an antisense strand having the nucleotide sequence of SEQ ID NO: 69,
b) treating said subject with said inhibitor; and
c) after step b), treating said subject with said chemotherapeutic.

16. The method of claim 15, wherein said cytoplasmic tyrosine kinase is Bruton's Tyrosine Kinase.

17. The method of claim 15, wherein said cytoplasmic tyrosine kinase is a variant of Bruton's Tyrosine Kinase comprising an amino-terminal extension.

18. The method of claim 17, wherein said extension comprises an additional 34 amino acids.

19. The method of claim 15, wherein said chemotherapeutic agent comprises Doxorubicin.

20. The method of claim 15, wherein treating with said chemotherapeutic agent results in reduced proliferation of the breast cancer cells within said subject.

21. The method of claim 15, wherein said inhibitor results in reduced proliferation of the breast cancer cells within said subject.

22. A method of treating cancer, comprising:
a) providing:
i) a subject with breast cancer,
ii) a chemotherapeutic agent, and
iii) an inhibitor of a gene encoding a cytoplasmic tyrosine kinase, wherein said inhibitor comprises a mixture of interfering double stranded RNAs comprising a sense strand having the nucleotide sequence of SEQ ID NOs: 66 and 68 and an antisense strand having the nucleotide sequence of SEQ ID NOs: 67 and 69,
b) treating said subject with said inhibitor; and
c) after step b), treating said subject with said chemotherapeutic.

* * * * *

UNITED STATES PATENT AND TRADEMARK OFFICE
CERTIFICATE OF CORRECTION

PATENT NO. : 9,095,592 B2  
APPLICATION NO. : 13/971662  
DATED : August 4, 2015  
INVENTOR(S) : Douglas Conklin et al.

It is certified that error appears in the above-identified patent and that said Letters Patent is hereby corrected as shown below:

In the specification

Column 1, lines 8-9 should read

This invention was made with government support under grant number DAMD17-02-1-0729 awarded by the U.S. Army Medical Research Materiel Command and under grant number CA136658 awarded by the National Institutes of Health. The government has certain rights in the invention.

Signed and Sealed this  
Fifth Day of January, 2016

Michelle K. Lee  
*Director of the United States Patent and Trademark Office*

SEQUENCE LISTING

<160> NUMBER OF SEQ ID NOS: 69

<210> SEQ ID NO 1
<211> LENGTH: 396
<212> TYPE: DNA
<213> ORGANISM: Homo sapiens

<400> SEQUENCE: 1

```
actcaagata gtagtgtcag aggtcccaac caaatgaagg gcggggacag ttgaggqggt    60
ggaataggga cggcagcagg gaaccagata gcatgctgct gagaagaaaa aaagacattg   120
gtttaggtca ggaaccaaaa aaagggaact gagtggctgt gaaagggtgg ggtttgctca   180
gactgtcctt cctctctgga ctgtaagaat atgtctccag ggccagtgtc tgctgcgatc   240
gagtcccacc ttccaagtcc tggcatctca atgcatctgg gaagctacct gcattaagtc   300
aggactgagc acacaggtga actccagaaa gaagaagcta tggccgcagt gattctggag   360
agcatctttc tgaagcgatc ccaacagaaa aagaaa                             396
```

<210> SEQ ID NO 2
<211> LENGTH: 399
<212> TYPE: DNA
<213> ORGANISM: Homo sapiens

<400> SEQUENCE: 2

```
ctttatctct tttggtggac tctgctacgt agtggcgttc agtgaaggga gcagtgtttt    60
tcccagatcc tctggcctcc ccgtcccega gggaagccag gactagggtc gaatgaaggg   120
gtcctccacc tccacgttcc attcctgttc caccteaagg tcactgggaa cacctttege   180
agcaaactgc taattcaatg aagacctgga gggagccaat tgttccagtt catctatcac   240
atggccagtt ggtccattca acaaatggtt attggatgcc cattatgtgg caggcactgt   300
tccgggggag agcacacagg tgaactccag aaagaagaag ctatggccgc agtgattctg   360
gagagcatct ttctgaagcg atcccaacag aaaaagaaa                          399
```

<210> SEQ ID NO 3
<211> LENGTH: 53
<212> TYPE: PRT
<213> ORGANISM: Homo sapiens

<400> SEQUENCE: 3

Met Ala Ser Trp Ser Ile Gln Gln Met Val Ile Gly Cys Pro Leu Cys
1               5                   10                  15

Gly Arg His Cys Ser Gly Gly Glu His Thr Gly Glu Leu Gln Lys Glu
            20                  25                  30

Glu Ala Met Ala Ala Val Ile Leu Glu Ser Ile Phe Leu Lys Arg Ser
        35                  40                  45

Gln Gln Lys Lys Lys
    50

```
<210> SEQ ID NO 4
<211> LENGTH: 25
<212> TYPE: DNA
<213> ORGANISM: Homo sapiens

<400> SEQUENCE: 4
tgaactccag aaagaagaag ctatg                                              25

<210> SEQ ID NO 5
<211> LENGTH: 20
<212> TYPE: DNA
<213> ORGANISM: Homo sapiens

<400> SEQUENCE: 5
cctcccctcc catctttatg                                                    20

<210> SEQ ID NO 6
<211> LENGTH: 20
<212> TYPE: DNA
<213> ORGANISM: Homo sapiens

<400> SEQUENCE: 6
cgtcttctcc ccaactgaag                                                    20

<210> SEQ ID NO 7
<211> LENGTH: 20
<212> TYPE: DNA
<213> ORGANISM: Homo sapiens

<400> SEQUENCE: 7
tttgaaagtg ggacgctcat                                                    20

<210> SEQ ID NO 8
<211> LENGTH: 19
<212> TYPE: DNA
<213> ORGANISM: Homo sapiens

<400> SEQUENCE: 8
tgctgcgatc gagtcccac                                                     19

<210> SEQ ID NO 9
<211> LENGTH: 20
<212> TYPE: DNA
<213> ORGANISM: Homo sapiens

<400> SEQUENCE: 9
tttgaaagtg ggacgctcat                                                    20

<210> SEQ ID NO 10
<211> LENGTH: 22
<212> TYPE: DNA
<213> ORGANISM: Homo sapiens

<400> SEQUENCE: 10
aaatggttat tggatgccca tt                                                 22

<210> SEQ ID NO 11
<211> LENGTH: 20
<212> TYPE: DNA
<213> ORGANISM: Homo sapiens

<400> SEQUENCE: 11
tttgaaagtg ggacgctcat                                                    20
```

-continued

```
<210> SEQ ID NO 12
<211> LENGTH: 22
<212> TYPE: DNA
<213> ORGANISM: Homo sapiens

<400> SEQUENCE: 12
aaatggttat tggatgccca tt                                              22

<210> SEQ ID NO 13
<211> LENGTH: 25
<212> TYPE: DNA
<213> ORGANISM: Homo sapiens

<400> SEQUENCE: 13
tcttctttct ggagttcacc tgtct                                           25

<210> SEQ ID NO 14
<211> LENGTH: 27
<212> TYPE: DNA
<213> ORGANISM: Homo sapiens

<400> SEQUENCE: 14
tccttcctct ctggactgta agaatat                                         27

<210> SEQ ID NO 15
<211> LENGTH: 21
<212> TYPE: DNA
<213> ORGANISM: Homo sapiens

<400> SEQUENCE: 15
acttggaagg tgggactcga t                                               21

<210> SEQ ID NO 16
<211> LENGTH: 23
<212> TYPE: DNA
<213> ORGANISM: Homo sapiens

<400> SEQUENCE: 16
tctccagggc cagtgtctgc tgc                                             23

<210> SEQ ID NO 17
<211> LENGTH: 23
<212> TYPE: DNA
<213> ORGANISM: Homo sapiens

<400> SEQUENCE: 17
tcttttggtg gactctgcta cgt                                             23

<210> SEQ ID NO 18
<211> LENGTH: 19
<212> TYPE: DNA
<213> ORGANISM: Homo sapiens

<400> SEQUENCE: 18
ggccagagga tctgggaaa                                                  19

<210> SEQ ID NO 19
<211> LENGTH: 25
<212> TYPE: DNA
<213> ORGANISM: Homo sapiens

<400> SEQUENCE: 19
tggcgttcag tgaagggagc agtgt                                           25
```

```
<210> SEQ ID NO 20
<211> LENGTH: 20
<212> TYPE: DNA
<213> ORGANISM: Homo sapiens

<400> SEQUENCE: 20
gtgaaccgtc agatccgcta                                                    20

<210> SEQ ID NO 21
<211> LENGTH: 35
<212> TYPE: DNA
<213> ORGANISM: Homo sapiens

<400> SEQUENCE: 21
aggtacgggc ccctatttat cgtcatcatc tttgt                                   35

<210> SEQ ID NO 22
<211> LENGTH: 33
<212> TYPE: DNA
<213> ORGANISM: Homo sapiens

<400> SEQUENCE: 22
aaagaacaat tgatggccgc agtgattctg gag                                     33

<210> SEQ ID NO 23
<211> LENGTH: 32
<212> TYPE: DNA
<213> ORGANISM: Homo sapiens

<400> SEQUENCE: 23
cttatctcga gggattcttc atccatgaca tc                                      32

<210> SEQ ID NO 24
<211> LENGTH: 39
<212> TYPE: DNA
<213> ORGANISM: Homo sapiens

<400> SEQUENCE: 24
agagtggatc cgccaccctt tatctctttt ggtggactc                               39

<210> SEQ ID NO 25
<211> LENGTH: 19
<212> TYPE: DNA
<213> ORGANISM: Homo sapiens

<400> SEQUENCE: 25
ccagaatcac tgcggccat                                                     19

<210> SEQ ID NO 26
<211> LENGTH: 19
<212> TYPE: DNA
<213> ORGANISM: Homo sapiens

<400> SEQUENCE: 26
atggccgcag tgattctgg                                                     19

<210> SEQ ID NO 27
<211> LENGTH: 32
<212> TYPE: DNA
<213> ORGANISM: Homo sapiens

<400> SEQUENCE: 27
```
cttatctcga gggattcttc atccatgaca tc                                      32

<210> SEQ ID NO 28
<211> LENGTH: 39
<212> TYPE: DNA
<213> ORGANISM: Homo sapiens

<400> SEQUENCE: 28
agagtggatc cgccacccct tatctctttt ggtggactc                               39

<210> SEQ ID NO 29
<211> LENGTH: 32
<212> TYPE: DNA
<213> ORGANISM: Homo sapiens

<400> SEQUENCE: 29
cttatctcga gggattcttc atccatgaca tc                                      32

<210> SEQ ID NO 30
<211> LENGTH: 33
<212> TYPE: DNA
<213> ORGANISM: Homo sapiens

<400> SEQUENCE: 30
gagctggtga atccaccgct tccttagttc ttc                                     33

<210> SEQ ID NO 31
<211> LENGTH: 23
<212> TYPE: DNA
<213> ORGANISM: Homo sapiens

<400> SEQUENCE: 31
cgactggagc acgaggacac tga                                                23

<210> SEQ ID NO 32
<211> LENGTH: 32
<212> TYPE: DNA
<213> ORGANISM: Homo sapiens

<400> SEQUENCE: 32
agttggggag aagacgtaga gaggcccttc at                                      32

<210> SEQ ID NO 33
<211> LENGTH: 26
<212> TYPE: DNA
<213> ORGANISM: Homo sapiens

<400> SEQUENCE: 33
ggacactgac atggactgaa ggagta                                             26

<210> SEQ ID NO 34
<211> LENGTH: 316
<212> TYPE: PRT
<213> ORGANISM: Homo sapiens

<400> SEQUENCE: 34

Leu Arg Ile Leu Lys Glu Thr Glu Phe Lys Lys Ile Lys Val Leu Gly
1               5                   10                  15

Ser Gly Ala Phe Gly Thr Val Tyr Lys Gly Leu Trp Ile Pro Glu Gly
            20                  25                  30

Glu Lys Val Lys Ile Pro Val Ala Ile Lys Glu Leu Arg Glu Ala Thr
        35                  40                  45

```
Ser Pro Lys Ala Asn Lys Glu Ile Leu Asp Glu Ala Tyr Val Met Ala
    50                  55                  60

Ser Val Asp Asn Pro His Val Cys Arg Leu Leu Gly Ile Cys Leu Thr
65                  70                  75                  80

Ser Thr Val Gln Leu Ile Thr Gln Leu Met Pro Phe Gly Cys Leu Leu
                85                  90                  95

Asp Tyr Val Arg Glu His Lys Asp Asn Ile Gly Ser Gln Tyr Leu Leu
                100                 105                 110

Asn Trp Cys Val Gln Ile Ala Lys Gly Met Asn Tyr Leu Glu Asp Arg
            115                 120                 125

Arg Leu Val His Arg Asp Leu Ala Ala Arg Asn Val Leu Val Lys Thr
130                 135                 140

Pro Gln His Val Lys Ile Thr Asp Phe Gly Leu Ala Lys Leu Leu Gly
145                 150                 155                 160

Ala Glu Glu Lys Glu Tyr His Ala Glu Gly Gly Lys Val Pro Ile Lys
                165                 170                 175

Trp Met Ala Leu Glu Ser Ile Leu His Arg Ile Tyr Thr His Gln Ser
            180                 185                 190

Asp Val Trp Ser Tyr Gly Val Thr Val Trp Glu Leu Met Thr Phe Gly
            195                 200                 205

Ser Lys Pro Tyr Asp Gly Ile Pro Ala Ser Glu Ile Ser Ser Ile Leu
210                 215                 220

Glu Lys Gly Glu Arg Leu Pro Gln Pro Pro Ile Cys Thr Ile Asp Val
225                 230                 235                 240

Tyr Met Ile Met Val Lys Cys Trp Met Ile Asp Ala Asp Ser Arg Pro
                245                 250                 255

Lys Phe Arg Glu Leu Ile Ile Glu Phe Ser Lys Met Ala Arg Asp Pro
            260                 265                 270

Gln Arg Tyr Leu Val Ile Gln Gly Asp Glu Arg Met His Leu Pro Ser
                275                 280                 285

Pro Thr Asp Ser Asn Phe Tyr Arg Ala Leu Met Asp Glu Glu Asp Met
290                 295                 300

Asp Asp Val Val Asp Ala Asp Glu Tyr Leu Ile Pro
305                 310                 315

<210> SEQ ID NO 35
<211> LENGTH: 256
<212> TYPE: PRT
<213> ORGANISM: Homo sapiens

<400> SEQUENCE: 35

Arg Lys Val Lys Val Leu Gly Ser Gly Ala Phe Gly Thr Val Tyr Lys
1               5                   10                  15

Gly Ile Trp Ile Pro Asp Gly Glu Asn Val Lys Ile Pro Val Ala Ile
            20                  25                  30

Lys Val Leu Arg Glu Asn Thr Ser Pro Lys Ala Asn Lys Glu Ile Leu
        35                  40                  45

Asp Glu Ala Tyr Val Met Ala Gly Val Gly Ser Pro Tyr Val Ser Arg
    50                  55                  60

Leu Leu Gly Ile Cys Leu Thr Ser Thr Val Gln Leu Val Thr Gln Tyr
65                  70                  75                  80

Leu Pro Leu Gly Ser Leu Leu Asp His Val Arg Gln His Arg Gly Ala
                85                  90                  95

Leu Gly Pro Gln Leu Leu Leu Asn Trp Gly Val Gln Ile Ala Lys Gly
            100                 105                 110
```

```
Met Tyr Tyr Leu Glu Glu His Gly Met Val His Arg Asn Leu Ala Ala
            115                 120                 125

Arg Asn Val Leu Leu Lys Ser Pro Ser Gln Val Gln Val Ala Asp Phe
        130                 135                 140

Gly Val Ala Asp Leu Leu Asp Ile Asp Glu Thr Glu Tyr His Ala Asp
145                 150                 155                 160

Gly Gly Lys Val Pro Ile Lys Trp Met Ala Leu Glu Ser Ile Leu Arg
                165                 170                 175

Arg Arg Phe Thr His Gln Ser Asp Val Trp Ser Tyr Gly Val Thr Val
            180                 185                 190

Trp Glu Leu Met Thr Phe Gly Ala Lys Pro Tyr Asp Gly Ile Pro Ala
            195                 200                 205

Arg Glu Ile Pro Asp Leu Leu Glu Lys Gly Glu Arg Leu Pro Gln Pro
        210                 215                 220

Pro Ile Cys Thr Ile Asp Val Tyr Met Val Met Val Lys Cys Trp Met
225                 230                 235                 240

Ile Asp Glu Asn Ile Arg Pro Thr Phe Lys Glu Leu Ala Asn Glu Phe
                245                 250                 255

<210> SEQ ID NO 36
<211> LENGTH: 256
<212> TYPE: PRT
<213> ORGANISM: Homo sapiens

<400> SEQUENCE: 36

Arg Lys Leu Lys Val Leu Gly Ser Gly Val Phe Gly Thr Val His Lys
1               5                   10                  15

Gly Val Trp Ile Pro Glu Gly Glu Ser Ile Lys Ile Pro Val Cys Ile
            20                  25                  30

Lys Val Ile Glu Asp Lys Ser Gly Arg Gln Ser Phe Gln Ala Val Thr
        35                  40                  45

Asp His Met Leu Ala Ile Gly Ser Leu Asp His Ala His Ile Val Arg
    50                  55                  60

Leu Leu Gly Leu Cys Pro Gly Ser Ser Leu Gln Leu Val Thr Gln Tyr
65                  70                  75                  80

Leu Pro Leu Gly Ser Leu Leu Asp His Val Arg Gln His Arg Gly Ala
                85                  90                  95

Leu Gly Pro Gln Leu Leu Leu Asn Trp Gly Val Gln Ile Ala Lys Gly
            100                 105                 110

Met Tyr Tyr Leu Glu Glu His Gly Met Val His Arg Asn Leu Ala Ala
            115                 120                 125

Arg Asn Val Leu Leu Lys Ser Pro Ser Gln Val Gln Val Ala Asp Phe
        130                 135                 140

Gly Val Ala Asp Leu Leu Pro Pro Asp Asp Lys Gln Leu Leu Tyr Ser
145                 150                 155                 160

Glu Ala Lys Thr Pro Ile Lys Trp Met Ala Leu Glu Ser Ile His Phe
                165                 170                 175

Gly Lys Tyr Thr His Gln Ser Asp Val Trp Ser Thr Gly Val Thr Val
            180                 185                 190

Trp Glu Leu Met Thr Phe Gly Ala Glu Pro Tyr Ala Gly Leu Arg Leu
            195                 200                 205

Ala Glu Val Pro Asp Leu Leu Glu Lys Gly Glu Arg Leu Ala Gln Pro
        210                 215                 220

Gln Ile Cys Thr Ile Asp Val Tyr Met Val Met Val Lys Cys Trp Met
```

```
                    225                 230                 235                 240

Ile Asp Glu Asn Ile Arg Pro Thr Phe Lys Glu Leu Ala Asn Glu Phe
                245                 250                 255

<210> SEQ ID NO 37
<211> LENGTH: 236
<212> TYPE: PRT
<213> ORGANISM: Homo sapiens

<400> SEQUENCE: 37

Lys Arg Val Lys Val Leu Gly Ser Gly Ala Phe Gly Thr Val Tyr Lys
1               5                   10                  15

Gly Ile Trp Val Pro Glu Gly Glu Thr Val Lys Ile Pro Val Ala Ile
            20                  25                  30

Lys Ile Leu Asn Glu Thr Thr Gly Pro Lys Ala Asn Val Glu Phe Met
        35                  40                  45

Asp Glu Ala Leu Ile Met Ala Ser Met Asp His Pro His Leu Val Arg
    50                  55                  60

Leu Leu Gly Val Cys Leu Ser Pro Thr Ile Gln Leu Val Thr Gln Leu
65                  70                  75                  80

Met Pro His Gly Cys Leu Leu Glu Tyr Val His Glu His Lys Asp Asn
                85                  90                  95

Ile Gly Ser Gln Leu Leu Asn Trp Cys Val Gln Ile Ala Lys Gly
            100                 105                 110

Met Met Tyr Leu Glu Glu Arg Arg Leu Val His Arg Asp Leu Ala Ala
        115                 120                 125

Arg Asn Val Leu Val Lys Ser Pro Asn His Val Lys Ile Thr Asp Phe
    130                 135                 140

Gly Leu Ala Arg Leu Leu Glu Gly Asp Glu Lys Glu Tyr Asn Ala Asp
145                 150                 155                 160

Gly Gly Lys Met Pro Ile Lys Trp Met Ala Leu Glu Cys Ile His Tyr
                165                 170                 175

Arg Lys Phe Thr His Gln Ser Asp Val Trp Ser Tyr Gly Val Thr Ile
            180                 185                 190

Trp Glu Leu Met Thr Phe Gly Gly Lys Pro Tyr Asp Gly Ile Pro Thr
        195                 200                 205

Arg Glu Ile Pro Asp Leu Leu Glu Lys Gly Glu Arg Leu Pro Gln Pro
    210                 215                 220

Pro Ile Cys Thr Ile Asp Val Tyr Met Val Met Val
225                 230                 235

<210> SEQ ID NO 38
<211> LENGTH: 249
<212> TYPE: PRT
<213> ORGANISM: Homo sapiens

<400> SEQUENCE: 38

Thr Phe Leu Lys Glu Leu Gly Thr Gly Gln Phe Gly Val Val Lys Tyr
1               5                   10                  15

Gly Lys Trp Arg Gly Gln Tyr Asp Val Ala Ile Lys Met Ile Lys Glu
            20                  25                  30

Gly Ser Met Ser Glu Asp Glu Phe Ile Glu Glu Ala Lys Val Met Met
        35                  40                  45

Asn Leu Ser His Glu Lys Leu Val Gln Leu Tyr Gly Val Cys Thr Lys
    50                  55                  60

Gln Arg Pro Ile Phe Ile Ile Thr Glu Tyr Met Ala Asn Gly Cys Leu
```

```
                65                  70                  75                  80
Leu Asn Tyr Leu Arg Glu Met Arg His Arg Phe Gln Thr Gln Gln Leu
                    85                  90                  95

Leu Glu Met Cys Lys Asp Val Cys Glu Ala Met Glu Tyr Leu Glu Ser
                100                 105                 110

Lys Gln Phe Leu His Arg Asp Leu Ala Ala Arg Asn Cys Leu Val Asn
                115                 120                 125

Asp Gln Gly Val Val Lys Val Ser Asp Phe Gly Leu Ser Arg Tyr Val
            130                 135                 140

Leu Asp Asp Glu Tyr Thr Ser Ser Val Gly Ser Lys Phe Pro Val Arg
145                 150                 155                 160

Trp Ser Pro Pro Glu Val Leu Met Tyr Ser Lys Phe Ser Ser Lys Ser
                    165                 170                 175

Asp Ile Trp Ala Phe Gly Val Leu Met Trp Glu Ile Tyr Ser Leu Gly
                180                 185                 190

Lys Met Pro Tyr Glu Arg Phe Thr Asn Ser Glu Thr Ala Glu His Ile
                    195                 200                 205

Ala Gln Gly Leu Arg Leu Tyr Arg Pro His Leu Ala Ser Glu Lys Val
            210                 215                 220

Tyr Thr Ile Met Tyr Ser Cys Trp His Glu Lys Ala Asp Glu Arg Pro
225                 230                 235                 240

Thr Phe Lys Ile Leu Leu Ser Asn Ile
                    245

<210> SEQ ID NO 39
<211> LENGTH: 391
<212> TYPE: PRT
<213> ORGANISM: Homo sapiens

<400> SEQUENCE: 39

Tyr Glu Ile Arg Trp Arg Val Ile Glu Ser Ile Ser Pro Asp Gly His
1               5                   10                  15

Glu Tyr Ile Tyr Val Asp Pro Met Gln Leu Pro Tyr Asp Ser Arg Trp
                20                  25                  30

Glu Phe Pro Arg Asp Gly Leu Val Leu Gly Arg Val Leu Gly Ser Gly
            35                  40                  45

Ala Phe Gly Lys Val Val Glu Gly Thr Ala Tyr Gly Leu Ser Arg Ser
        50                  55                  60

Gln Pro Val Met Lys Val Ala Val Lys Met Leu Lys Pro Thr Ala Arg
65                  70                  75                  80

Ser Ser Glu Lys Gln Ala Leu Met Ser Glu Leu Lys Ile Met Thr His
                    85                  90                  95

Leu Gly Pro His Leu Asn Ile Val Asn Leu Leu Gly Ala Cys Thr Lys
                100                 105                 110

Ser Gly Pro Ile Tyr Ile Ile Thr Glu Tyr Cys Phe Tyr Cys Asp Leu
            115                 120                 125

Val Asn Tyr Leu His Lys Asn Arg Asp Ser Phe Leu Ser His His Pro
        130                 135                 140

Glu Lys Pro Lys Lys Glu Leu Asp Ile Phe Gly Leu Asn Pro Ala Asp
145                 150                 155                 160

Glu Ser Thr Arg Ser Tyr Val Ile Leu Ser Phe Glu Asn Asn Gly Asp
                    165                 170                 175

Tyr Met Asp Met Lys Gln Ala Asp Thr Thr Gln Tyr Val Pro Met Leu
                180                 185                 190
```

```
Glu Arg Lys Glu Val Ser Lys Tyr Ser Asp Ile Gln Arg Ser Leu Tyr
            195                 200                 205

Asp Arg Pro Ala Ser Tyr Lys Lys Ser Met Leu Asp Ser Glu Val
210                 215                 220

Lys Asn Leu Leu Ser Asp Asn Ser Glu Gly Leu Thr Leu Leu Asp
225                 230                 235                 240

Leu Leu Ser Phe Thr Tyr Gln Val Ala Arg Gly Met Glu Phe Leu Ala
                245                 250                 255

Ser Lys Asn Cys Val His Arg Asp Leu Ala Ala Arg Asn Val Leu Leu
            260                 265                 270

Ala Gln Gly Lys Ile Val Lys Ile Cys Asp Phe Gly Leu Ala Arg Asp
            275                 280                 285

Ile Met His Asp Ser Asn Tyr Val Ser Lys Gly Ser Thr Phe Leu Pro
    290                 295                 300

Val Lys Trp Met Ala Pro Glu Ser Ile Phe Asp Asn Leu Tyr Thr Thr
305                 310                 315                 320

Leu Ser Asp Val Trp Ser Tyr Gly Ile Leu Leu Trp Glu Ile Phe Ser
                325                 330                 335

Leu Gly Gly Thr Pro Tyr Pro Gly Met Met Val Asp Ser Thr Phe Tyr
                340                 345                 350

Asn Lys Ile Lys Ser Gly Tyr Arg Met Ala Lys Pro Asp His Ala Thr
            355                 360                 365

Ser Glu Val Tyr Glu Ile Met Val Lys Cys Trp Asn Ser Glu Pro Glu
    370                 375                 380

Lys Arg Pro Ser Phe Tyr His
385                 390

<210> SEQ ID NO 40
<211> LENGTH: 275
<212> TYPE: PRT
<213> ORGANISM: Homo sapiens

<400> SEQUENCE: 40

Leu Val Leu Gly Lys Pro Leu Gly Glu Gly Cys Phe Gly Gln Val Val
1               5                   10                  15

Leu Ala Glu Ala Ile Gly Leu Asp Lys Asp Lys Pro Asn Arg Val Thr
                20                  25                  30

Lys Val Ala Val Lys Met Leu Lys Ser Asp Ala Thr Glu Lys Asp Leu
            35                  40                  45

Ser Asp Leu Ile Ser Glu Met Glu Met Met Lys Met Ile Gly Lys His
    50                  55                  60

Lys Asn Ile Ile Asn Leu Leu Gly Ala Cys Thr Gln Asp Gly Pro Leu
65                  70                  75                  80

Tyr Val Ile Val Glu Tyr Ala Ser Lys Cys Asn Leu Arg Glu Tyr Leu
                85                  90                  95

Gln Ala Arg Arg Pro Pro Gly Leu Glu Tyr Cys Tyr Asn Pro Ser His
            100                 105                 110

Asn Pro Glu Glu Gln Leu Ser Ser Lys Asp Leu Val Ser Cys Ala Tyr
        115                 120                 125

Gln Val Ala Arg Gly Met Glu Tyr Leu Ala Ser Lys Lys Cys Ile His
    130                 135                 140

Arg Asp Leu Ala Ala Arg Asn Val Leu Val Thr Glu Asp Asn Val Met
145                 150                 155                 160

Lys Ile Ala Asp Phe Gly Leu Ala Arg Asp Ile His His Ile Asp Tyr
                165                 170                 175
```

```
Tyr Lys Lys Thr Thr Asn Gly Arg Leu Pro Val Lys Trp Met Ala Pro
            180                 185                 190

Glu Ala Leu Phe Asp Arg Ile Tyr Thr His Gln Ser Asp Val Trp Ser
            195                 200                 205

Phe Gly Val Leu Leu Trp Glu Ile Phe Thr Leu Gly Gly Ser Pro Tyr
            210                 215                 220

Pro Gly Val Pro Val Glu Glu Leu Phe Lys Leu Leu Lys Glu Gly His
225                 230                 235                 240

Arg Met Asp Lys Pro Ser Asn Cys Thr Asn Glu Leu Tyr Met Met Met
                245                 250                 255

Arg Asp Cys Trp His Ala Val Pro Ser Gln Arg Pro Thr Phe Lys Gln
            260                 265                 270

Leu Val Glu
        275

<210> SEQ ID NO 41
<211> LENGTH: 248
<212> TYPE: PRT
<213> ORGANISM: Homo sapiens

<400> SEQUENCE: 41

Leu Arg Leu Glu Val Lys Leu Gly Gln Gly Cys Phe Gly Glu Val Trp
1               5                   10                  15

Met Gly Thr Trp Asn Gly Thr Thr Arg Val Ala Ile Lys Thr Leu Lys
            20                  25                  30

Pro Gly Thr Met Ser Pro Glu Ala Phe Leu Gln Glu Ala Gln Val Met
            35                  40                  45

Lys Lys Leu Arg His Glu Lys Leu Val Gln Leu Tyr Ala Val Val Ser
        50                  55                  60

Glu Glu Pro Ile Tyr Ile Val Thr Glu Tyr Met Ser Lys Gly Ser Leu
65                  70                  75                  80

Leu Asp Phe Leu Lys Gly Glu Thr Gly Lys Tyr Leu Arg Leu Pro Gln
                85                  90                  95

Leu Val Asp Met Ala Ala Gln Ile Ala Ser Gly Met Ala Tyr Val Glu
            100                 105                 110

Arg Met Asn Tyr Val His Arg Asp Leu Arg Ala Ala Asn Ile Leu Val
            115                 120                 125

Gly Glu Asn Leu Val Cys Lys Val Ala Asp Phe Gly Leu Ala Arg Leu
        130                 135                 140

Ile Glu Asp Asn Glu Tyr Thr Ala Arg Gln Gly Ala Lys Phe Pro Ile
145                 150                 155                 160

Lys Trp Thr Ala Pro Glu Ala Ala Leu Tyr Gly Arg Phe Thr Ile Lys
                165                 170                 175

Ser Asp Val Trp Ser Phe Gly Ile Leu Leu Thr Glu Leu Thr Thr Lys
            180                 185                 190

Gly Arg Val Pro Tyr Pro Gly Met Val Asn Arg Glu Val Leu Asp Gln
            195                 200                 205

Val Glu Arg Gly Tyr Arg Met Pro Cys Pro Pro Glu Cys Pro Glu Ser
        210                 215                 220

Leu His Asp Leu Met Cys Gln Cys Trp Arg Lys Glu Pro Glu Glu Arg
225                 230                 235                 240

Pro Thr Phe Glu Tyr Leu Gln Ala
                245
```

<210> SEQ ID NO 42
<211> LENGTH: 254
<212> TYPE: PRT
<213> ORGANISM: Homo sapiens

<400> SEQUENCE: 42

```
Glu Val Ile Gly Arg Gly His Phe Gly Cys Val Tyr His Gly Thr Leu
1               5                   10                  15

Leu Asp Asn Asp Gly Lys Lys Ile His Cys Ala Val Lys Ser Leu Asn
            20                  25                  30

Arg Ile Thr Asp Ile Gly Glu Val Ser Gln Phe Leu Thr Glu Gly Ile
        35                  40                  45

Ile Met Lys Asp Phe Ser His Pro Asn Val Leu Ser Leu Leu Gly Ile
50                  55                  60

Cys Leu Arg Ser Glu Gly Ser Pro Leu Val Val Leu Pro Tyr Met Lys
65                  70                  75                  80

His Gly Asp Leu Arg Asn Phe Ile Arg Asn Glu Thr His Asn Pro Thr
                85                  90                  95

Val Lys Asp Leu Ile Gly Phe Gly Leu Gln Val Ala Lys Gly Met Lys
            100                 105                 110

Tyr Leu Ala Ser Lys Lys Phe Val His Arg Asp Leu Ala Ala Arg Asn
        115                 120                 125

Cys Met Leu Asp Glu Lys Phe Thr Val Lys Val Ala Asp Phe Gly Leu
130                 135                 140

Ala Arg Asp Met Tyr Asp Lys Glu Tyr Tyr Ser Val His Asn Lys Thr
145                 150                 155                 160

Gly Ala Lys Leu Pro Val Lys Trp Met Ala Leu Glu Ser Leu Gln Thr
                165                 170                 175

Gln Lys Phe Thr Thr Lys Ser Asp Val Trp Ser Phe Gly Val Leu Leu
            180                 185                 190

Trp Glu Leu Met Thr Arg Gly Ala Pro Pro Tyr Pro Asp Val Asn Thr
        195                 200                 205

Phe Asp Ile Thr Val Tyr Leu Leu Gln Gly Arg Arg Leu Leu Gln Pro
210                 215                 220

Glu Tyr Cys Pro Asp Pro Leu Tyr Glu Val Met Leu Lys Cys Trp His
225                 230                 235                 240

Pro Lys Ala Glu Met Arg Pro Ser Phe Ser Glu Leu Val Ser
                245                 250
```

<210> SEQ ID NO 43
<211> LENGTH: 247
<212> TYPE: PRT
<213> ORGANISM: Homo sapiens

<400> SEQUENCE: 43

```
Thr Phe Leu Lys Glu Leu Gly Thr Gly Gln Phe Gly Val Val Lys Tyr
1               5                   10                  15

Gly Lys Trp Arg Gly Gln Tyr Asp Val Ala Ile Lys Met Ile Lys Glu
            20                  25                  30

Gly Ser Met Ser Glu Asp Glu Phe Ile Glu Glu Ala Lys Val Met Met
        35                  40                  45

Asn Leu Ser His Glu Lys Leu Val Gln Leu Tyr Gly Val Cys Thr Lys
50                  55                  60

Gln Arg Pro Ile Phe Ile Ile Thr Glu Tyr Met Ala Asn Gly Cys Leu
65                  70                  75                  80

Leu Asn Tyr Leu Arg Glu Met Arg His Arg Phe Gln Thr Gln Gln Leu
```

```
                      85                  90                  95
Leu Glu Met Cys Lys Asp Val Cys Glu Ala Met Glu Tyr Leu Glu Ser
                100                 105                 110

Lys Gln Phe Leu His Arg Asp Leu Ala Ala Arg Asn Cys Leu Val Asn
            115                 120                 125

Asp Gln Gly Val Val Lys Val Ser Asp Phe Gly Leu Ser Arg Tyr Val
        130                 135                 140

Leu Asp Asp Glu Tyr Thr Ser Ser Val Gly Ser Lys Phe Pro Val Arg
145                 150                 155                 160

Trp Ser Pro Pro Glu Val Leu Met Tyr Ser Lys Phe Ser Ser Lys Ser
                165                 170                 175

Asp Ile Trp Ala Phe Gly Val Leu Met Trp Glu Ile Tyr Ser Leu Gly
            180                 185                 190

Lys Met Pro Tyr Glu Arg Phe Thr Asn Ser Glu Thr Ala Glu His Ile
        195                 200                 205

Ala Gln Gly Leu Arg Leu Tyr Arg Pro His Leu Ala Ser Glu Lys Val
    210                 215                 220

Tyr Thr Ile Met Tyr Ser Cys Trp His Glu Lys Ala Asp Glu Arg Pro
225                 230                 235                 240

Thr Phe Lys Ile Leu Leu Ser
                245

<210> SEQ ID NO 44
<211> LENGTH: 10
<212> TYPE: DNA
<213> ORGANISM: Homo sapiens

<400> SEQUENCE: 44
ttatcttaat                                                            10

<210> SEQ ID NO 45
<211> LENGTH: 21
<212> TYPE: DNA
<213> ORGANISM: Homo sapiens

<400> SEQUENCE: 45
accaaattat gcggaatcca t                                               21

<210> SEQ ID NO 46
<211> LENGTH: 15
<212> TYPE: DNA
<213> ORGANISM: Homo sapiens

<400> SEQUENCE: 46
tccatcttac cctgg                                                      15

<210> SEQ ID NO 47
<211> LENGTH: 15
<212> TYPE: DNA
<213> ORGANISM: Homo sapiens

<400> SEQUENCE: 47
tccggcgggt tttag                                                      15

<210> SEQ ID NO 48
<211> LENGTH: 23
<212> TYPE: DNA
<213> ORGANISM: Homo sapiens

<400> SEQUENCE: 48
```

```
gttttaggga cgttaaccta gta                                          23

<210> SEQ ID NO 49
<211> LENGTH: 15
<212> TYPE: DNA
<213> ORGANISM: Homo sapiens

<400> SEQUENCE: 49
taaagaaaca gttca                                                   15

<210> SEQ ID NO 50
<211> LENGTH: 21
<212> TYPE: DNA
<213> ORGANISM: Homo sapiens

<400> SEQUENCE: 50
aaacagttca gaacgtgcaa t                                            21

<210> SEQ ID NO 51
<211> LENGTH: 13
<212> TYPE: DNA
<213> ORGANISM: Homo sapiens

<400> SEQUENCE: 51
tcctcattac ttg                                                     13

<210> SEQ ID NO 52
<211> LENGTH: 12
<212> TYPE: DNA
<213> ORGANISM: Homo sapiens

<400> SEQUENCE: 52
cctcattaac tc                                                      12

<210> SEQ ID NO 53
<211> LENGTH: 8
<212> TYPE: DNA
<213> ORGANISM: Homo sapiens

<400> SEQUENCE: 53 ccacccccc                                                           8

<210> SEQ ID NO 54
<211> LENGTH: 13
<212> TYPE: DNA
<213> ORGANISM: Homo sapiens

<400> SEQUENCE: 54
tagcccggtc cct                                                     13

<210> SEQ ID NO 55
<211> LENGTH: 7
<212> TYPE: DNA
<213> ORGANISM: Homo sapiens

<400> SEQUENCE: 55 agattgg                                                             7

<210> SEQ ID NO 56
<211> LENGTH: 8
<212> TYPE: DNA
<213> ORGANISM: Homo sapiens
```

```
<400> SEQUENCE: 56 ttgggttg                                                                8

<210> SEQ ID NO 57
<211> LENGTH: 19
<212> TYPE: DNA
<213> ORGANISM: Homo sapiens

<400> SEQUENCE: 57
tatcgagtcc acacaggag                                                   19

<210> SEQ ID NO 58
<211> LENGTH: 15
<212> TYPE: DNA
<213> ORGANISM: Homo sapiens

<400> SEQUENCE: 58
gctggatgtt actcg                                                       15

<210> SEQ ID NO 59
<211> LENGTH: 15
<212> TYPE: DNA
<213> ORGANISM: Homo sapiens

<400> SEQUENCE: 59
catgcttgcg tgagc                                                       15

<210> SEQ ID NO 60
<211> LENGTH: 11
<212> TYPE: DNA
<213> ORGANISM: Homo sapiens

<400> SEQUENCE: 60
cttgcgtgag c                                                           11

<210> SEQ ID NO 61
<211> LENGTH: 9
<212> TYPE: DNA
<213> ORGANISM: Homo sapiens

<400> SEQUENCE: 61 gcaaacgga                                                               9

<210> SEQ ID NO 62
<211> LENGTH: 13
<212> TYPE: DNA
<213> ORGANISM: Homo sapiens

<400> SEQUENCE: 62
caaacggaag tat                                                         13

<210> SEQ ID NO 63
<211> LENGTH: 15
<212> TYPE: DNA
<213> ORGANISM: Homo sapiens

<400> SEQUENCE: 63
aacggaagta tatag                                                       15

<210> SEQ ID NO 64
<211> LENGTH: 12
<212> TYPE: DNA
<213> ORGANISM: Homo sapiens
```

```
<400> SEQUENCE: 64
cgccctcggg cg                                                              12

<210> SEQ ID NO 65
<211> LENGTH: 8
<212> TYPE: DNA
<213> ORGANISM: Homo sapiens

<400> SEQUENCE: 65 acttcctc                                                                    8

<210> SEQ ID NO 66
<211> LENGTH: 21
<212> TYPE: DNA
<213> ORGANISM: Homo sapiens

<400> SEQUENCE: 66
gguuauugga ugcccauuau u                                                    21

<210> SEQ ID NO 67
<211> LENGTH: 21
<212> TYPE: DNA
<213> ORGANISM: Homo sapiens

<400> SEQUENCE: 67
uaaugggcau ccaauaaccu u                                                    21

<210> SEQ ID NO 68
<211> LENGTH: 21
<212> TYPE: DNA
<213> ORGANISM: Homo sapiens

<400> SEQUENCE: 68
caacaaaugg uuauuggauu u                                                    21

<210> SEQ ID NO 69
<211> LENGTH: 21
<212> TYPE: DNA
<213> ORGANISM: Homo sapiens

<400> SEQUENCE: 69
auccaauaac cauuuguugu u                                                    21
```